United States Patent
Stoecker et al.

(10) Patent No.: US 7,689,016 B2
(45) Date of Patent: Mar. 30, 2010

(54) AUTOMATIC DETECTION OF CRITICAL DERMOSCOPY FEATURES FOR MALIGNANT MELANOMA DIAGNOSIS

(75) Inventors: William V. Stoecker, Rolla, MO (US); Randy H. Moss, Rolla, MO (US); R. Joe Stanley, Rolla, MO (US); Xiaohe Chen, Rolla, MO (US); Kapil Gupta, Rolla, MO (US); Bijaya Shrestha, Rolla, MO (US); Pavani Jella, Boise, ID (US)

(73) Assignees: Stoecker & Associates, a subsidiary of The Dermatology Center, LLC, Rolla, MO (US); The Curators of the University of Missouri, Columbia, MO (US)

( * ) Notice: Subject to any disclaimer, the term of this patent is extended or adjusted under 35 U.S.C. 154(b) by 856 days.

(21) Appl. No.: 11/421,031

(22) Filed: May 30, 2006

(65) Prior Publication Data
US 2006/0269111 A1 Nov. 30, 2006

Related U.S. Application Data

(60) Provisional application No. 60/685,664, filed on May 27, 2005.

(51) Int. Cl.
*G06K 9/00* (2006.01)

(52) U.S. Cl. ...................................... 382/128

(58) Field of Classification Search .................. 382/100, 382/128, 130, 131, 132, 162, 164, 165, 168, 382/170, 171, 172, 173, 174, 180, 190, 191, 382/195, 199, 206, 224, 225, 228, 274, 275, 382/286; 128/922; 345/622
See application file for complete search history.

(56) References Cited

U.S. PATENT DOCUMENTS

| | | | | |
|---|---|---|---|---|
| 5,146,923 A * | 9/1992 | Dhawan | | 600/476 |
| 6,697,497 B1 * | 2/2004 | Jensen et al. | | 382/100 |
| 6,819,790 B2 * | 11/2004 | Suzuki et al. | | 382/156 |
| 7,006,223 B2 * | 2/2006 | Mullani | | 356/369 |
| 2004/0017938 A1 * | 1/2004 | Cooper et al. | | 382/171 |
| 2004/0264749 A1 * | 12/2004 | Skladnev et al. | | 382/128 |

OTHER PUBLICATIONS

Skladnev, et al., Boundary Finding in Dermatological Exam, WIPO Publication WO 02/094097 A1, Nov. 28, 2002.*

(Continued)

*Primary Examiner*—Andrew W Johns
*Assistant Examiner*—Tahmina Ansari
(74) *Attorney, Agent, or Firm*—Greenlee, Winner and Sullivan, P.C.

(57) ABSTRACT

Improved methods for computer-aided analysis of identifying features of skin lesions from digital images of the lesions are provided. Improved preprocessing of the image that 1) eliminates artifacts that occlude or distort skin lesion features and 2) identifies groups of pixels within the skin lesion that represent features and/or facilitate the quantification of features are provided including improved digital hair removal algorithms. Improved methods for analyzing lesion features are also provided.

22 Claims, 28 Drawing Sheets

OTHER PUBLICATIONS

Anantha et al. (2004) "Detection of Pigment Network in Dermatoscopy Images Using Texture Analysis," *Compute. Med. Imag. Graph.* 28(5):225-234.

Argenziano et al. (1998) "Epiluminescence Microscopy for the Diagnosis of Doubtful Melanocytic Skin Lesions, Comparison of the ABCD Rule of Dermatoscopy and a New 7-Point Checklist Based on Pattern Analysis," *Arch. Dermatol.* 134(12): 1563-1570.

Argenziano et al. (2003) "Dermoscopy of Pigmented Skin Lesions: Results of a Consensus Meeting Via the Internet," *J. Am. Acad. Dermatol.* 48(5):679-693.

Argenziano et al. (2002) "Impact of Dermoscopy on the Clinical Management of Pigmented Skin Lesions," *Clin. Dermatol.* 20:200-202.

Binder et al. (1995) "Epiluminescence Microscopy. A Useful Tool for the Diagnosis of Pigmented Skin Lesions for Formally Trained Dermatologists," *Arch. Dermatol.* 131:286-291.

Binder et al. (2000) "Computer-Aided Epiluminescence Microscopy of Pigmented Skin Lesions: The Value of Clinical Data for the Classification Process," *Melanoma Res.* 10(6):556-561.

Bleau et al. (2000) "Watershed-Based Segmentation and Region Merging," *Computer Vision and Image Understating* 77(3):317-370.

Blum et al. (May 2003) "Modified ABC-Point List of Dermoscopy: A Simplified and Highly Accurate Dermoscopic Algorithm for the Diagnosis of Cutaneous Melanocytic Lesions," *J. Am. Acad. Dermatol.* 48(5):672-678.

Bono et al. (2002) "Clinical and Dermatoscopic Diagnosis of Small Pigmented Skin Lesions," *Eur. J. Dermatol.* 12(6):573-576.

Breiman et al. (2001) "Random Forests" *Machine Learning* 45(1):5-32.

Carli et al. (2000) "Dermatoscopy in the Diagnosis of Pigmented Skin Legions: A New Seminologu for the Dermatologist," *J. Eur. Acad. Dermatol. Venereol.* 14(5):353-369.

Cotton et al. (1996) "Developing a Predictive Model of Human Skin Colouring," *Proc. SPIE Med. Imaging* 2708:814-825.

Cotton et al. (1999) "A Skin Imaging Method Based on a Colour Formation Model and Its Application to the Diagnosis of Pigmented Skin Lesions," *Proc. Med. Imaging Analysis Understanding,* Oxford: BMVA 49-52.

Dal Pozzo et al. (1999) "The Seven Features for Melanoma: A New Dermoscopic Algorithm for the Diagnosis of Malignant Melanoma," *Eur. J. Dermatol.* 9:303-308.

Eddins, S. (Feb. 2002) "The Watershed Transform, Strategies for Image Segmentation," *The Mathworks Journal, Matlab News and Notes.*

Elbaum et al. (2001) "Automatic Differentiation of Melanoma from Melanocyte Nevi with MultiSpectral Digital Dermoscopy: A Feasibility Study," *J. Am. Acad. Dermatol.* 44(2):207-218.

Erkol et al. (2005) "Automatic Lesion Boundary Detection in Dermoscopy Images Using Gradient Vector Flow Snakes," *Skin Res. Technol.* 11(1):17-26.

Faziloglu et al. (May 2003) "Colour Histogram Analysis for Melanoma Discrimination in Clinical Images," *Skin Res. Technol.* 9(2):147-156.

Felkel, P. (2001) "Implementation and Complexity of the Watershed-From-Markers Algorithm Computed as a Minimal Cost Forest," Computer Graphic Forum, VrVis Center, Lothringerstrabe, Vienna, Austria.

Fleming et al. (1998) "Techniques for a Structural Analysis of Dermatoscopic Imagery," *Comput. Med. Imag. Graph.* 22:375-389.

Grana et al. (2006) "Distance Transform for Automatic Dermatological Images Composition," *Proc. SPIE* 6144:914-922.

Grana et al. (2006) "Line Detection and Texture Characterization of Network Patterns," *Proceedings of the 18th International Conference on Pattern Recognition* 2:275-278.

Gupta et al. (2005) "Detection of Globules in Dermoscopy Images of Malignant Melanoma: Absolue vs. Relative Color," *Comp. Med. Imag. Graphics* Submitted.

Hance et al. (1996) "Unsupervised Color Image Segmentation with Application to Skin Tumor Borders," *IEEE Eng. Med. Biol.* 15(1):104-111.

Haralick et al. (1973) "Textural Features for Image Classification," *IEEE Transactions on Systems Man Cybernetics* 3:610-621.

Hoffman et al. (Oct. 2003) "Diagnostic and Neutral Analysis of Skin Cancer (DANAOS). A Multicentre Study for Collection and Computer-Aided Analysis of Data from Pigmented Skin Legions Using Digital Dermoscopy," *Br. J. Dermatol.* 149(4):801-809.

Jamora et al. (2003) "Improved Identification of Potentially Dangerous Pigmented Skin Legions by Computerized Image Analysis," *Arch. Dermatol.* 139(2):195-198.

Jella, P. (2004) "Pigment Network Extraction and Sailent Point Analysis," MS Thesis, Electrical Engineering, University of Missouri-Rolla.

Jemal et al. (2006) "Cancer Statistics 2006," *Ca-A Cancer for Clinicians* 55:10-30.

Kittler et al. (1999) "Morphologic Changes of Pigmented Skin Legions: A Useful Extension of the ABCD Rule for Deratoscopy," *J. Am. Acad. Dermatol.* 40:558-562.

Lee et al. (1997) "DullRazor: A Software Approach to Hair Removal from Images," *Comput. Biol. Med.* 27(6):533-543.

Mangan et al. (1998) "Surface Segmentation Using Morphological Watersheds," *IEEE Visualization: Late Breaking Topics* :2932.

Massi et al. (2001) "Diagnostic Significance of the Blue Hue in Dermoscopy of Melanocytic Lesions: A Dermoscopic-Pathologic Study," *Am. J. Dermatopathology* 23(5):463-469.

McLean et al. (1994) "Tumor Classification Based on Relative Color Analysis of Melanoma and Non-Melanoma Tumor Images," M. S. Theisi. Department of Electrical Engineering, University of Missouri, Rolla.

Menzies et al. (1996) "Frequency and Morphologic Characteristics of Invasive Melanomas Lackin Specific Surface Microscopic Features," *Arch. Dermatol.* 132:1178-1182.

Moncrieff et al. (2001) "SIAscopy Assists in the Diagnosis of Melanoma by Utilizing Computer Vision Techniques to Visualize the Internal Structure of the Skin," In; *Med Image Understanding Analysis,* Claridge et al. eds., York, UK, pp. 53-56.

Moncrieff et al. (2002) "Spectrophotometric Intracutaneous Analysis: A New Technique for Imaging Pigmented Lesions," *Br. J. Dermatol.* 146:448-457.

Nachbar et al. (1004) "The ABCD Rule of Dermatoscopy," *J. Am. Acad. Dermatol.* 30:551-559 Abstract.

Pagadala et al. (1998) "Tumor Border Detection in Epiluminescence Microscopy Images," M.S. Thesis, Department of Electrical Engineering, University of Missouri-Rolla.

Rosado et al. (2003) "Accuracy of Computer Diagnosis of Melanoma. A Quantitative Meat-Analysis," *Arch Dermatol.* 139:361-367.

Rubengni et al. (2002) "Digital Dermoscopy Analysis and Artificial Neural Network for the Differentiation of Clinically Atypical Pigmented Skin Lesions: A Retrospective Study," *J. Invest Dermatol.* 119:471-474.

Seidenari, S. (2006) Differentiating Common Nevi from Atypical Nevi and Melanoma in Situ, First Congress of the International Dermoscopy Society. Naples, Italy, Apr. 27-29, Abstract: *Dermatology* 212:279.

Stanley et al. (2003) "A Fuzzy-Based Histogram Analysis Technique for Skin Lesion Discrimination in Dermatology Clinical Images," *Comp. Med. Imag. Graphics* 27:387-396.

Steger, C. (1996) "Extracting Lines Using Differential Geometry and Gaussian Smoothing," *Int. Arch Photogrammetry Remote Sensing* 3(3):821-826.

Steger, C. (Feb. 1998) "An Unbiased Detector of Curvilinear Structures," *IEEE Trans Pattern Analysis Machine Intelligence* 20(2):113-125.

Stoecker et al. (2005) "Detection of Asymmetric Blotches in Dermoscopy Images of Malignant Melanoma Using Relative Color," *Skin Res. Technol.* 11(3):179-184.

Stolz et al. (1996) "Improvement of Monitoring of Melanocytic Skin Lesions with the Use of a Computerized Acquisition and Surveillance Unit with a Skin Surface Microscopic Television Camera," *J. AM. Acad. Dermatol.* 35:202-207.

Stolz, W. (Mar. 2001) "DermoGenius Ultra," Presentation at the International Society of Digital Imaging of the Skin, Washington DC.

Tatikonda, S. (2002) "Automatic Detection of Regression and Granularity in Dermatoscopy Images of Skin Cancer," M.S. Thesis, Department of Electrical and Computer Engineering, University of Missouri, Rolla.

Thorn et al. (1998) "Rapid Increase in Diagnosis of Cutaneous Melanoma in Situ in Sweeden, 1968-1992," *Ca Detection and Prevention* 22:430.

Umbaugh et al. (1992) "An Automatic Color Segmentation Algorithm with Application to Identification of Skin Tumor Borders," *Comp. Med. Imag. Graphics* 16(3):227-235.

Umbaugh et al. (Dec. 1989) "Automatic Color Segmentation of Images with Application to detection of Variegated Coloring in Skin Tumors," *Eng. Med. Biol.* 8(4):43-52.

Vincent et al. (1991) "Watersheds in Digital Spaces: An Efficient Algorithm Based on Immersion Simulations," *IEEE Trans. Pattern Analysis and Machine Intelligence* 13(6):583-598.

\* cited by examiner

A

B

C

A

B

C

A

B

A

B

A

B

A

B

A

B

C

D

A

B

AUTOMATIC DETECTION OF CRITICAL DERMOSCOPY FEATURES FOR MALIGNANT MELANOMA DIAGNOSIS

CROSS-REFERENCE TO RELATED APPLICATIONS

This application claims priority to U.S. Provisional Application Ser. No. 60/685,664 filed May 27, 2005, which is incorporated herein by reference to the extent not inconsistent herewith.

BACKGROUND

Malignant melanoma, with 62,190 new cases and 7770 deaths estimated in 2006 (Jemal06), is easily cured if detected at an early stage. To the total of 62,190 new cases of melanoma, we can add an estimated 49,710 cases of melanoma in situ in 2006 (Jemal06), a number growing at 15% per year in some countries (Thom98). Dermatologists' accuracy in diagnosis of pigmented lesions with dermoscopy is higher than without dermoscopy (Binder95). Diagnostic accuracy is at least as high with digital dermoscopy, especially when combined with clinical data (Binder00). Digital analysis of dermoscopic images gives more accurate results than digital analysis of clinical images (Rosado03). The diagnostic accuracy achievable by digital dermoscopy is in the range of 93%, offering no significant improvement so far in diagnostic performance over that of a dermatologist trained in dermoscopy (Rosado03, Rubegni02). Combining clinical and dermoscopic examinations has improved melanoma diagnostic accuracy (Bono02).

Dermoscopy (Epiluminescence Microscopy (ELM), Dermatoscopy)

Dermoscopy is a technique for viewing skin lesions with 10-power or more magnification. The dermoscopy may occur with a glass plate (contact dermoscopy) with a fluid, gel, mineral oil, or alcohol, between the skin and the glass plate, or illumination with cross polarization and no glass plate or fluid (non-contact dermoscopy).

An unknown but growing number of American dermatologists are using dermoscopy, approximately 23% in 2001 and probably still a minority, compared to nearly all dermatologists in Europe (Rabinovitz01). From personal experience on rxderm-I, the national dermatology discussion group with a server at the University of California, Davis, much of the growth in American use has been with non-contact dermoscopy.

The four most popular dermoscopy algorithms are the pattern analysis method, ABCD rule, the Menzies method, and the 7-point checklist. The most popular, the pattern analysis method, is based on the qualitative assessment of a varying number of individual ELM criteria including global pattern, pigment network, dots/globules, blue veil, blotches, hypopigmentation, regression structures, and vascular structures observed within a given pigmented skin lesion (Carli99, Argenziano98, Argenziano03). A virtual meeting of 40 experienced dermoscopists had diagnoses tabulated for 108 pigmented skin lesions. The consensus diagnosis was the diagnosis agreed upon by over 50% of observers. The pattern analysis system, scored here for 24 features, showed the highest consensus diagnosis sensitivity of the four systems: 100%, with a specificity of 88%, although the numbers of dermoscopists testing the systems were too low to achieve significance (Argenziano03).

The dermoscopy ABCD rule (Nachbar94, Argenziano03) totals points for asymmetry about 0, 1, or 2 axes, border cutoffs in 0-2, 3-5 or 6-8 octants, color numbers of 1, 2-3, or 4-5, and 1, 2-3, or 4-5 structures. This was first reported to show sensitivity of about 92% and specificity of about 91%, but showed consensus sensitivity and specificity of about 96% and 70% in the virtual consensus meeting (Argenziano03). This system is sometimes modified to include information about morphologic changes reported by the patient, sometimes called the ABCDE rule, improving the sensitivity about 3% (90% to 93%) in one study (Kittler99).

The 7-point checklist (atypical pigment network, blue-whitish veil, atypical vascular pattern, irregular streaks, irregular pigmentation, and dots/globules or regression structures) has shown sensitivity as high as 95%, and a specificity of 86% (Dal Pozzo99). There have been variations of the seven features (Argenziano98) and one variation has 11 points (Carli99). The consensus sensitivity and specificity for the 7-point checklist was 96% and 73% (Argenziano03).

Menzies and colleagues (Menzies96b) have developed a method based upon number of colors, symmetry of pattern, and one or more positive features. The technique has a reported 92% sensitivity and 71% specificity, (96% and 73% consensus sensitivity and specificity) (Argenziano03).

Digital Dermoscopy

Computer systems that use dermoscopy images, sometimes called digital dermoscopy systems, yield better diagnostic accuracy than those that use clinical images. Their diagnostic accuracy is generally not statistically different from that obtained by physicians with experience using dermoscopy. One digital dermoscopy system, called DermoGenius Ultra, previously marketed by Linos, Munich, was developed by Stolz and colleagues (Stolz96, Stolz01). The software for this device is based on the ABCD algorithm for dermoscopy noted above. (Nachbar94) The ABCs are calculated to approximate the dermoscopy ABCs and the scaling index was developed to replace the D to approximate the degree of heterogeneity in the image, as the system cannot identify structures. Used on 187 patients at risk for melanoma, it recommended removal of 52 lesions that appeared clinically unsuspicious, one of which was a melanoma in situ, and eight of which had at least moderate atypia (Jamora03).

The DANAOS system has achieved the planned collaboration announced in 1997 and has collected 2218 images of pigmented skin lesions. Neural network diagnostic results were again within range of that achieved by trained dermoscopists (Hoffman03).

The DBDermo-MIPS program (Biomedical Engineering Dell'Eva-Burroni, Siena) has analyzed more than 10,350 pigmented lesions. The group obtained a diagnostic accuracy of 93% on atypical, flat, diagnostically difficult lesions, including melanomas with a median thickness of 0.2 mm and dysplastic nevi (Rubegni02).

All the above digital dermoscopy systems use contact dermoscopy, with little analysis, as yet, appearing with non-contact magnification. One international project launched in February 2004 at the International Dermoscopy Meeting was an attempt to obtain better diagnostic accuracy for amelanotic/hypomelanotic melanomas. Different technologies proposed to solve this problem include non-contact dermoscopy such as the 3Gen DermLite B magnifying viewer, 3Gen LLC, Dana Point, Calif., and higher magnification, 30× or more, with analysis of vascular patterns. It is probable that for the current generation of digital dermoscopy systems, a core of difficult lesions will not be amenable to diagnosis, in part because limited attention has been given to structures other than attempts to find them statistically and in part because digital dermoscopy systems cannot separate early melanomas from benign lesions.

Hyperspectral Image Analysis

The Melafind system, by Electro-Optical Sciences, Irvington, N.Y., uses broadband Light-Emitting Diodes (LEDs) to obtain ten spectral images ranging from 430 nm to 950 nm, of which eight are used by a linear classifier. The best-performing linear classifier yielded an accuracy of 89% on a difficult set of images, including dysplastic and congenital nevi. The system uses wavelet analysis of image slices, with no published attempts to identify structures (Elbaum01).

A second system, SIAscopy, developed by Astron Clinica, Cambridge, U.K., uses eight infrared as well as visible image bands, ranging from 400 to 1000 nm (Cotton96, Cotton99, Moncrief01). Analysis proceeds to identify the amount, distribution, and depth of certain critical features including collagen, melanin, and blood within the skin. For lesions greater than 6 mm, using just two characteristic features, the system gave a diagnostic sensitivity of about 83% and a specificity of 80% (Moncrief02).

Problems with Existing Digital Imaging Systems

The above proprietary platforms are costly. Several of the devices are undergoing clinical trials before 510(k) approval, and are not for sale. Several systems are available costing in the range of $20,000. Relatively few clinics see enough pigmented lesion patients to justify such costs. One manufacturer has discussed a per-image analysis fee, with costs presumably to be borne by insurers. But the use of inexpensive digital cameras is likely to grow, with dermatologists increasingly acquiring images with digital cameras such as one of the Nikon series and the 3Gen DermLite II Pro attachment, advertised on the dermlite.com website.

All publications referred to herein are incorporated by reference to the extent not inconsistent herewith.

SUMMARY

Selected dermoscopy features that are identifiable by computer are summarized here. This invention provides improved computer-aided analysis of dermoscopy images of skin lesions.

The algorithms of this invention can be applied to multiple platforms, including any digital camera with an add-on device for 10-power magnification, or any device with magnification within the range of 8-30 power. These devices include but are not limited to the Canfield Epilight, Canfield Imaging Systems, Fairfield, N.J., the 3Gen DermLite II Pro, 3Gen LLC, Dana Point, Calif., and the Heine Dermaphot, Heine Dermaphot Optics, Heine Ltd, Herrsching, Germany. All such images may be classified as dermoscopy images.

In one embodiment, this invention provides a method for identifying a border between a skin lesion and surrounding skin on a digital image of a skin lesion comprising (a) preprocessing the image to identify pixels that represent features other than skin and lesion; (b) determining a first lesion ratio estimate of the image using bounding box methods; (c) subsequently applying a lesion ratio offset to produce a corrected lesion ratio estimate by running a classifier algorithm that incorporates color and histogram data from both inside and outside a bounding box; and (d) inputting the corrected lesion ratio estimate into a watershed algorithm for identifying a border between a skin lesion and surrounding skin.

Features other than skin and lesion on the image are referred to herein as "noise" and can include measurement markings, e.g., the image of a ruler, ink, shadow, flash, hair, bubbles, and other artifacts. The lesion ratio is the ratio of the area of a lesion divided by the area of the entire image. A lesion ratio estimate is an estimate of the lesion ratio, which may be obtained by several methods including bounding box and histogram methods. A lesion ratio estimate can be determined by determining a bounding box, wherein box borders are determined by a subtraction curve applied to horizontal and vertical projections of the luminance image or other similar linear combination or representation of the color planes. An example of a bounding box is shown in FIG. 11. In one embodiment of this invention, the absence of a bounding box indicates that the lesion extends to the periphery of the image, and the presence of a bounding box indicates that the lesion does not extend to the periphery of the image. Bounding box information is often stored as a separate binary image, for example with 0 for background and 1 for lesion.

The luminance of a pixel is defined as 0.3 R+0.59 G+0.11 B, where R, G, and B are the red, green and blue intensity values of a pixel. A single-plane image can be represented by assigning different weights, summing to one, to R, G, and B compared to luminance. One example is the independent histogram pursuit (IHP) image, wherein the R, G, and B weights are chosen to maximize the area of the valley between histogram peaks on the image with the chosen weights (Gomez06). In the following definitions and detailed explanations, any single plane image such as the IHP image may be substituted for the luminance image. Representations of color, also known as color spaces, other than the ROB space can be used, such as the Intensity, Hue, Saturation (IHS) space. In a similar manner, weights can be assigned to the variables in any color space to create a single-plane image.

A lesion ratio offset is a correction factor for the lesion ratio estimate that is calculated as more fully described below. As is known to those skilled in the art of pattern classification, a classifier algorithm is a method of separating a mixture of items into separate classes, usually based on a "feature vector," which is a list of numbers representing measurements of those items. A feature vector is a list of measurements of "features", where a feature is something thought to be useful in discriminating two or more classes. In the case of melanoma detection, the classes may include, for example, presence or absence of dark structures, or presence or absence of melanoma. Classifier algorithms can be linear or non-linear. They include linear classifiers, tree-based algorithms, and neural networks.

The method for identifying a border between a skin lesion and surrounding skin can also comprise histogram analysis of objects resulting from a watershed algorithm with the analysis being for the purpose of determining which of the objects will be merged into the lesion area. The term "object" as used herein refers to a group of adjoining pixels with similar luminance in the original image, and which can appear as an isolated structure at some stages of the watershed algorithm. A "watershed algorithm" is an algorithm as depicted in FIG. 4 and more fully described hereinafter for identifying the borders of a lesion on a digital image of the lesion. The term "object" as used herein also refers to a group of adjoining pixels with similar luminance in the original image which can appear as an isolated structure of any algorithm, including the DullRazor™ digital hair removal algorithm (Lee97) or modified digital hair removal algorithm of this invention.

Another aspect of this invention provides a method of identifying nonskin and nonlesion objects on an original digital image of a skin lesion comprising (a) analyzing image with a first digital hair removal algorithm, which may be the DullRazor™ algorithm or the modified digital hair removal algorithm of this invention; (b) locating lesion borders on the original image; and (c) applying a second, modified digital hair removal algorithm to the original image in which lower thresholds for noise are implemented outside the lesion border than inside the lesion border, which means more small noise is identified outside the lesion border. The border is determined by a binary border image as more fully described hereinafter. The DullRazor™ algorithm previously known to the art has a major drawback in that in addition to identifying "noise" objects, it also identifies the pigment network of the lesion as a noise object. By using a higher threshold for noise inside the lesion border, this problem is alleviated.

A pigment network is a network of brownish interconnected lines over a background of tan diffuse pigmentation (Argenziano03). Typical pigment networks are light- to dark-brown networks with small, uniformly spaced network holes and thin network lines distributed more or less regularly throughout the lesion and usually thinning out at the periphery (Argenziano03). Benign pattern variants can include peripheral accentuation in a ring, which can be patchy but still largely symmetric. In facial skin a peculiar pigment network, also called pseudonetwork, is typified by round, equally sized network holes corresponding to the pre-existing follicular ostia (Argenziano03). On the skin of the palms and soles, the pigment network normally follows the tiny sulci (grooves) in the dermatoglyphics (fingerprints).

The modified digital hair removal algorithm also comprises determination of an adaptive morphology threshold instead of the fixed threshold used in the original algorithm, as more fully described hereinafter.

The modified digital hair removal algorithm also comprises an area filter to remove objects that are smaller than a selected number of pixels. This modified digital hair removal algorithm can be adjusted for sensitivity by selecting thresholds having the highest signal-to-noise ratio, and highest hit ratio, where hit ratio is the ratio of hair area found to total true hair area.

In one embodiment of this invention, the hair mask of the DullRazor™ algorithm has been modified by the addition of an algorithm for identifying unusual hair width. The hair mask is iteratively dilated by a single unit until there is no significant change in the number of pixels present with a luminance below the median of luminance of the pixels within the hair mask, thereby arriving at an adequate hair mask for unusual hair width. A "significant change" in this context means a change that exceeds a threshold that is typically 0.40× the difference obtained in the preceding step, with a range for the constant that depends on lighting and darkness of hair, no greater than about 0.60 and no less than about 0.20.

In an embodiment of this invention, the modified digital hair removal algorithm comprises detection of bubbles by an algorithm for detection of salient points embodying an optimized minimal luminance threshold.

In another aspect, this invention provides a method of identifying structures that discriminate malignant melanomas from benign skin lesions on a digital image of a skin lesion comprising: (a) detecting dark structures on the image, and assigning numerical values representative of measurements of these structures for input into a classifier algorithm; and (b) running the classifier algorithm to identify said structures that discriminate malignant melanomas from benign skin lesions. The dark structures can be detected by a method comprising calculating crisp thresholds for inclusion of pixels of the image within the structures. Crisp thresholds are those thresholds that can be represented by a single real number. In a crisp set, unlike a fuzzy set, an object is either a member of the set or it is not. Crisp thresholds are never fuzzy. A fuzzy set is a set with an associated membership function, with the output of that function ranging from 0 to 1, inclusive. The output of the membership function is called the grade of the element. A membership function is a function associated with a fuzzy set, with the input being any element and the output ranging from 0 to 1, inclusive.

Dark structures are comprised of pixels within skin lesions with specific colors. Some colors have a higher degree of association with dark structures within the same skin lesion and in different skin lesions. The concept of a fuzzy set for the color of pixels within dark structures is to represent the degree of association of different colors within those dark structures using a membership function for the fuzzy set to quantify the degree of association of the different colors within the dark structures, with 1 typically representing the highest degree of association of membership in the fuzzy set and 0 typically representing no degree of association in the fuzzy set. Colors not present in dark structures would have a membership value of 0 in the fuzzy set.

In practice, dark structures can be detected by a method comprising calculating fuzzy indices to determine thresholds for inclusion of pixels of the image within said structures. The method of calculating fuzzy indices can comprise selecting optimal alpha cuts. An alpha cut is a crisp set containing all elements of a fuzzy set B that have membership grade≧alpha, where alpha is a real number between 0-1, inclusive (Klir88) A low alpha cut implies inclusion of low-grade members; a high alpha cut includes only high-grade members. High-grade members of a set are those for which the membership function value is high (greater than, say, 0.7); low-grade members of a set are those for which the membership function value is low (less than, say, 0.3). A crisp set, usually just called a set, is a collection of objects often called elements or members. The members of a set can be anything, including numbers.

Dark structures can also be detected by a method comprising analysis of a local area drop histogram. A local area drop used in determination of dark structures (globules, dots) is the drop between the average brightness or luminance of all pixels within the structure and the average brightness or luminance of all pixels within a specified neighborhood of a candidate structure, excluding the pixels of the structure. A local area drop histogram is the histogram over all candidate dark structures of the local area drops.

Dark structures can be given ratings on one or more scalable indices selected from the group consisting of eccentricity, closeness to periphery of the structure, total area of the structure, area of the structure relative to the area of the lesion, total number of structures, shape irregularity, clustering, structure color, structure brightness variance, and melanoma color index. A scalable index has no dependence upon size or magnification. It has no dimensions of measurement and may be considered dimensionless. For example, an index that identifies a fraction of a given lesion will identify the same fraction on a similar index for a lesion that has the same features but is x times larger (scaled up by a factor x). These scalable indices are input into a classifier algorithm to distinguish benign structures from malignant lesions.

Another scalable index useful for this purpose is the color clustering index, determined by a ratio obtained by dividing a numerator by a denominator as follows: The numerator is obtained by summing over each pixel in the entire lesion the number of pixels within a neighborhood of that pixel that have at least a selected alpha cut (level of membership in the fuzzy set of benign relative colors). The denominator is obtained by summing all neighbors that have nonzero membership (any degree of membership of the fuzzy set) of the fuzzy set of benign relative colors. The claim also applies to a color clustering index obtained by using the fuzzy set of malignant (melanoma) relative colors to replace the benign relative color sets as noted above, to obtain a numerator and denominator as above.

Other scalable indices useful for this purpose are atypical pigment network indices. An atypical pigment network can be any of a variety of pigment networks with brown, black or gray lines with irregular holes and thick lines over a background of tan or gray diffuse pigmentation. The darkness of the lines may make the atypical pigment network area the darkest in the lesion (FIG. 32). In other cases, the pigment network area is detectable by the different widths of the holes and thickness of the lines and not by darkness of the atypical pigment network region (FIGS. 33 and 34). For the purposes of melanoma detection, we include branched streaks (smaller regions to the right, FIG. 33) as an atypical pigment structure. We also include streaks at the rim of a lesion as atypical pigment network. These streaks at the rim of a lesion have been previously described separately as pseudopods and radial streaming, but are now combined into the one term: streaks (Argenziano03). They are bulbous and often kinked or finger-like projections seen at the edge of a lesion. They may arise from network structures but more commonly do not. They range in color from tan to black.

The four atypical pigment network indices are determined by ratios obtained by dividing a numerator by a denominator as follows: The lesion is divided in n×m blocks, for example 41×41-pixel blocks, each of which is at least partially within the lesion boundary, and four standard Haralick texture measures, with Haralick texture measures as defined in (Haralick73), determined as in (Umbaugh05). The texture measures here are taken over the co-occurrence matrix, with a distance of 20 (range 6-26) as defined in Haralick73, as applied in CVIPtools (Umbaugh05). Haralick noted that four directions are used: 0 degrees, 45 degrees, 90 degrees and 135 degrees. (Haralick73) With the modified method used in CVIPtools, the data from all 8 directions, 0-315 degrees in 45-degree increments, is obtained, but the data from 0 and 180 degrees, 45 and 225 degrees, 90 and 270 degrees, and 135 and 315 degrees are combined. This method yields good separation of malignant and benign classes, as below. It is likely that further combinations and simplification can yield good texture separation.

Correlation average, inverse difference average, texture entropy range, and correlation range are determined from each co-occurrence matrix. The n×m blocks may be contiguous, if the image is divided into blocks, or overlapping, sometimes termed the sliding window method. Using either method, texture determinations are made to construct the co-occurrence matrix for the entire lesion. Texture-based segmentation, also called texture segmentation, proceeds, accomplished using watershed or a similar segmentation method. Segmentation is done for an image of an optimized linear combination of the texture measures to calculate the "optimized texture luminance" feature. A limitation may be placed on the total segmented area, for example 20% of the lesion area, as we have found that a practical limit on the atypical pigment network area is 20%. The principal components transform (PCT) or independent histogram pursuit (IHP) may be used to compute the optimized texture luminance feature. The texture segmentation may be repeated multiple times, to determine multiple separate segmented areas, with the option of a limitation being placed on the maximum segmented area, as described above. If PCT or IHP histogram analysis indicates insufficient difference between optimized texture luminance on the segmented area and the remainder of the lesion, segmentation is not repeated. The numerator of the correlation average is obtained by computing the correlation average within the texture-segmented lesion area. The denominator is obtained by computing the correlation average over the entire lesion, or as an equivalently effective method, over the remainder of the lesion. The remaining three indices are computed as for correlation average, using inverse difference average, texture entropy range, and correlation range. These indices may be used as classifier inputs. In addition, other scalable indices, including eccentricity E, irregularity I and eccentricity area ratio R may be used as classifier inputs.

For 79 dysplastic nevi with a typical proportion (1 in 8) of dysplastic nevi with atypical pigment network, and 28 melanomas with atypical pigment network as the most visible feature, all lesions taken from the CD in (Argenziano00), 96.3% of all lesions were classified correctly, with 100% of melanomas classified correctly, using a Bayes classifier with default settings. The Chi-square attribute evaluations were: correlation average, 85.0418, inverse difference average, 83.8602, texture entropy range, 62.3315, and correlation range 45.7011. Other classifiers gave similar but slightly lower results. For example, the J48 decision tree, using only the correlation average, gave a classification accuracy of 93.5%, indicating the power of these texture features, using this ratio method, to detect atypical pigment network and discriminate melanoma from dysplastic nevi.

Salient point indices are also useful as input into the classifier algorithm to distinguish malignant lesions. Salient point indices are determined over one or more deciles (for example the outer decile) of the lesion over K×L blocks, where the block size is typically 27×27, but can extend over a larger range, for example from 23 to 39. The method must first eliminate large dark structures (blotches), telangiectasia, bubbles and hairs. The intensity image and a sigma of 1.02 (range 0.98-1.10) is used for salient point detection but similar results may be obtained with other combinations of image planes and sigma. An intensity image (of an original color image) is defined for each pixel of the intensity image (similar to the luminance image) as R/3+G/3+B/3, where R, G, and B are the red, green and blue values of a pixel in the original color image.

The salient point statistics are computed over rectangles of size K×L, where K and L are integers; typically K and L are optimized at 27, but can range from 23 to 39. The first six variables are computed: block mean, median, and standard deviation, and each of these divided by the average intensity for the block. A seventh variable is the standard deviation over the block times the square of the average intensity of the block. The average of these seven variables, confined to blocks on the selected lesion decile or deciles, are used as input by a classifier. "Lesion decile" refers to an area comprising 10% of the total lesion area. Starting at the lesion border and working inward, the first or outer decile is the 10% of pixels closest to the border, and the $10^{th}$ or inner decile is the 10% of pixels furthest from the border and closest to the center.

Border gradient indices may also be input into the classifier algorithm to distinguish malignant from benign lesions. Border gradient indices are determined using the lesion border and the lesion centroid, operating upon a plane computed from the color planes, typically the intensity or luminance plane. The gradient in the direction from centroid to the border is computed after averaging about 3 to about 19, and typically about 5 points at the border and about 3 to about 19, and typically about 5 points at a second location X pixels outside the border in the direction from the centroid to the border, where X is typically 50, but can vary from about 15 to about 150. The gradient may be taken as a sample at every Y points (Y is typically about 32), or continuously. A histogram of gradients may then be split at an interpeak mean into two or more sets of border points, and the number of elements in the two sets of border points with the highest and lowest mean gradients, normalized by the number of border points (excluding image edge points), is computed. The total number of such sets is retained. The normalized high-gradient fraction of border points is called the high-gradient fraction. The normalized low-gradient fraction of border points is called the low-gradient fraction. The Euclidean distance between the centroid of the high-gradient fraction and the lesion centroid, normalized (divided) by the square root of the lesion pixels, with this normalized distance called the high-gradient fraction eccentricity, is computed. If the high-gradient eccentricity is sufficiently high, a melanoma is more likely. If the high-gradient fraction is 0.2-0.6, and the high-gradient fraction's mean gradient is sufficiently high, a melanoma is more likely. The high-gradient fraction, high-gradient mean, low-gradient fraction, low-gradient mean, number of sets of border points, and high-gradient fraction eccentricity are saved and used as inputs to a classifier.

BRIEF DESCRIPTION OF THE FIGURES

FIG. 5A shows an example of watershed lines (peaks shown by arrows pointing down) and basins (valleys shown by arrows pointing up). FIG. 5B is a three-dimensional representation of the basic rainfall model used in watershed segmentation.

DETAILED DESCRIPTION

Figure 1:
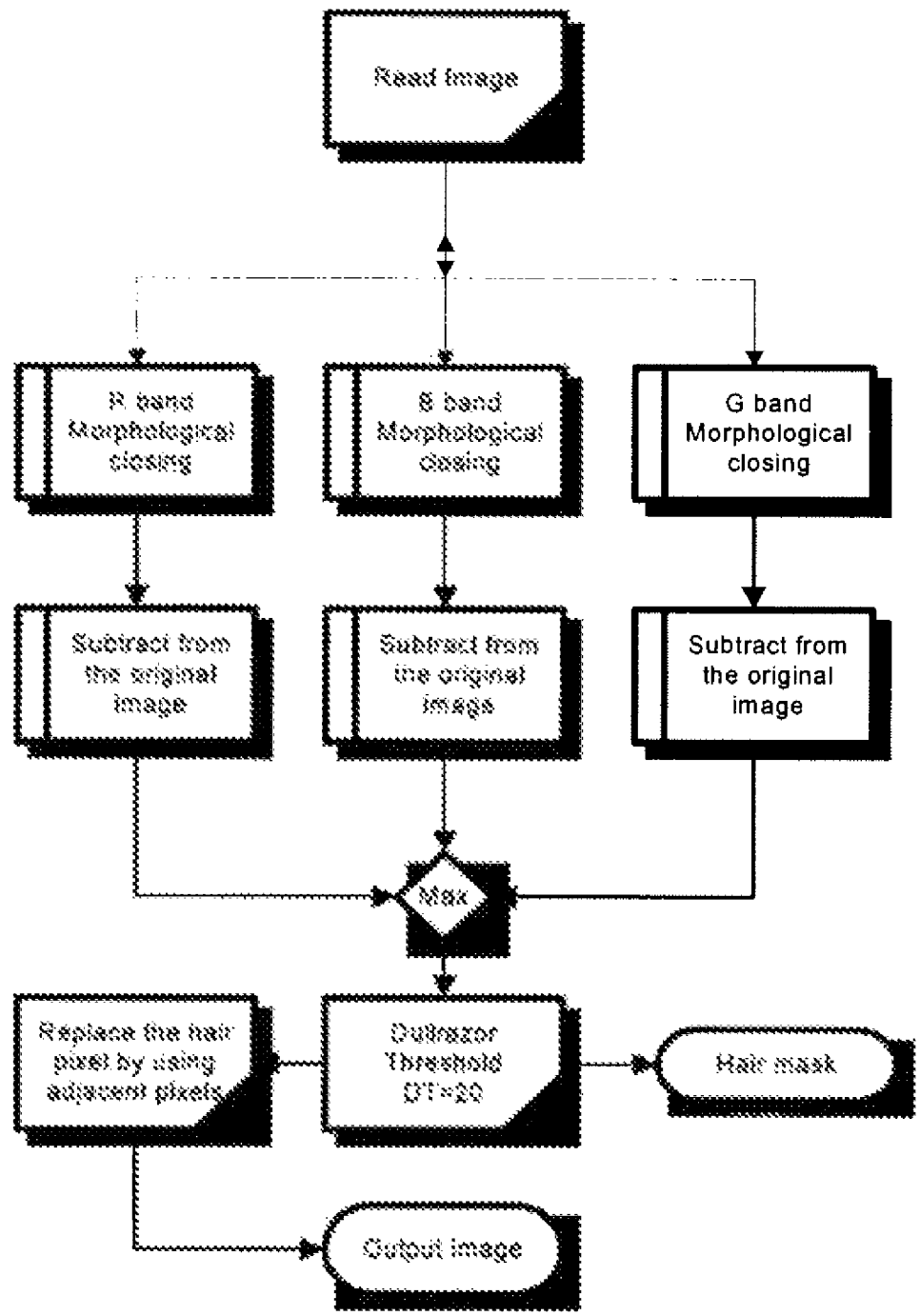
FIG. 1 is a flow chart showing the prior art DullRazor™ algorithm for identification and removal of hairs on a lesion image.

This invention provides a method of processing a digital image of a skin lesion suspected of being a melanoma to achieve diagnosis or biopsy decision automatically using algorithms on a digital computer. The method involves providing an image using visible light reflected from the lesion to the processor, for accurately segmenting out (finding the borders of) the lesion. The image should comprise at least about 512×480 pixels.

The method of this invention performs preprocessing to remove unwanted portions of the image including hairs, bubbles, flash, shadow, markings such as ink, measuring scales and devices, and telangiectasia, then identifies critical features including statistics of peripheral salient points, border sharpness, and the proportion of colors consistent with melanoma as well as critical structures including regular and irregular pigment network, scar-like depigmentation, granularity, peripheral and eccentric blotches, peripheral and eccentric globules, peripheral and eccentric dots, peripheral blush, single, pairs, and groups of colors consistent with melanoma, and concentric-ring quantized eccentric melanoma color.

The segmentation method for identifying the lesion border involves a sequence of preprocessing including removing hairs, flash, shadow and other extraneous unwanted portions of the image noted above, before a watershed method is applied, and applying an optimized histogram and color statistic processing method to obtain an optimized lesion ratio estimate as input to a flooding variant of the watershed algorithm, followed by classifier optimization and smoothing operations using, for example, a second-order spline function followed by a distance transform operation to remove unwanted peninsulas. Bubble detection uses a combination of salient points, brightness thresholds and an automatic rim-finding method. The regular and irregular pigment network identification involves optimized digital texture analysis routines which include Laws energy filter operations (Laws80) and grey-level correlation matrix correlation average and range, inverse difference average, and entropy range analysis. (The four best features were correlation average and range, inverse difference average, and entropy range.) Scar-like depigmentation and granularity determination use the methods of Tatikonda (Tatikonda02) that are modified by parameters describing size and location of scar-like depigmentation and granularity, proximity of the two features, and Melanoma Color Index determination for scar-like depigmentation. Irregular vessels are found using a modified telangiectasia finder.

These operations are specified for visible-light images, such as those obtained by xenon flash as with the Dermaphot (Heine, Munich, Germany) or Epiflash (Canfield, Fairfield N.J.) or with LED rings (3Gen Imaging, Dana Point, Calif., FotoFinder Teachscreen Software GmbH, Bad Birnbach, Germany). The methods of this invention are performed using a computer processor such as a personal computer.

The image analysis is combined with clinical features which are obtained and input to the system, including: patient age, gender, lesion location (face, ears, scalp, neck, arm, leg, trunk, anogenital, hand, foot), childhood sunburns, recent lesion onset/change, family history of melanoma (first degree relative), and personal history of melanoma.

The following provides a detailed explanation of the method and order of operations:

The processor receives visible light images of a lesion on a patient's skin that is suspected of being a melanoma from any source of such images, including xenon flash as with the Dermaphot (Heine, Munich, Germany) or Epiflash (Canfield, Fairfield N.J.) or with LED rings (3Gen Imaging, Dana Point, Calif.) or partial LED rings (FotoFinder Teachscreen Software GmbH, Bad Birnbach, Germany).

The processor then computes the patient's background skin color. In order to do this, areas of the image that are not skin are first eliminated according to nonskin color elimination criteria, including black or white borders, measuring scales or measuring devices such as rulers (often a ruler or scale is included in the photograph so indicate the size of the lesion) on the images, or reflections from bubbles. These features are omitted, i.e., are not considered in subsequent processing by using three criteria for normal skin: $R>90$, $R>B$, $R>G$, to eliminate dark noise and shadows and nonskin, AND $R<250$, $G<250$, $B<250$ to eliminate flash and bubbles, where R, G and B denote the red, green and blue intensity values, respectively, of the pixel under consideration. This method is modified from McLean94. An alternate screening has been used successfully to eliminate dark borders. This screening eliminates dark borders by requiring $Max(R,G,B)>60$. The rules above also ensure that dark borders are eliminated.

Areas of the image that represent hair on the skin are also identified and eliminated. A modified digital hair removal algorithm is used. The DullRazor™ (Lee97) has proven to be a useful algorithm for dermoscopy image segmentation. The algorithm can generate reliable detection and elimination of pixels representing dark hair from consideration in analyzing the image.

Two problems concerning hair detection have emerged. The DullRazor™ digital hair removal algorithm will miss fine hairs and sometimes erase critical intralesional structures within the pigment network. A solution for these problems can be found by preprocessing which includes applying an adaptive threshold for grayscale morphological closing, using an area opening filter, and applying noise removal strategies.

The DullRazor™ algorithm is a morphological closing-based method, as is known to those skilled in the art of image processing (Soille03), which consists of eight major steps. The flowchart depicted in FIG. 1 shows the sequence of operations:

Read the color image.
Apply the morphological closing structures to each of the three bands of the image and keep the maximal value.
Subtract the original band from each band of the resulting image of the last step.
Combine the three resulting bands by choosing the maximal value of the pixels.
Apply the threshold to get rid of most of the noise.
Generate the hair structure.
Replace the hair pixels using bilinear interpolation of adjacent pixels.

Generate the hair mask and the resulting image.

The modified digital hair removal algorithm of this invention provides five major improvements: use of a relative threshold instead of a fixed threshold, with different thresholds inside and outside the lesion, an area filter and other modifications for noise removal, sensitivity adjustment, and adaptive digital hair removal algorithm threshold estimate, as discussed below:

Relative Threshold

The improved digital hair removal algorithm uses an adaptive morphology threshold instead of the fixed threshold in the original algorithm. The new algorithm quantizes the result of the gray-level morphological closing to [0, 1] and limits the threshold to be a percentage of the maximum pixel value calculated from the image in the resulting image.

$$\eta = \max(p_{ij} \epsilon I_{close}) \times 80\%$$

$\eta$: threshold value $p_{ij} \epsilon I_{close}$: pixels in the morphological closing result Instead of using the fixed threshold used in the original DullRazor™ algorithm (prior art), we are using a new threshold $\eta$, which is calculated as follows. Of all the pixels resulting from the morphological closing operation after being quantized to the range [0,1], the maximum value is found of all these pixels. The new threshold (replacing the fixed threshold used in the original DullRazor™) is set to 80% of this value. This range may vary from 65% to 95%.

Noise Removal

Empirically, almost all the hair will either cross the lesion border or be totally outside the lesion area. So a literal rule is defined that all hair candidates strictly inside the lesion boundary will be considered noise and discarded. Different thresholds inside and outside the lesion will be later defined, such that the inside threshold is higher than the outside threshold to remove more noise from outside the lesion area. The digital hair removal algorithm threshold is set loosely for the first iteration, so that fewer hairs are removed inside and outside the lesion (because a single threshold must be used on the first iteration of the digital hair removal algorithm as the border is still not determined). This results in some pigment network being erased, but this is satisfactory for the first digital hair removal algorithm output, which is only used for border determination.

Area Filter

Figure 2:
FIG. 2A shows an original image of a lesion.
FIG. 2B shows the hair mask for the same image after application of the digital hair removal algorithm to remove pixels representing hair (the hair mask represents the pixels identified by the digital hair removal algorithm as hair that will be removed by this algorithm)
FIG. 2C shows the hair mask for the same image after application of an area filter to remove noise in the form of pixels representing blobs that are smaller than a certain number of pixels.
Figure 2:
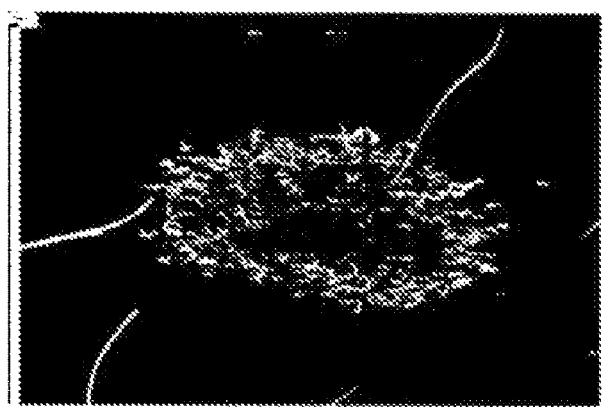
Figure 2:
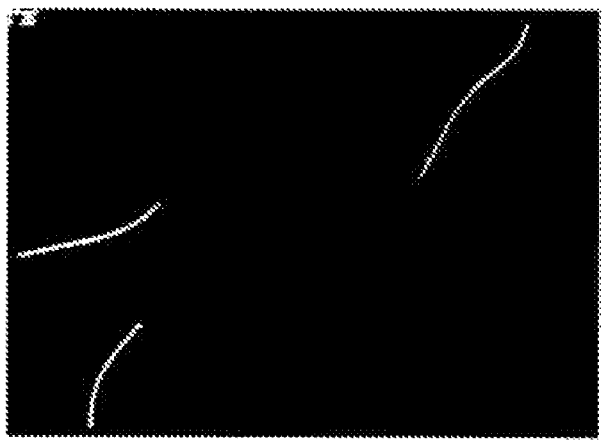

An area filter to remove the blobs that are smaller than a certain number of pixels has proven to be a very useful strategy to suppress the noise. FIG. 2 shows the results before and after the area filter.

Sensitivity Adjustment

To adjust the sensitivity of the algorithm, we present the method below.

Define $I_c$ as the result of grayscale morphological closing $$I_T = \sum_{p \in I_c} (p > \eta) \quad \eta \text{ is the dullrazor threshold}$$

$I_c$ is the image resulting after grayscale morphological closing. $I_T$ is the thresholded digital hair removal algorithm image.

Practically, the threshold varies from 0.03 to 0.08. At a value of 0.1, almost all segmentation, that is, separating out the lesion, will be eliminated. When the threshold is too low, noise will be overwhelming. To view the effect of different thresholds on the image, we define an array to store the different values from 0.01 to 0.1, and the histogram of the number of objects with same area (same number of pixels) is defined by:

$$H_i = \sum_{P_i \in I_T} \Psi(P_i) \quad P_i \text{ is } i^{th} \text{ object in the image, } i = 1, 2, 3 \ldots$$

Binary function $\Psi_i$ is given by $$\Psi_i(P_i) = \begin{cases} 1 & \text{if } \sum_{p \in P_i} p = i \\ 0 & \text{otherwise} \end{cases}$$

Adaptive Digital Hair Removal Algorithm Threshold Estimate

A standard hair mask is introduced in the algorithm to estimate the optimized threshold point for morphological closing, and an area filter to remove objects less than a certain size. Thresholds are determined to have highest (SNR). Practically, the range of morphological closing is between 0.03 and 0.08, the range of the area filter is between 60 and 400. Fifty values of the former threshold and 50 of the latter threshold are chosen and their combinational SNR are calculated (2500 combinations). Inner thresholds of 2, 3 and 4 times the outer threshold are computed. An error surface is generated to determine the global maximum.

Figure 3:
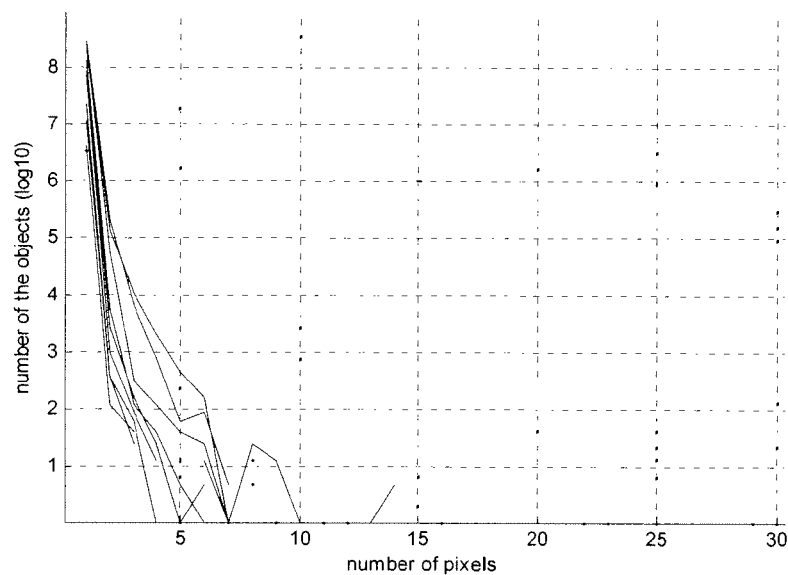
FIG. 3A is a graph showing the number of noise objects in an image as a function of number of pixels in the object graphed for a small number of images.
FIG. 3B is a graph showing that signal-to-noise ratio (SNR) is a function of both morphological closing threshold and object size thresholds.
FIG. 3C graphs the hit rate which is the percentage of the hair that is picked up by the algorithm as a function of morphological closing threshold and object size thresholds.
Figure 3:
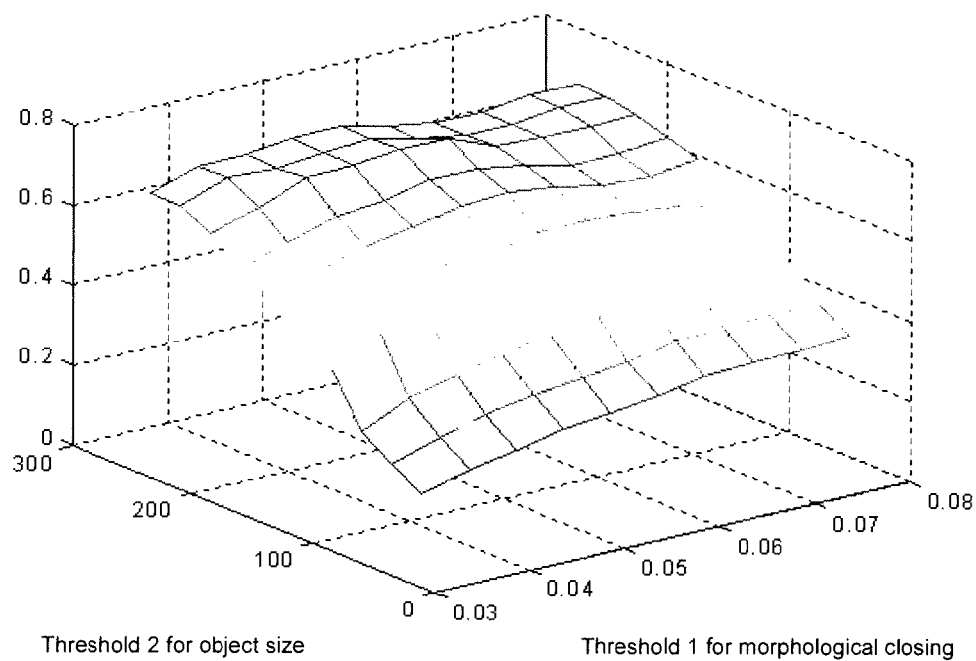
Figure 3:
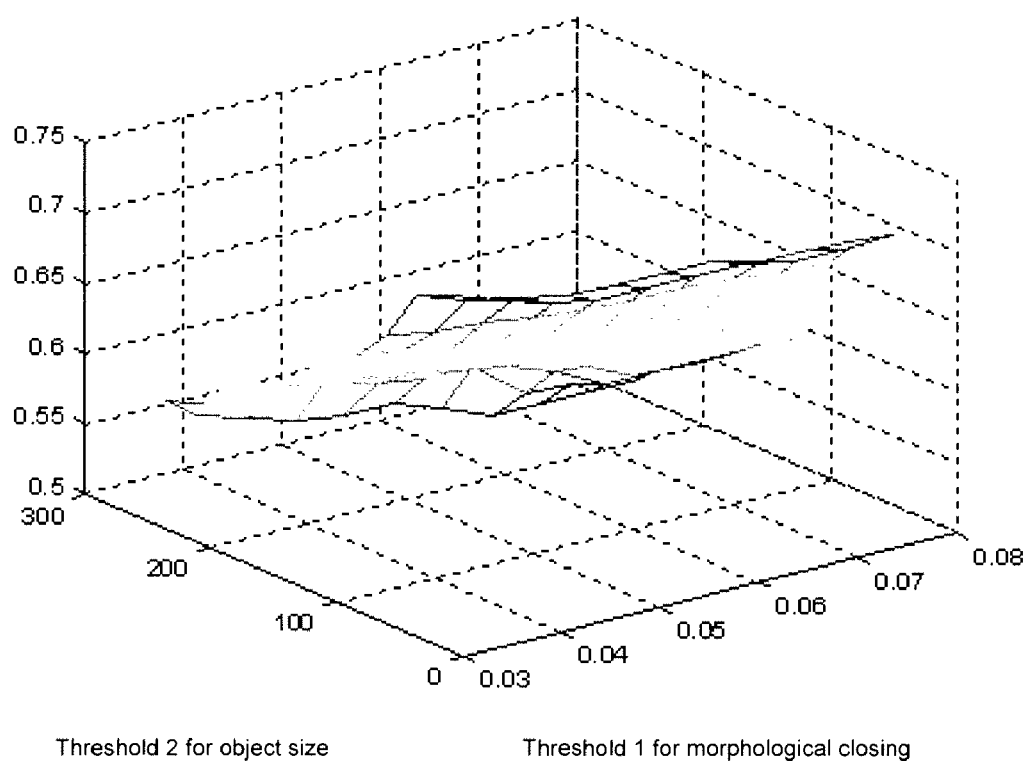

Lesions have an inverse relationship between size of noisy object and number of noisy objects of a given size, as shown in FIG. 3A.

Signal-to-Noise Ratio (SNR)

The signal-to-noise ratio is defined by the following equation for the binary (black/white) hair mask image. The SNR is an important measure to estimate and evaluate image processing procedures during the hair removal process. Noise is comprised of small noise, which is easily removed by object size thresholding below, and large noise, which is either 1) a false addition to a true hair mask or 2) a large object that is incorrectly found. For good results, the noise counted in the noise total may be restricted to large noise, of type 2) (large object incorrectly found). FIG. 3B shows that the SNR is a function of both morphological closing threshold and object size thresholds. The SNR is given by:

$$SNR_{hair} = 20 \times \log_{10}\left(\frac{\text{Power (hair)}}{\text{Power (white pixel)}}\right)$$

$$= 20 \times \log_{10}\left(\frac{\sum_{i \in Hair} p_i}{\sum_{j \in NH} p_j}\right)$$

(NH is the set of no hair and $p_i$ and $p_j$ represent pixels that are summed for pixel counts.)

Hit Rate

Signal-to-noise ratio represents to some degree the quality of the hair mask. However, in some cases, we are mostly interested in how many hairs can be detected by the algorithm. Therefore, in some cases, it can be important to keep most of the hair while allowing limited noise. A hit rate is introduced to measure the percentage of the hair that is picked up by the algorithm, as shown in FIG. 3C.

$$\gamma = \sum_{p_i \in I_{hair}} p_i \bigg/ \sum_{p_i \in I_{all}} p_i$$

Granularity

The granularity of the image could be defined in multiple ways. In our experiment, the first approach is to define the granularity of the image as the power of the resulting image of the morphological closing. The equation is given below.

$$\phi = \sum_{p_i \in I_c} p_i / size(I_c)$$

For this equation only, $p_i$ refers to the luminance or equivalent pixel gray-scale value rather than the pixel count as in the equations above. $I_c$ refers to the area of the hair found after morphological closing. Experiments showed that the improved digital hair removal algorithm can generate more reliable hair masks with much less noise in the hair mask, while preserving the most important features, such as pigment networks and globules.

Hair Removal on First Iteration

The first modified digital hair removal algorithm implementation uses an adaptive morphological threshold and a single object size threshold optimized over SNR and hit ratios i.e., ratios of hair area found to total true hair area. The threshold of size of small objects removed is dynamic, ranging from 40 to 400 pixels, typically in the range of 200 pixels. Since no lesion border is known at this point, a second inside-the-border threshold is not used.

An estimation of hair widths is made. The digital hair removal algorithm hair mask width is iteratively dilated by a single unit using mathematical morphology until there is no significant change in the number of pixels below a median threshold, i.e., hair mask width is adequate, as a check on optimized hair finding using iterative morphologic dilation and the histogram of object sizes.

Segmentation (Finding Lesion Border)

Watershed Algorithm Border Detection

The watershed algorithm, which has many variations, is based upon a topographical representation of an image gray-level map. In the topographical representation, the brighter pixels represent the higher altitudes or the "hills" and the darker pixels correspond to the "valleys", which allows determination of the path that a falling raindrop would follow (Bleau00). Watershed lines are the divide lines of "domains of attraction" of water drops. The flooding modification of the watershed algorithm is analogous to immersion of the relief in a lake flooded from holes at minima. The flooding variant is more efficient than the original falling raindrop approach for many applications (Vincent91). With merging techniques, the watershed algorithm has improved performance and is now a primary tool for medical image segmentation (Bleau00).

The proposed watershed-based segmentation technique is compared to Pagadala's histogram thresholding method (Erkol05), the gradient vector flow method developed by Erkol et al. (Erkol05), and the modified JSEG method (Celebi06) on a set of 100 dermoscopy images.

Figure 4:
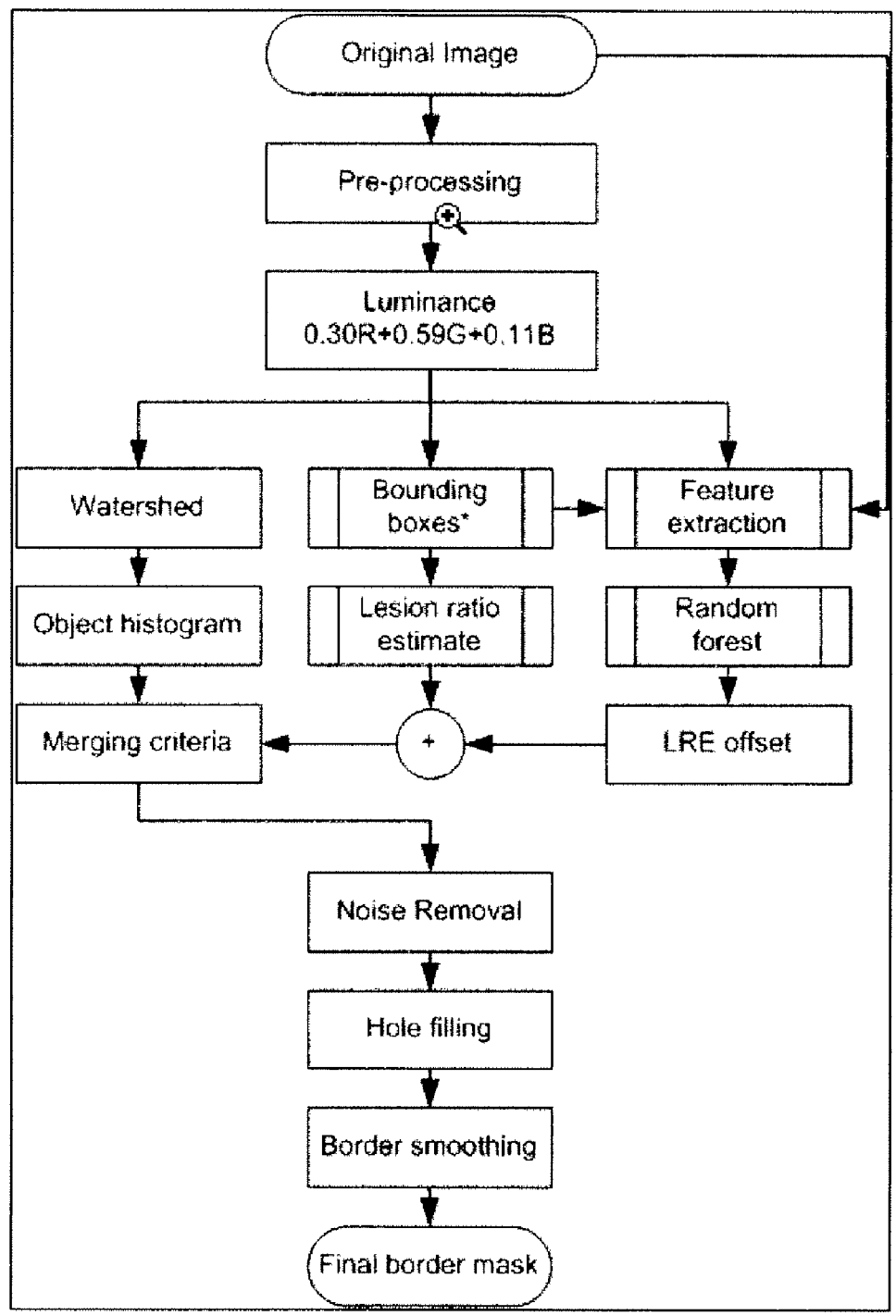
FIG. 4 is a flowchart showing the watershed algorithm we developed for detecting borders of a lesion. Note box with asterisk: If one or more bounding box sides are not found, the mean lesion ratio estimate with least mean square correction may be used to estimate the missing side(s). Alternately, this alternate lesion ratio estimate is then used rather than the bounding box lesion ratio estimate.

Watershed-Based Algorithm For Skin Lesion Segmentation: Overview of the Algorithm An overview of the watershed algorithm is shown in FIG. 4.

Preprocessing: Black Frame Cropping and Background Skin Finder

The watershed algorithm requires the non-skin finder and background skin color finder as above.

Watershed Transform

For a two-dimensional image, a three-dimensional representation is constructed from the original image, where x and y represent the row and column of the image pixels and z represents the luminance value. The methods of Gomez et al. (Gomez06) may be used to create a histogram pursuit (IHP) image as an alternate to the luminance plane. The IHP image multiplies the R,G, and B values by constants that maximize the depth of the valley between the histogram peaks for the image. (Gomez06)

Points belonging to a regional minimum or where water following the steepest path would fall into the same minimum are called catchment basins.

The sets of points where water in rainfall simulations will be equally likely to fall into more than one such regional minimum when performing a rainfall simulation are termed divide lines or watershed lines. A set of adjacent pixels with the same gray level is called a plateau.

The flooding version of the watershed algorithm is summarized as follows:

1. Rainfall simulation is used to determine regional minima by following raindrop paths until a regional minimum is reached. When the rainfall simulation starts from the point (x, y) with gray value I(x, y), its neighbor's gray value is given by I(x+i, y+j) where i, j=±1. The next rainfall path $\vec{R}_p$ is given by finding the maximum gradient (steepest path) of the gray value of the neighbors, which is given by the following equation:

$$E(x+i, y+j) = \nabla I(x+i, y+j) \; i,j=\pm 1.$$

Wherever the rainfall path reaches a regional minimum $(x_0, y_0)$ where $E(x_0+i), (y_0+j) > 0$, for i, j=±1, these regional minima become the flooding start points. We use the same label for the pixels in the rainfall path and the regional minima $$L(x, y) = L(x_0, y_0) \; x, y \in \vec{R}_p.$$

2. The flooding procedure is launched at a regional minimum. Rainfall simulations are repeated on all adjacent pixels to see if the points could reach the same regional minimum. If the regional minimum is reached, the neighboring pixel will be given the same label as the one with the regional minimum; otherwise, a new regional minimum will be pushed onto the stack for further flooding processing. The procedure stops when all regional minima in the stack are processed. As the waterline increases, more pixels beyond the regional minimum are flooded and given the same label.

Figure 5:
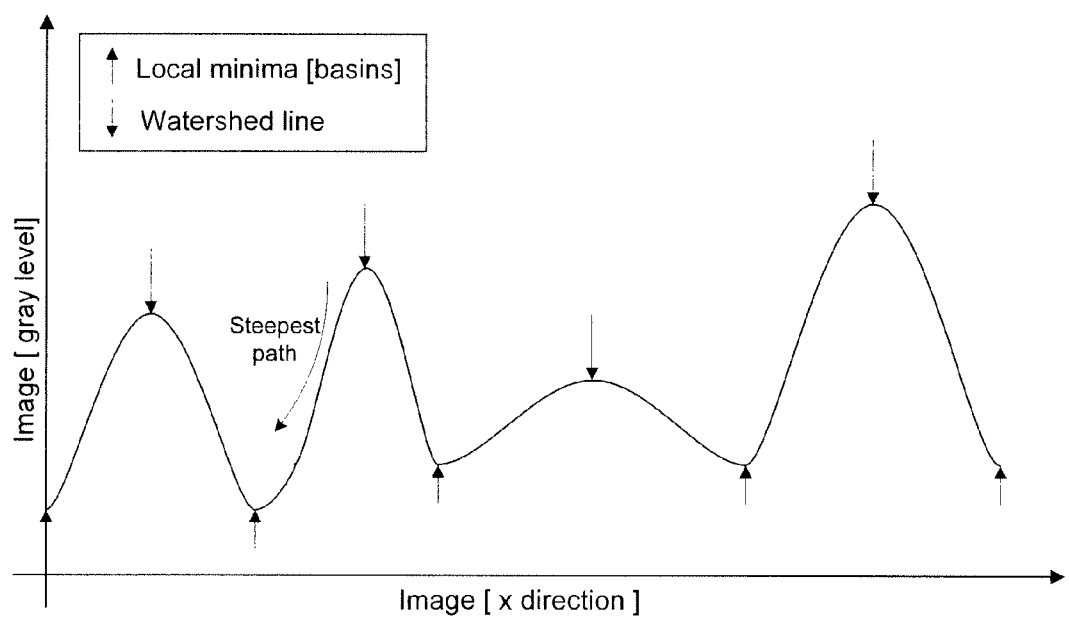
FIGS. 5A and 5B show two- and three-dimensional illustrations of the intermediate stage of the flooding process of the watershed algorithm.
Figure 5:
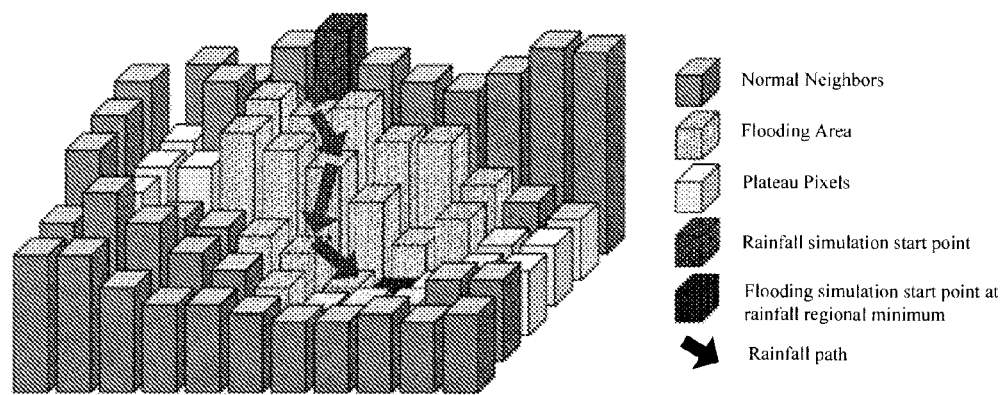

3. When the rising waters in different catchments are about to merge, a dam is built to prevent the merging. When the flooding procedure finally reaches the global maximum, the whole area is flooded except the dam boundaries, which correspond to the watershed lines. FIGS. 5A and 5B show two- and three-dimensional illustrations of the intermediate stage of the flooding process.

Over-segmentation and Solutions

Figure 6:
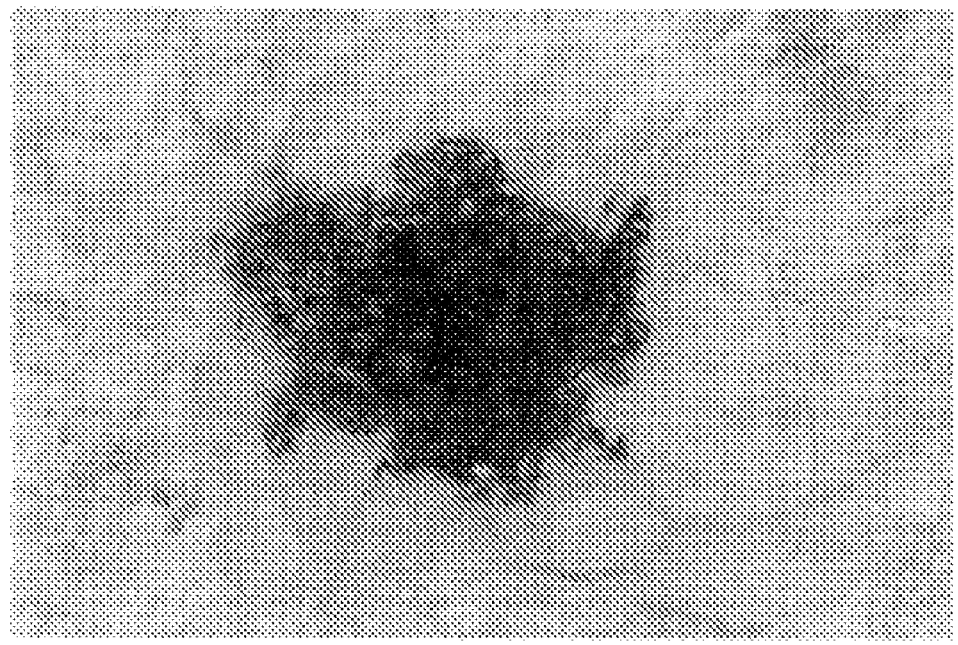
FIG. 6 is an example dermoscopy skin lesion image.
Figure 7:
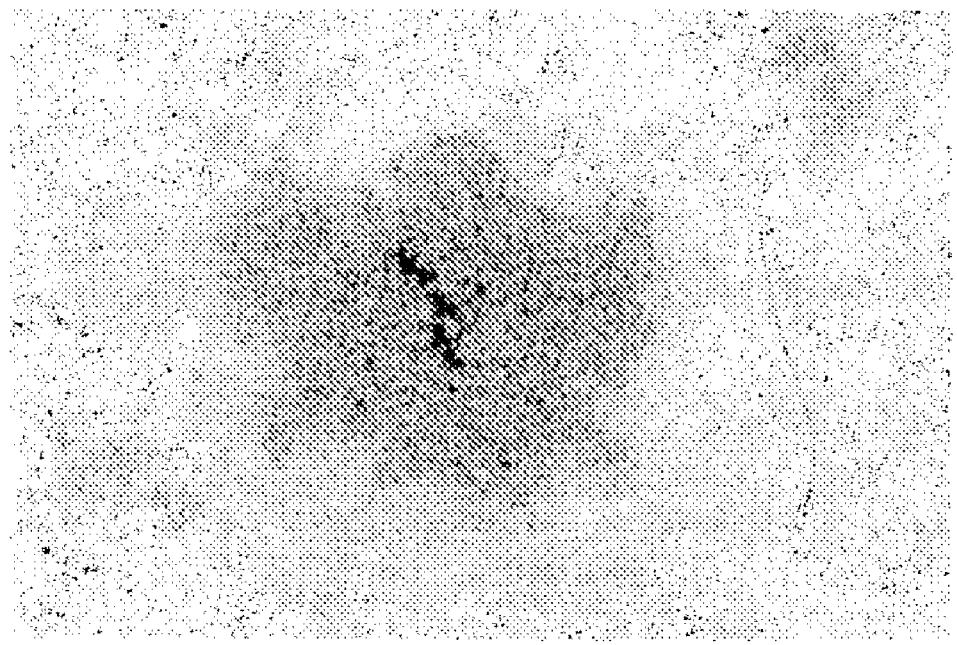
FIG. 7 shows the result of the watershed transform overlaid on the skin lesion image of FIG. 6 without any preprocessing.

Over-segmentation is the most common problem for the watershed transformation. Over-segmentation occurs because every regional minimum, even if tiny and insignificant, forms its own catchment basin. FIG. 7 shows the result of the watershed transform overlaid on the skin lesion image (FIG. 6) without any preprocessing. The solution that we have adopted is to use a merging procedure to prevent the over-segmentation. Other solutions include removing minima that are too shallow (Felke101), (Mangan98), and the h-minima transform (Soille03), that suppresses all regional minima whose depth is less than h, where h is an arbitrary threshold.

Modified Watershed Algorithm with Object Merging

Object histogram: The watershed algorithm that we are using applies a rainfall simulation to the grayscale luminance or any other single-plane image, such as the IHP image and to the blue plane of the image. From empirical analysis of the image set, the blue plane in general produced more accurate borders when compared to other planes. Other implementations can include a linear combination of the red, green and blue plane to maximize the area of the valley between histogram peaks (Gomez06).

Figure 8:
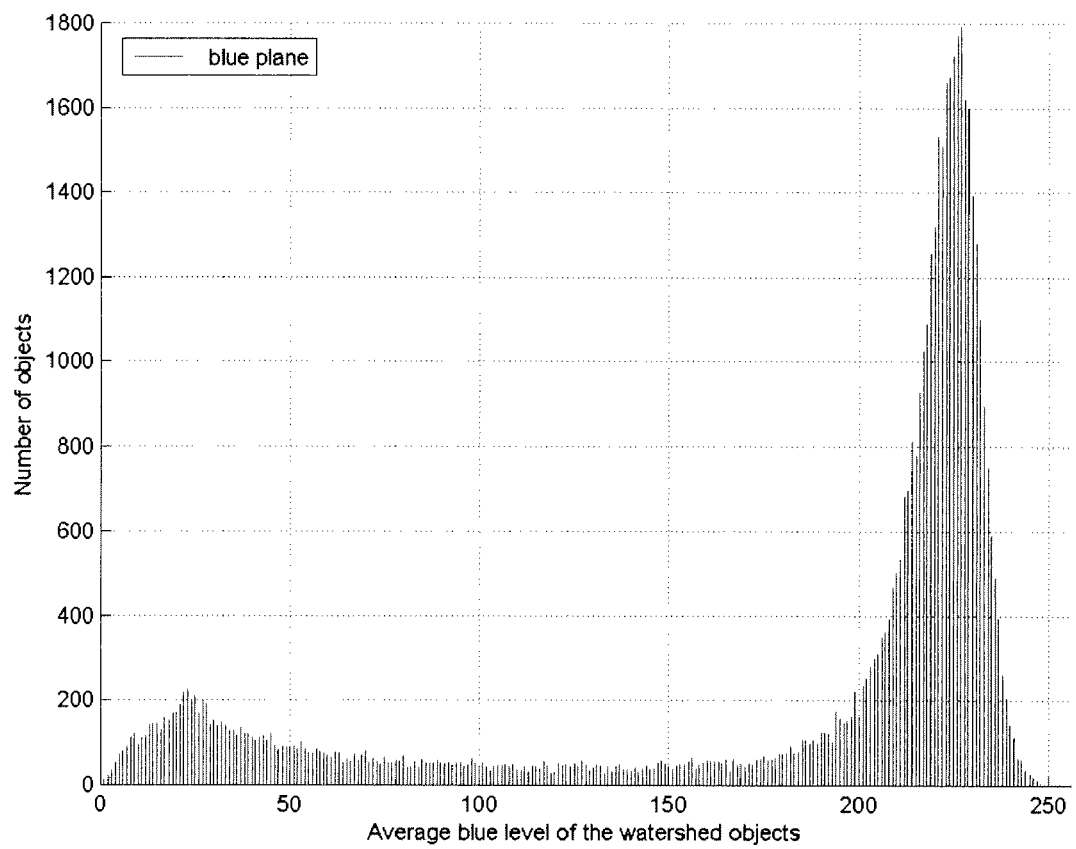
FIG. 8 shows the object histogram for a skin tumor image for the blue plane. The higher peak on the right represents the background or skin; the lower peak represents the lesion.

Objects in the watershed image are then tabulated in an object histogram, where each vertical line on the histogram represents the number of small objects (or segmented regions) in the watershed image (not pixels in the original image) with that average gray-level value on the horizontal axis. Histogram analysis of the image set reveals that most skin tumor images have two peaks in their histograms. FIG. 8 shows the object histogram for a skin tumor image for the blue plane. The higher peak on the right represents the background or skin; the lower peak represents the lesion.

Labeling and Merging

As stated in the previous section, a lesion image usually has two peaks in its histogram, the lower peak representing the lesion and the higher peak representing the skin color distribution. It is not always easy to locate the lower peak. However, the global peak, i.e., the highest peak in the histogram, is very easy to locate. A merging and labeling method is then developed to find the skin.

Figure 9:
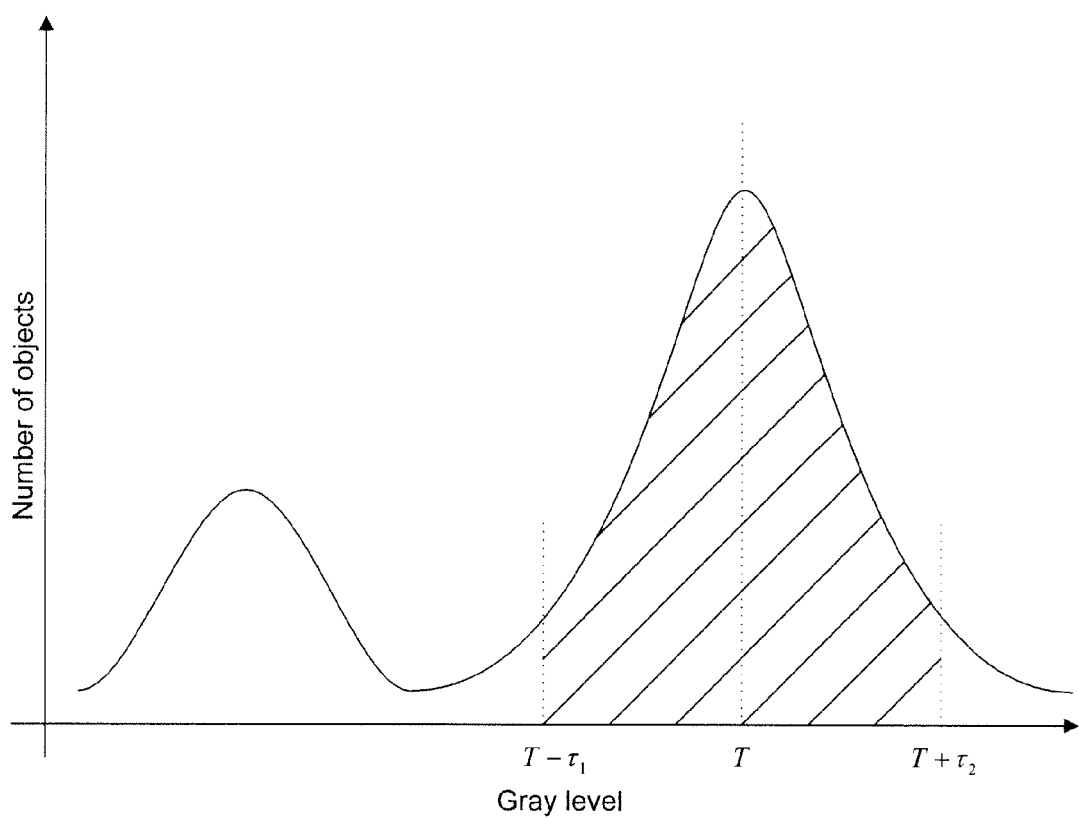
FIG. 9 shows Labeling and merging from the object histogram of FIG. 8.

The merging procedure is initiated by finding the maximum value in the object histogram (FIG. 9). Starting from the gray level T which marks the gray level with the maximum number of objects in the histogram, a recursive procedure expands in both directions on the x-axis of the histogram at the step size of one gray level in each direction. Usually, $T+\tau_2=255$, the maximum gray level, before the procedure ends, in which case $\tau_1 \neq \tau_2$. When the total area of the objects within the color range exceeds a certain portion of the image area, the procedure stops, and the lower limit and upper limit $T-\tau_1$ and $T+\tau_2$ are recorded. $S_x$ is the total area of the watershed segments with average color equal to gray level x.

$$\int_{T-\tau_1}^{T+\tau_2} S_x dx \approx (1-\gamma)M$$

Lesion Ratio Definition

The lesion ratio γ is the ratio of the lesion area to the image area M. From empirical analysis of the experimental image set, an estimate of 0.25 is typical for the lesion ratio. A more accurate lesion ratio estimate will be introduced in the following subsection.

The next step in the procedure is traversing the entire image and locating the objects. If the average color of an object is higher than the lower limit, $T-\tau_1$, a label of 0, representing the background (skin), is assigned to the object; otherwise, a 1 is assigned to the object. Therefore, all the objects are categorized into two groups: background skin and lesion.

Figure 10:
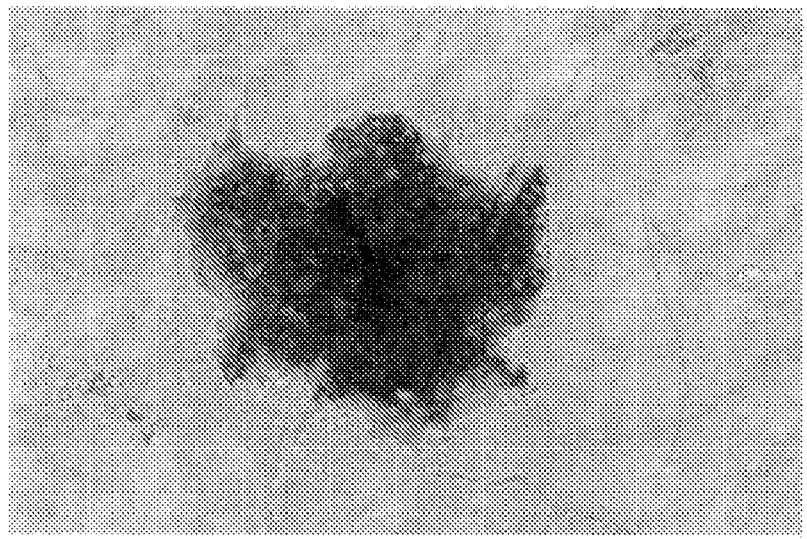
FIG. 10 shows the result of the merging procedure on the sample image using a fixed lesion ratio of 0.27, with a white outline indicating the borders of the detected regions.

FIG. 10 shows the result of the merging procedure on the sample image using a fixed lesion ratio of 0.27, with a white outline indicating the borders of the detected regions. The segmentation errors present at the stage of FIG. 10 are addressed in the following sections.

Lesion Ratio Estimate

Mean Lesion Ratio Estimate from Mean Luminance: Because the distribution of lesion ratios in our test set varies widely, ranging from about 5% to 48.4% on 100 images, we need an a priori estimate of the lesion ratio γ. The simplest estimate $\hat{\gamma}_L$ is obtained by counting the number of pixels with gray level value $I_{xy}$ less than the mean luminance μ, and dividing this by M, the total number of pixels in the image.

$$\hat{\gamma}_L = \frac{\text{count}(I_{xy} < \mu)}{M}$$

This formula tends to give too high an estimate for images with an actual low lesion ratio, and too low an estimate for images with an actual high lesion ratio.

The mean lesion ratio estimate is further improved by adjustment by a linear correction factor. Even after being adjusted by a linear correction factor, segmentation errors were still high. Various methods to obtain a better lesion ratio estimate were tried, including analysis of the histograms in each color plane and in the luminance image, and the use of an outer bounding box, as described in the next section.

Bounding Boxes

Figure 11:
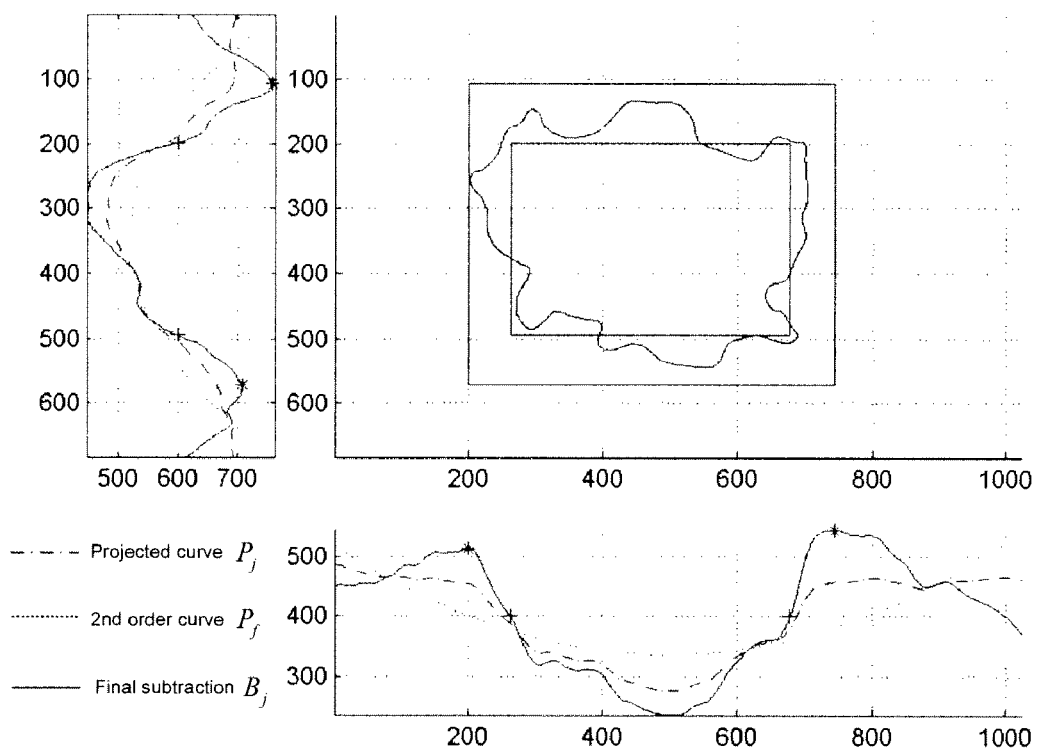
FIG. 11 shows an example of bounding box detection for the lesion shown in FIG. 6.

The projected outer bounding box, shown in FIG. 11, is calculated as follows: Each column of numbers representing the luminance image is projected (summed) vertically to form a vector ($P_j$). The second-order best-fit curve of this projection ($P_f$) is subtracted from this projection, the resulting curve is normalized as described later, and then the two major maxima (denoted by * in the figure) of the normalized curve ($B_j$) are found. These points define the horizontal extent of the outer bounding box. A similar procedure is used with the horizontal projection of the numbers representing the luminance image to define the vertical extent of the outer bounding box. The inner bounding box is found by the location where the normalized difference curve's ($B_j$) value equals the mean value of the second-order fitting curve ($P_f$) (noted by + in the chart). Two projections are needed to construct the four sides of the inner and outer bounding boxes. A more detailed description follows.

In order to estimate the lesion ratio, the bounding box area ratio is used. Let $I_{ij}$ be the luminance value of the $i^{th}$, $j^{th}$ image pixel, and n be the number of rows. The $j^{th}$ column projection point $P_j$ is given by:

$$P_j = \sum_{i=1}^{n} I_{ij}$$

Then a second-order best fit curve is calculated based on the projection curve. Since $P_j$ is an n-element array, $P_f$ is also an n-element array given by $$P_f = a_2 x^2 + a_1 x + a_0$$

The coefficient vector $[A=\alpha_2\ \alpha_1\ \alpha_0]$ is determined by minimizing the mean square error e between $P_j$ and $P_f$:

$$\frac{\partial e}{\partial a_i} = \frac{\partial}{\partial a_i} E\{|P_j - P_f|^2\}$$
$$= 0,$$

where E represents the expected value.

Use of a Subtraction Curve Applied to Horizontal and Vertical Projections for Bounding Box Determination The second-order curve is then subtracted from the original projection curve to create a curve that is roughly m-shaped. Some of the lesions may have a lighter central area rather than an entire dark central region, so a central power suppressing scheme was developed by multiplying the subtraction result with the projection curve $P_j$. The means of the curves $P_f$, $P_j$ are also used to normalize the curve, giving the final equation of the bounding curve $B_j$:

$$B_j = [P_j - (P_f - \overline{P_f})]\frac{P_j}{\overline{P_j}}$$

In order to find the two major maxima for the outer bounding box from the subtraction curve $B_j$, the global minimum of the curve is found. The curve is split in two based on the global minimum, and the two maxima $[m_{c1}, m_{c2}]$ are found on each part of the curve. The index of the two maxima is the index of the column bounding box. The row bounding box indices $[m_{r1}, m_{r2}]$ are found in the same way. FIG. 11 presents an example of the bounding box detection process. Although there were exceptions within this image set, the outer bounding box is generally outside the lesion boundary. Similarly, the inner bounding box is not guaranteed to fall totally inside the lesion, and it does not in this example. Nevertheless, the subtraction curve method generally produces an accurate estimate of the true lesion ratio. Additionally, if there is no maxima on one or more sides (no bounding box border interior to image edge) that becomes a criterion for lesion extending to periphery of image, as noted in the section below "border going to edge of image."

First Lesion Ratio Estimate Based on Outer Bounding Box

Figure 12:
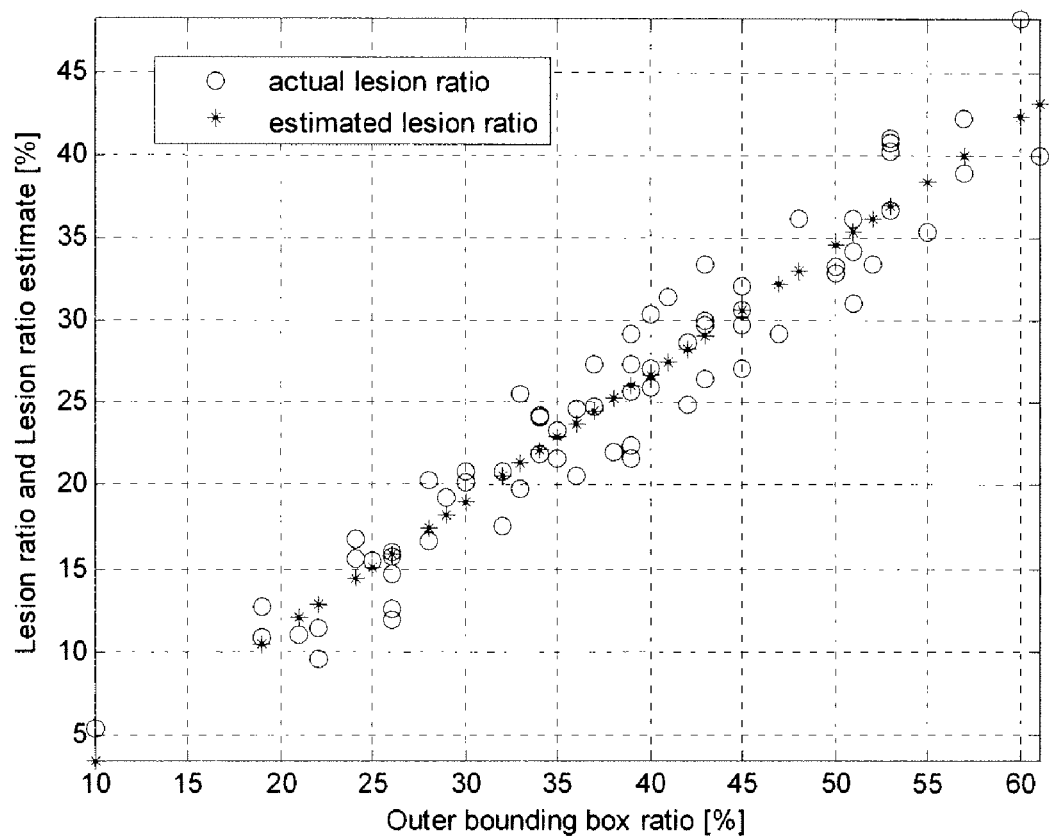
FIG. 12 shows the linear relationships between the actual and the estimated lesion ratios on the 70 benign lesion images.

Once the outer bounding box is determined, the bounding box ratio β is given by the ratio of the outer bounding box area to the image area. The bounding box ratio has a significant linear relationship with the lesion ratio, as shown in FIG. 12. The lesion ratio estimate $\hat{\gamma}$ is given by the equation determined by the mean-square best-fit linear relationship between the actual lesion ratio and the bounding box ratio:

$$\hat{\gamma}_B = 0.7799\beta - 0.0436$$
$$= 0.7799\frac{(m_{r1} - m_{r2})(m_{c1} - m_{c2})}{m \cdot n} - 0.0436$$

For those cases in which one or more bounding box sides are not found, the mean lesion ratio estimate (LRE) is used for the first lesion ratio estimate. If no bounding box sides are found, there is at least a moderate probability of the lesion going to the wall on all four sides. A classifier may be used on the no-bounding box case as mentioned elsewhere, but the mean LRE is still the first estimate. As an alternate method, if 1-3 bounding box sides are found, those sides may be retained for bounding box determination and the mean LRE can be used to estimate the remaining sides, with the sides chosen so that the mean LRE is satisfied.

Lesion Ratio Estimate Correction Based on Random Forest Algorithm to Provide Second Lesion Ratio Estimate Although any classifier may be used to provide the lesion ratio estimate correction, good results were obtained with the random forest algorithm. The random forest algorithm (Breiman01) is a statistical classification algorithm that grows many classification trees. Input data is classified by each of the trees, and the output of each tree is considered a vote. The forest is grown using m randomly chosen variables of the M possible variables at each tree node, where m<<M is a constant throughout the forest growth. The best split on the m variables is used to split each node. Trees are grown without pruning. The forest algorithm determines the final classification after counting and weighing votes from all the trees.

The classification error of the forest falls as the correlation among trees falls and the error rates of the individual trees fall. A choice of a small m increases the error of the trees but reduces correlation. The value of m lying between these extremes is determined automatically by the algorithm of Breiman L. (2001), "Random Forests" (Breiman01).

Final features were selected from 44 features. These features are the image area (in pixels); first-iteration lesion area (in pixels), gray levels of the high and low peaks of the object histogram; and the following values in each of four planes, red, green, blue and luminance: entire image pixel means; entire image pixel standard deviations watershed rim averages (described in the next subsection); mean lesion ratio $\hat{\gamma}_L$ estimates; pixel histogram y-axis peak values; pixel histogram x-axis peak gray levels; pixel histogram variances; pixel histogram standard deviations; and the average grayscale of the inner and outer bounding boxes.

The whole data set is classified into three classes. One class represents cases for which the lesion ratio estimate $\hat{\gamma}_B$ overestimates the true lesion ratio by at least 5%. Another class represents cases for which $\hat{\gamma}_B$ underestimates the true lesion ratio by at least 5%. The final class represents cases for which $\hat{\gamma}_B$ is within 5% of the true lesion ratio. The random forest was able to classify all of the instances correctly. Then a final offset was added to $\hat{\gamma}_B$ to get the final lesion ratio estimate.

$$\gamma = \hat{\gamma}_B + P \cdot 0.02$$

$$P = \begin{cases} 1 & \text{under-estimate} \\ 0 & \text{proper-estimate} \\ -1 & \text{over-estimate} \end{cases}$$

Noise Control

Noise in the lesion images arises from lentigines (lacy dark areas in the image, hair, and telangiectasia (the dark river-like areas representing blood vessels), bubbles, and other small skin irregularities. In order to alleviate the noise, several algorithms are introduced in this subsection.

Area Filter

Figure 13:
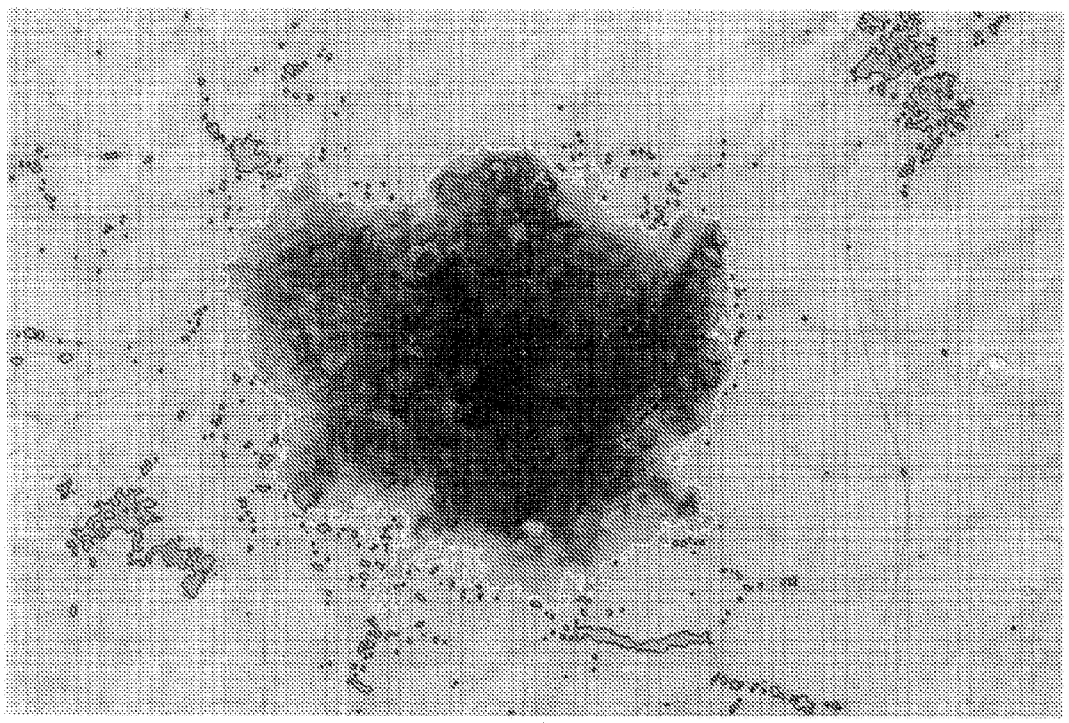
FIG. 13 shows the results of the area filter on the lesion image. Objects identified with black contours are the ones that will be removed by the area filter. The white contour shows the resulting border.

The area filter is an image filter based on the area of the objects in the images. Since all the dermoscopy images contain only one object of interest, the result of the watershed algorithm should also contain only one object. The resulting image is obtained by only keeping the largest object among the N objects in the mask image. In FIG. 13, objects identified with black contours are the ones that will be removed by the area filter. The white contour shows the resulting border.

Object Filling

Figure 14:
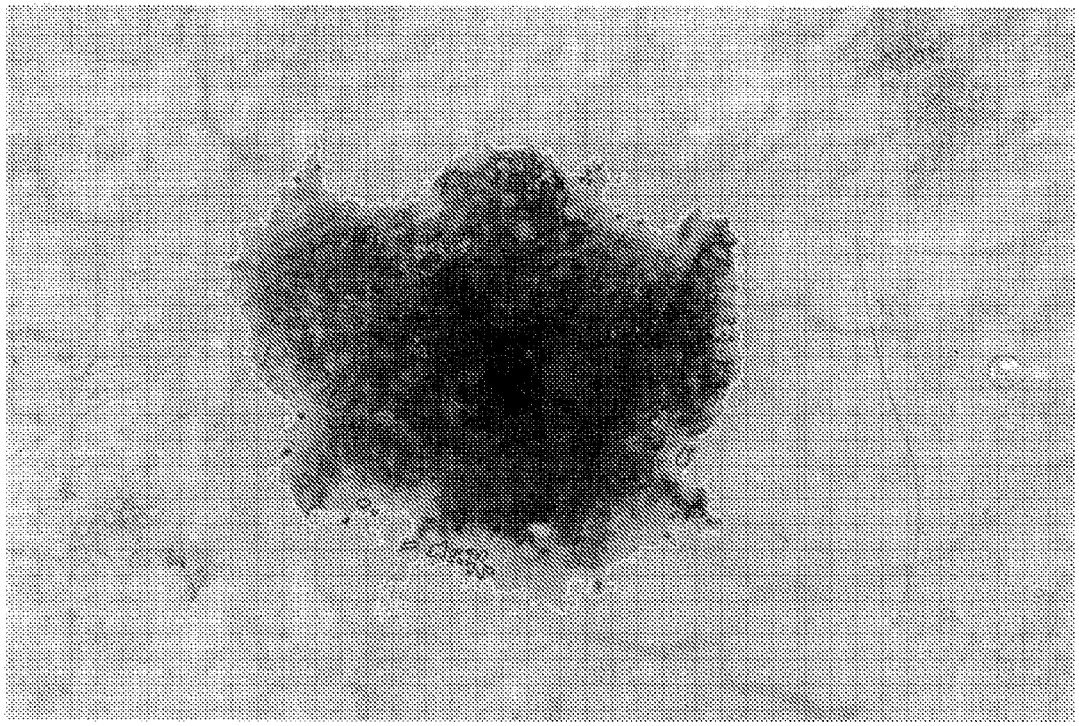
FIG. 14 shows the result after the hole-removing algorithm; black contours are the hole boundaries detected and removed. The white boundary is the final lesion boundary.

The resulting lesion mask is filled using a flood-fill algorithm. Then, the holes in the filled image are removed using mathematical morphology (Soille03). FIG. 14 shows the result after the hole-removing algorithm; black contours are the hole boundaries detected and removed. The white boundary is the final lesion boundary.

Sensitivity of the Watershed Border to the Lesion Ratio Estimate

Figure 15:
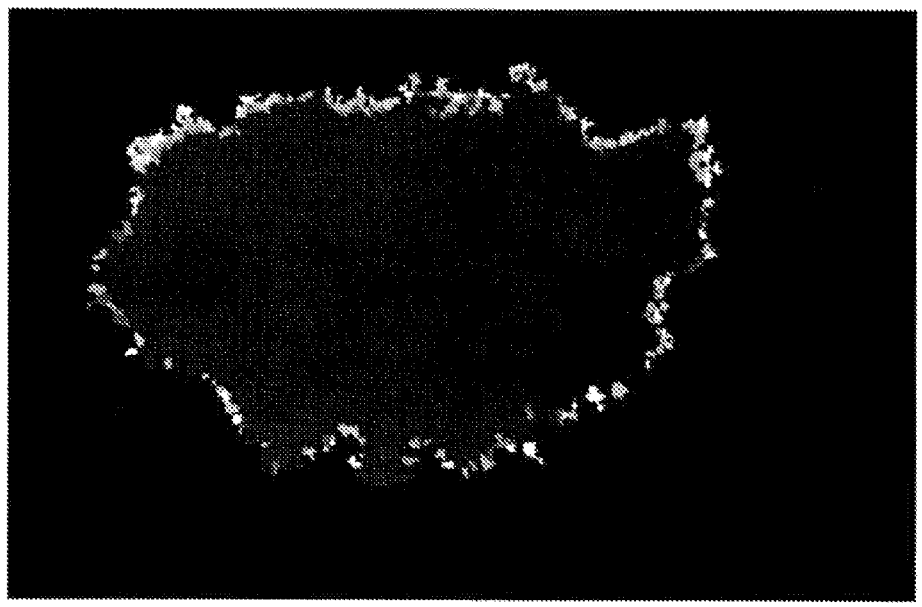
FIG. 15 is a gray scale representation of boundary changes from 7 increments of the lesion ratio estimate $\gamma$. Gray scale changes show how the boundary varies considerably at some areas of the boundary as $\gamma$ varies.

The watershed border is sensitive to the lesion ratio estimate γ but the sensitivity varies greatly for different images, for different γ, and for different portions of the boundary within an image. FIG. 15 shows by gray scale changes how the boundary varies considerably at some areas of the boundary as γ varies. Rather than a series of roughly parallel lines resembling altitude isoclines, the successive watershed borders are generally patchy as shown in FIG. 15.

FIG. 15 shows gray scale representation of boundary changes from 7 increments of the lesion ratio estimate γ: a change of γ of 0.07. White: −0.03 to 0.02 Dark gray: +0.03 to +0.04. The watershed rim average intensity used as an input to the random forest algorithm is the average intensity over the area between the borders determined by lesion ratio estimates between γ and the next increment: γ+0.01.

Lesion Border Smoothing

In order to smooth the jagged borders which result from the watershed algorithm, two techniques were employed, morphological processing and B-spline closed curve fitting.

Border Smoothing by Morphological Operations

Border smoothing by morphological opening or closing (Soille03) can reduce unwanted false positive and false negative errors, usually caused by false convexities or concavities, but these error reductions come at a cost of a greater overall error, as shown in Table 1. The structural element used was ball-shaped with a radius of 31.

TABLE 1

Results of mathematical morphology border smoothing on jagged watershed border without bounding box iteration, or statistical optimization: The overall border error rises.

|  | Before Morph. Opening | After Morph. Opening | Before Morph. Closing | After Morph. Closing |
| --- | --- | --- | --- | --- |
| Average False Positive | 6.78% | 2.78% | 6.78% | 11.15% |
| Average False Negative | 6.38% | 11.21% | 6.38% | 2.55% |
| Average FP + FN | 13.16% | 13.99% | 13.16% | 13.70% |

Border Smoothing by B-spline Curve Fitting

In the final watershed algorithm, second-order B-Spline closed curve fitting (de Boor01) is applied to the original border pixels from the lesion mask. First, a sequence of the border pixels [X, Y] is generated. Second, a smoothing procedure records the starting point then traverses along the boundary and records all the pixels in the path. When the distance from starting point exceeds 32 pixels in either the x or the y direction, an average control point $(\hat{x}_i, \hat{y}_i)$ is calculated with all the pixels' coordinates along the path from the starting point until the border point just prior the point that exceeded the 32 pixel distance in either x or y direction, as expressed in the following equations, $$\hat{x}_i = \frac{1}{N_i} \sum_{n=1}^{N_i} x_n \ |x_i - x_j| < 32 \text{ for } \forall \ i, j$$

$$\hat{y}_i = \frac{1}{N_i} \sum_{n=1}^{N_i} y_n \ |y_i - y_j| < 32 \text{ for } \forall \ i, j$$

where $(x_j, y_j)$ is the starting point.

Figure 16:
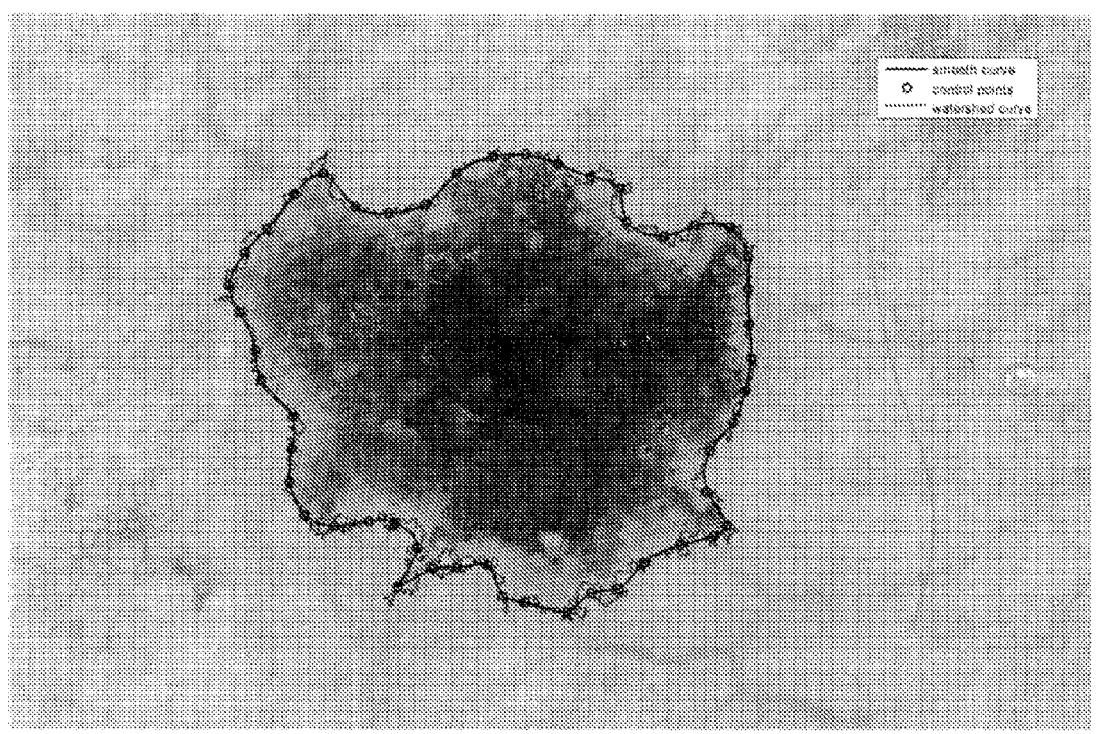
FIG. 16 shows the image after border smoothing using second-order B-Spline curve fitting.

The first point that exceeded the 32-point distance is then used as the starting point for the next block. In this way a set of control points with block size of 32 will be generated and given as input to the B-Spline closed curve fitting. FIG. 16 shows a jagged border and the resulting smoothed curve.

Example

In order to evaluate the effectiveness of the proposed method and compare it with alternative methods, the watershed border detection algorithm was applied to a dermoscopy image set of 30 invasive malignant melanomas and 70 benign skin lesions. Images were 24-bit true color images with typical resolutions of 1024×768 in uncompressed tiff format, from Heine Dermaphot photographs. The benign images included nevocellular nevi and benign dysplastic nevi. All lesions were biopsied. The borders of the images were manually drawn by three dermatologists using software that creates a closed curve based on selected points using second-order B-Spline. The resulting closed skin lesion borders were filled to obtain binary border masks which were then used to estimate the error of the computer-generated lesion borders.

Error Measures

The error rate for Pagadala, GVF, and the JSEG methods were previously determined by using one dermatologist's segmentation as the gold standard. To allow a meaningful comparison with those methods, errors in the current study were computed in the same way. The error metric used was the method developed by Hance et al. (Hance96). Let M represent the area of a manually segmented skin lesion. Let A denote the automatically segmented lesion and ⊕ represent the exclusive-OR operation. Then, the percentage border error E is given by:

$$E = \frac{A \oplus M_{Lesion}}{M_{Lesion}} \times 100\%.$$

An equivalent formulation is to add the false positive areas over the lesion ($FP_{Lesion}$) and the false negative areas over the lesion ($FN_{Lesion}$) and divide this sum by the lesion area ($M_{Lesion}$):

$$E_T = \frac{FP_{Lesion} + FN_{Lesion}}{M_{Lesion}} \times 100\%$$

Results

Figure 17:
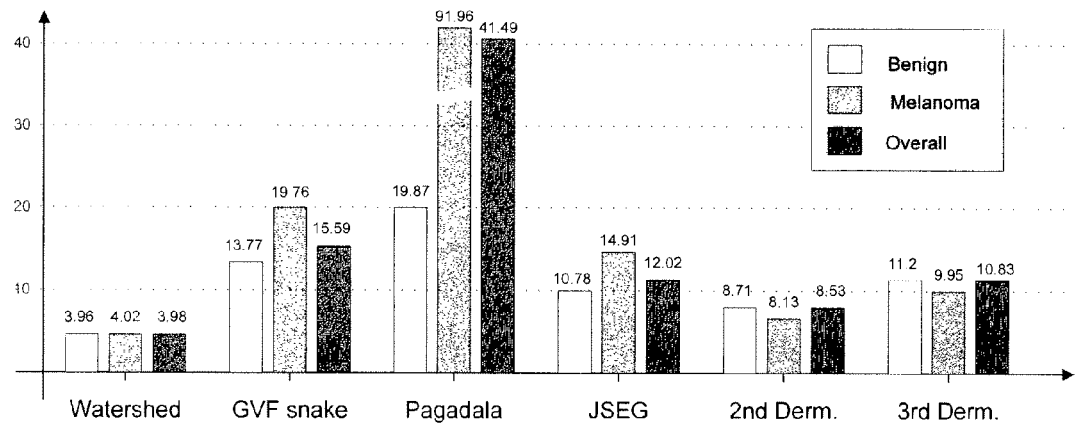
FIG. 17 shows mean error comparison of skin lesion segmentation techniques.

FIG. 17 compares the mean errors of the watershed method and the three previously implemented border detection methods: Pagadala's method (Erkol05), the GVF snake method (Erkol05), and the JSEG method (Celebi06). The watershed error (benign error of 3.96%, melanoma error of 4.02%, and overall error of 3.98%) is significantly lower than the error from the Pagadala's method (benign 19.87%, melanoma 91.96%, and overall 41.49%), the GVF snake method (benign 13.77%, melanoma 19.76%, and overall 15.59%), and the JSEG method (benign 10.78%, melanoma 14.91%, and overall 12.02%). The watershed-based border segmentation is also much more stable (measured by standard deviation of the error, FIG. 18) than Pagadala's method (benign: 59.53, melanoma: 234.46, overall 112.01), the GVF snake method (benign: 5.61, melanoma 8.60, overall 6.51), and the JSEG method (benign 6.28, melanoma 8.4, overall 6.91).

Both watershed and dermatologist borders sometimes include darker areas that may be part of the surrounding skin. There is no conclusive way to determine whether these dark areas near the lesion are additional lesions such as lentigines or part of the main lesion.

Figure 18:
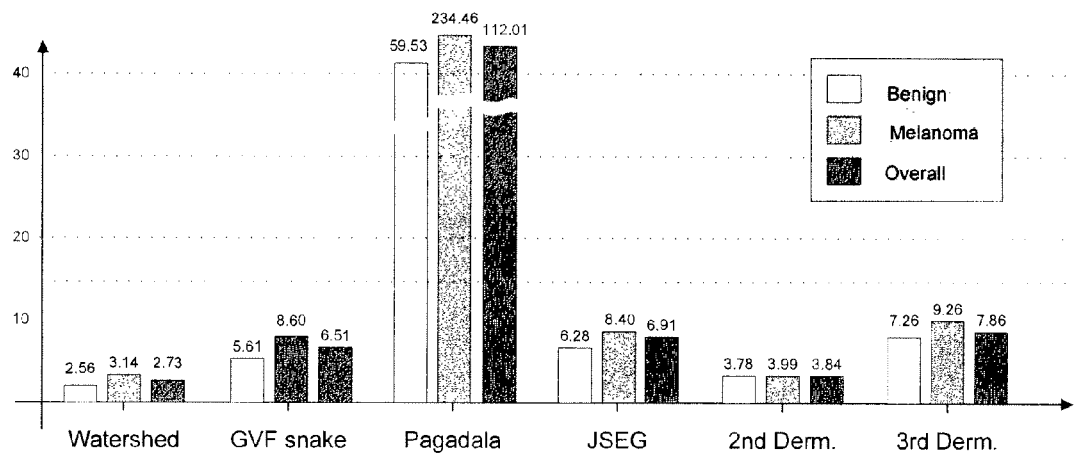
FIG. 18 shows error standard deviation comparisons of skin lesion segmentation techniques.

For comparison purposes, FIGS. 17 and 18 show the area differences between the borders manually drawn by two other dermatologists compared to the dermatologist drawn borders used as the gold standard. These differences were computed in the same manner as algorithm error measure described earlier.

Lesion Border Extending to Edge of Image

The first method to discover that the border goes to the edge of the image is: there is no peak on the subtracted curve obtained from the image horizontal and vertical projections and no outer bounding box (OBB) is possible.

The second method is to apply a classifier to the image histogram and first lesion ratio estimate and other key variables as used in the second (final) lesion ratio estimate. The lesion ratio estimate is considered a key variable, as a high lesion ratio estimate gives a larger probability of the lesion extending to the edge of the image. An additional variable for input to the classifier is the OBB calculation curve peak or the absence of a peak if no maxima was found on the subtraction curve analyzed earlier. A classifier is used with two outputs for each of the four image boundaries: the lesion either goes to the edge of the image or it does not for each image boundary: top, right, left and bottom.

Removal of Peninsulas and Large False Areas in the Image

Figure 19:
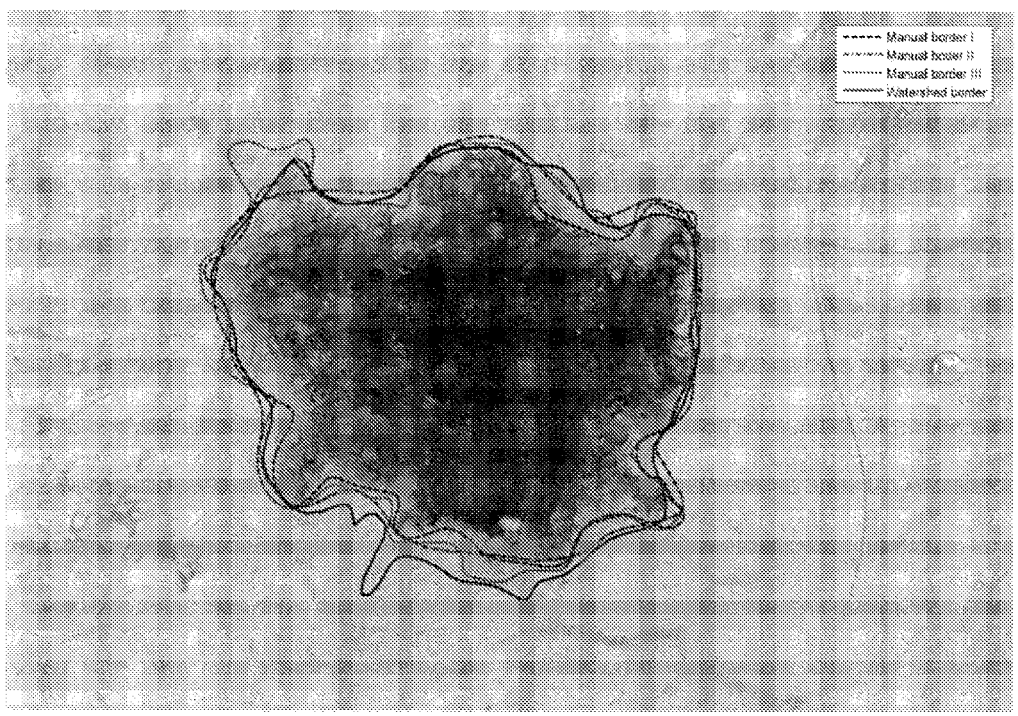
FIG. 19 shows a lesion image with manually-drawn borders by different dermatologists compared with the watershed borders of this invention.

Peninsulas and other large areas connected by a narrow neck to the main lesion were found to be errors in approximately of the 100 images, and in no cases were the peninsulas or other narrow-necked areas found to be part of the lesion by the dermatologists. An example of a peninsula is shown in FIG. 19. These peninsulas are corrected by either morphological processing or a distance transform method. Because of the errors introduced by morphological processing (see border smoothing by morphological processing above), a distance transform was used to find the false positive border areas. The distance transform assigns a closest integer distance i to all lesion pixels indicating the Euclidean distance from the lesion pixel to the nearest pixel outside the lesion border. The area was calculated for all pixels of distance transform less than or equal to i. When the growth from i to i+1 produces a growth in area greater than a threshold amount, a peninsula or other narrow-necked area is considered a possibility. A dynamic threshold, which may be determined by an automatic classifier, was used to exclude those growth areas which are greater than the threshold.

Further Error Reduction: Addition of Regression Areas Near the Border.

A second method of error reduction includes those areas which have pixels that are lighter than background skin as previously determined and are pale white, pale pink, or pale blue and are close to the initial border and asymmetrically distributed about the lesion. The asymmetry is determined by the eccentricity index used for blotches. These areas are considered regression and will be excluded unless specifically sought.

Second Iteration of the Digital Hair Removal Algorithm

Figure 20:
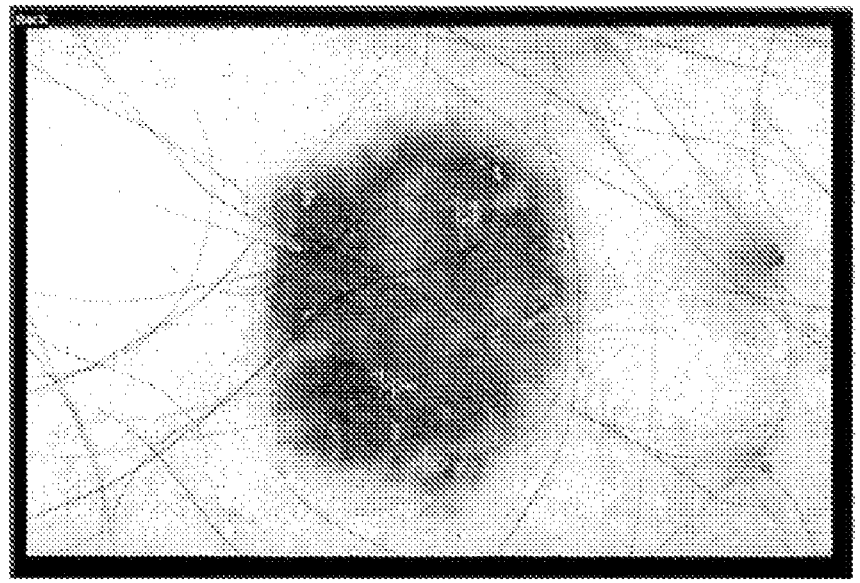
FIG. 20A shows an image with hair before application of a digital hair removal algorithm.
FIG. 20B shows hairs detected on the image after both first and second stages of the modified digital hair removal algorithm have been applied.
Figure 20:
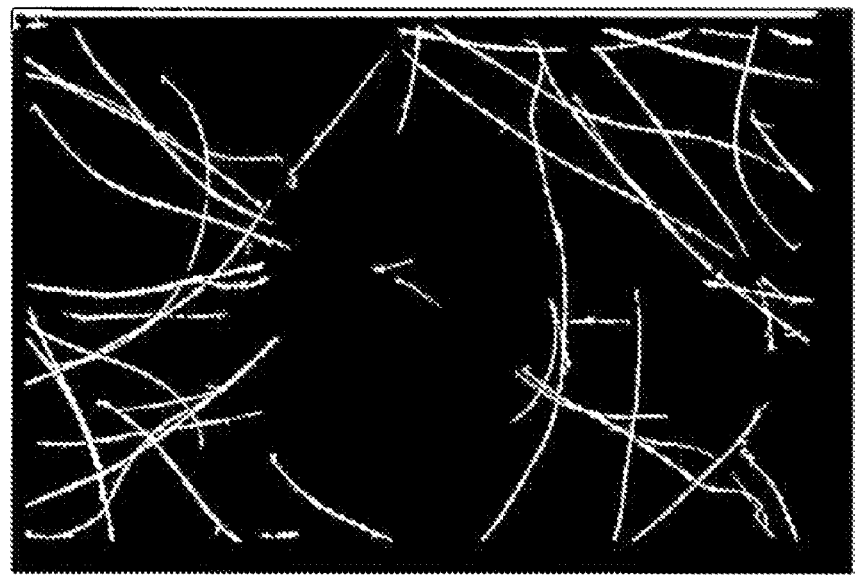

After the border was found, the digital hair removal algorithm was applied a second time with two modifications: 1) The size of the objects removed outside the border was dynamic, depending on the object histogram, and was typically 50 pixels, range 40 to 200, and size of objects removed inside the border was also dynamic, and was typically 200 pixels, with range 100 to 400 pixels. FIG. 20 shows the result after the second application of the digital hair removal algorithm.

Hair finding can be used to extend inward from the watershed border all hairs detected by the first digital hair removal algorithm pass at the border, with the advantage that fewer pigment network lines within the border are detected as hairs and erased as with the original DullRazor™ method.

Feature Preprocessing: Finding Background Skin Color

Method to Calculate Background Skin Color

The background skin color was computed by averaging skin color, red green and blue, over the selected non-lesion portion of the image. An area of 10% of the lesion size around the lesion was omitted, to reduce the effect of peri-border inflammation and errors in border determination. This area was found using the distance transform to define nearness (Euclidean distance to the nearest lesion boundary point).

For small lesions, occupying approximately 25% of the image area or less, the number of pixels for averaging nonskin was increased until the area of the region to be averaged is $\geq 4$ times the area of the lesion. For larger lesions, all non-lesion pixels that satisfy the skin color definition (i.e. not non-skin) were included in the average. (These limits are approximate and are given as limits that perform well; they can be varied.)

Blotch, Globule and Dot Area Detection

All of these features are dark structures in pigmented lesions but not considered part of the pigment network (Seidenari06) or in the case of blotches, obscuring the pigment network. Blotches are large structures, globules medium-sized structures, and dots the smallest pigmented structures, although limits of their sizes are not usually given. One exception to this absence of defined limits is the largest size of dots, sometimes given as 0.1 mm, (Carli00) which can be taken as the lower size limit of globules (Carli00). Generally, no precise size limitations are given, and in the consensus dermoscopy meeting (Argenziano03), dots and globules were often combined in descriptions as dots/globules. The sizes given here may be taken as arbitrary, because we used similar structure measures for the three dark structures and what was not found in one category was found in a category of another size.

Blotch Detection

Blotches are nowhere precisely defined in the literature, except that they are dark and structureless, i.e., without a pigment network. Blotches for benign (dysplastic) nevi (FIG. 21) are less eccentric, smaller and less numerous than those for melanoma (FIG. 22). We found them and found critical features regarding them using the following methods. The background skin color was computed as above. Using both relative and absolute colors, blotches were detected automatically by using thresholds in the red and green color planes. Relative color blotch detection was found to produce better diagnostic accuracy than absolute blotch detection. (Stoecker05a).

Figure 21:
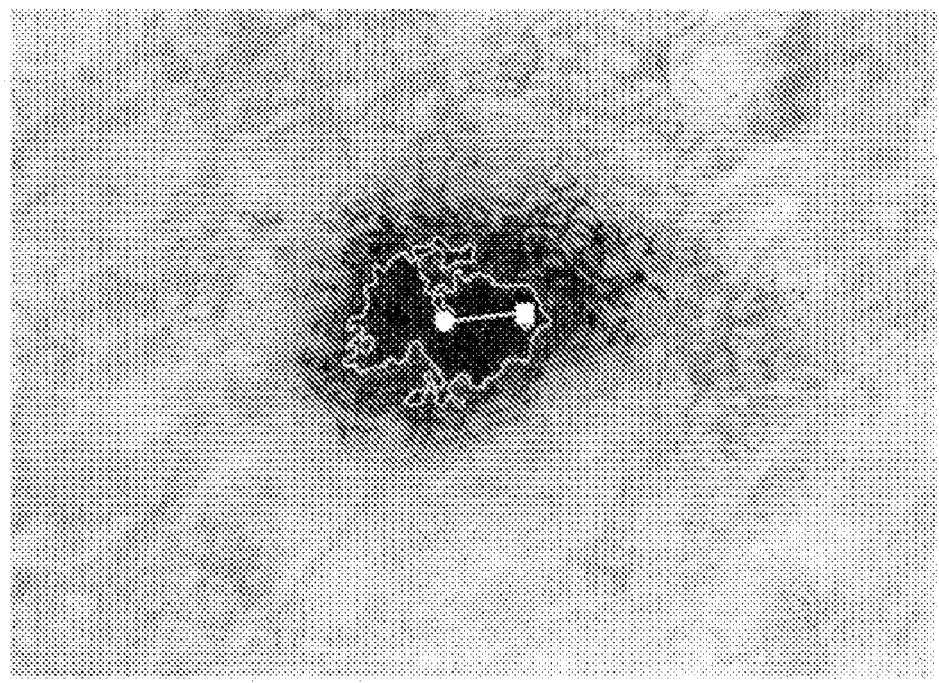
FIG. 21 shows an image of a dysplastic nevus with the outline of the largest blotch found automatically.
Figure 22:
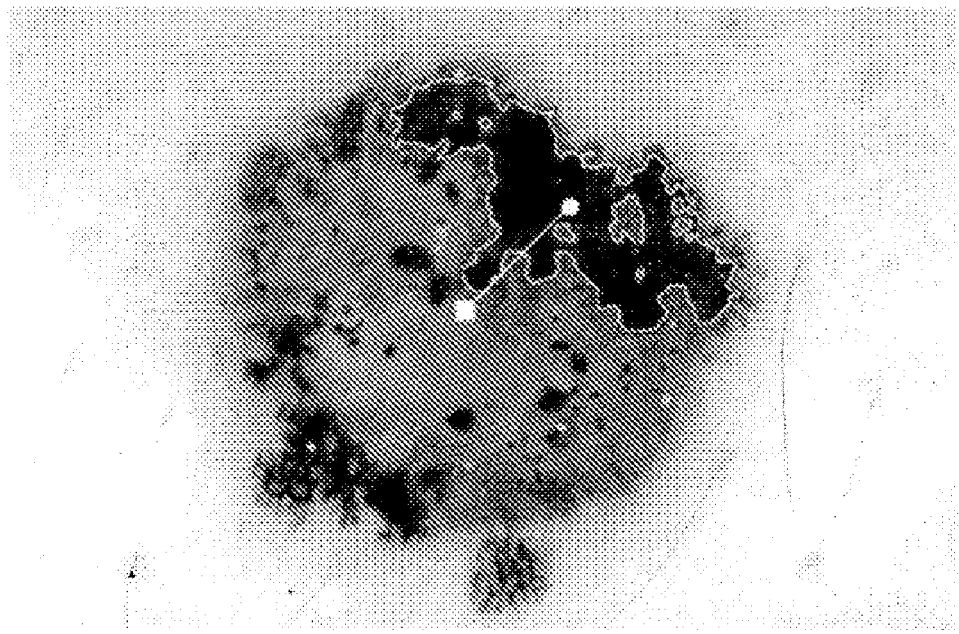
FIG. 22 shows an image of an invasive melanoma (from Argenziano00) with the outline of the largest blotch found automatically.

FIG. 21 shows a dysplastic nevus with the outline of the largest blotch found automatically. The centroid of the tumor is marked with a square; the centroid of the largest blotch is marked with a circle; the intercentroid distance is marked as the line between the two centroids. The eccentricity index is 0.21. The irregularity index is 12.4.

FIG. 22 shows an invasive melanoma with the outline of the largest blotch found automatically. The centroid of the tumor is marked with a square; the centroid of the largest blotch is marked with a circle; the intercentroid distance is marked as the line between the two centroids. Boundaries for this blotch are sharp and clearer than for the blotch in FIG. 21. The eccentricity index is 0.30. The irregularity index is 12.8.

Relative color blotch detection was accomplished by the following screen:

($R_{skin}$−R>$R_{rel\ threshold\ blotch1}$) OR (($R_{skin}$−R>$R_{rel\ threshold\ blotch2}$) AND ($G_{skin}$−G>$G_{rel\ threshold\ blotch}$)). The first part of the rule before the "OR" was used to find the darkest blotches with less erythema. $R_{skin}$ and $G_{skin}$, respectively, are the red and green averages for the background skin. R, G, and B denote the red, green and blue value of the pixel under consideration. $R_{rel\ threshold\ blotch1}$=140 typically, $R_{rel\ threshold\ blotch2}$=110 typically, and $G_{rel\ threshold}$=140 typically, with $R_{rel\ threshold1}$ ranging from 115-165 or other similar limits, $R_{rel\ threshold2}$ ranging from 85-135, and $G_{rel\ threshold\ blotch}$ ranging from 115-165.

Fuzzy Blotch Detection

Figure 23:
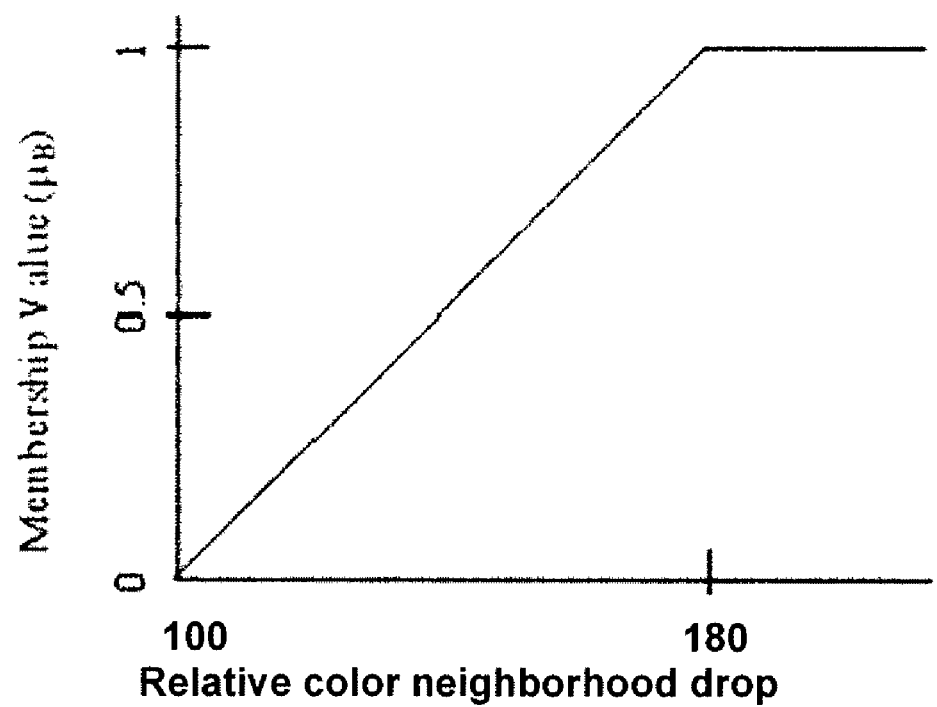
FIG. 23 graphs membership function for fuzzy blotch determination.
Figure 24:
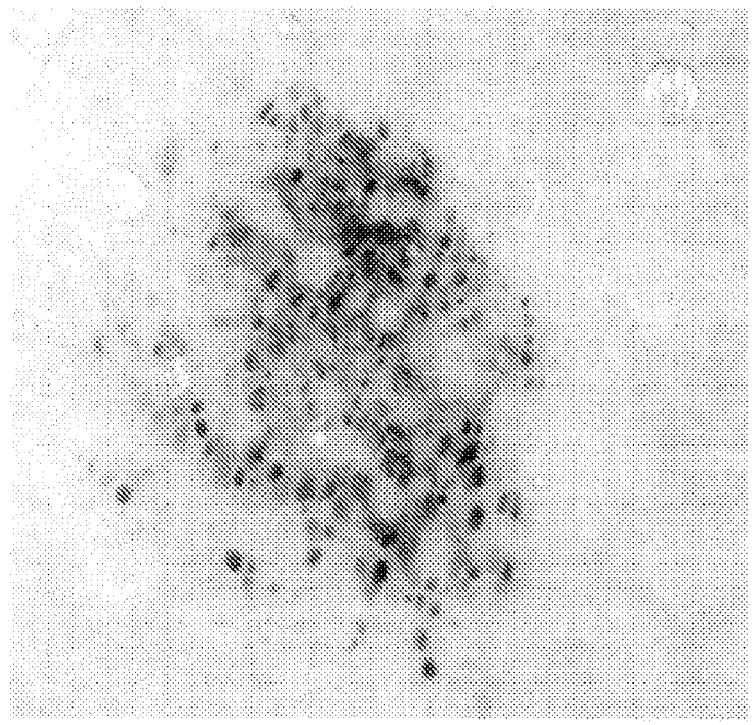
FIG. 24A shows a benign lesion with globules. Globules are regular in shape and not asymmetrically located.
FIG. 24B shows the automatically detected globules.
Figure 24:
Figure 25:
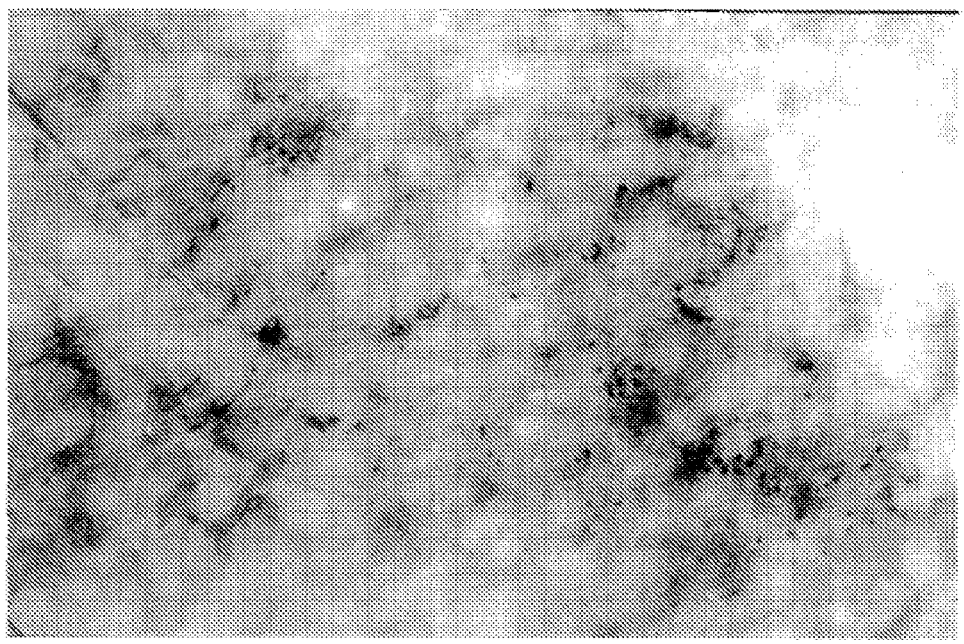
FIG. 25A shows a malignant melanoma. Globules are irregular in shape and somewhat asymmetrically located.
FIG. 25B shows the automatically detected globules.
Figure 25:

Another implementation is the two-dimensional fuzzy implementation, using two membership functions for red color drop:

$R_{fuzzy\ threshold1}$<$R_{skin}$−R<$R_{fuzzy\ threshold2}$, and for green color drop optimizing alpha cuts, and 100<$G_{skin}$−G<180, with optimization of alpha cuts. Typically, $R_{fuzzy\ threshold1}$=100 and $R_{fuzzy\ threshold2}$=180, with these thresholds varying up to 20%. An example of a typical fuzzy blotch trapezoidal detection membership function is shown in FIG. 23; this membership function can be applied to either red or green drops, with varying limits.

Globule Elimination

Globules can be distinguished from blotches by their smaller size. For images of typically 1024×768 resolution, blotches had a size exceeding 800 pixels, on the order of 0.5 mm diameter. Therefore, the blotch requirement $A_{blotch}$≧800 is included to eliminate globules. The number is intended as a typical limit; note that the blotch size floor is the same as the globule ceiling and thus can be varied without harm to the method. Although 800 is typical, other values can be used.

Blotch Features

Nine indices were used to characterize the automatically-detected blotches. The most useful blotch eccentricity index is the blotch eccentricity index, given by $$E = \frac{D}{\sqrt{A}},$$

where D is the Euclidean distance between the centroid of the largest blotch and the centroid of the lesion and A is the lesion area. This had a high significance for melanoma, p<0.001, for chi-squared statistical analysis.

The second index is the relative size of all blotch areas, obtained by dividing the sum of all blotch areas found by the area of the lesion and is represented as:

$$R = \frac{\sum_{i=1}^{n} B_i}{A},$$

where n is the number of blotches for the skin lesion and $B_i$ is the area of blotch i within the lesion. The third index is the relative size index for the largest blotch and is denoted as:

$$S = \frac{B_{max}}{A},$$

where $B_{max}$ is the area of the largest blotch region within the skin lesion. The fourth and fifth indices are the size of the largest blotch found ($B_{max}$) and the number of blotches detected within the lesion (n), respectively. The sixth index is the irregularity of the largest blotch and is given by:

$$I = \frac{P_{max}}{\sqrt{B_{max}}},$$

where $P_{max}$ is the perimeter of the largest blotch within the lesion. The seventh index is the blotch dispersement index, the average distance of the blotches from the centroid of the lesion, scaled by the square root of the lesion area, represented as $$\overline{D} = \sum_{i=1}^{n} \frac{D_i}{n\sqrt{A}}$$

where $D_i$ is the distance of the $i^{th}$ blotch from the lesion centroid and the other variables are defined as stated above.

The eighth blotch index is the average melanoma color index MI taken from the melanoma relative color index (see percent melanoma color determination, below) over the blotches. The ninth blotch index is the median variance in intensity, $\sigma_{within-blotch}^2$, in any chosen color plane, within the blotches. The tenth blotch index is the variance in mean intensity among the blotches, $\sigma_{among-blotches}^2$. All ten indices (E,R,S,n,$B_{max}$,I, $\overline{D}$,MI, $\sigma_{within-blotch}^2$,$\sigma_{among-blotches}^2$) are candidates for use as inputs to a classifier such as an artificial neural network (ANN). In one implementation, six of the indices were used. Relative indices generally provide better discrimination, with E providing giving the greatest significance (lowest p value) for discrimination, as in Tables 2 and 3. E, the eccentricity of the largest blotch, provides the best melanoma discrimination of those indices tested.

TABLE 2

| | Absolute Indices | | |
|---|---|---|---|
| Indices | Melanoma | Nevi | p value |
| E = Eccentricity Largest Blotch | 0.174 ± 0.158 | 0.073 ± 0.12 | <0.0001 |

TABLE 2-continued

Absolute Indices

| Indices | Melanoma | Nevi | p value |
|---|---|---|---|
| R = Relative area, all blotches | 0.180 ± 0.21 | 0.08 ± 0.15 | 0.06 |
| S = Relative area largest blotch | 0.162 ± 0.21 | 0.07 ± 0.15 | 0.12 |
| $B_{max}$ = No. of pixels largest blotch | 53407.08 ± 123511.64 | 13350.11 ± 45142.08 | 0.09 |
| n = Number of blotches | 22.07 ± 34.09 | 9.88 ± 29.84 | 0.40 |
| I = Irregularity largest blotch | 10.17 ± 7.11 | 5.01 ± 7.36 | 0.88 |

TABLE 3

Relative Indices

| Melanoma | Nevi | p value |
|---|---|---|
| 0.177 ± 0.154 | 0.111 ± 0.135 | <0.0001 |
| 0.29 ± 0.23 | 0.15 ± 0.20 | 0.0047 |
| 0.26 ± 0.24 | 0.14 ± 0.20 | 0.0765 |
| 65435.17 ± 98892.07 | 29064.67 ± 71848.39 | 0.7207 |
| 43.46 ± 81.45 | 19.30 ± 42.26 | 0.0894 |
| 10.75 ± 6.42 | 7.72 ± 7.50 | 0.2782 |

Globule Detection

Relative Color Globules

Method 1

The background skin color $R_{skin}$, $G_{skin}$, $B_{skin}$ was found by implementing the background skin routine. Globule detection was accomplished by the empirically optimized thresholds:

$(R_{skin} - R > R_{rel\ treshold\ globule})$ AND $(G_{skin} - G > G_{rel\ threshold\ globule})$. In practice, $R_{rel\ threshold\ globule} = 93$ and $G_{rel\ threshold\ globule} = 98$ work well, but these can vary considerably, by at least 40 in either direction. The number of globules found by the relative method was somewhat smaller than that found by the absolute method after optimization. When too few globules are found, the method loses sensitivity for melanoma detection because some borderline melanomas with few globules are not detected. When too many globules are found (false globule detection), the method loses specificity because too many benign lesions are found with false globules.

An additional problem is the elimination of dark areas within blotches. Some lighter blotches have dark areas that are small enough to be found by the above criteria. To eliminate these small dark globule-colored areas within larger blotches, we demanded that the globule be significantly darker than the surrounding area. For a typical globule, intensity drops from neighborhood pixels, $R_{neighborhood} - R_{globule} > 10$ AND $G_{neighborhood} - G_{globule} > 6$, where $R_{globule}$ is defined as the average red value within the globule and $R_{neighborhood}$ is the average value of the closest A/2 pixels outside the globule and outside all other globules, where A is the number of pixels within the globule. Green values are defined similarly. This floor was found to identify too many globules and was modified as follows.

Modification of Techniques

Red and green pixel values were used as in previous related work (Stoecker05a). Red and green pixel thresholds were iteratively adjusted by observation of the globule areas obtained until the globule areas found by both methods were felt to be fairly similar, with both methods finding areas corresponding closely to globules. After optimization, the absolute method unavoidably found greater globule areas and numbers. Because both methods found some dark border areas as globules, we added a constraint that either R or G>0. Because thin hairs were sometimes found as globules, we used a modified version of the digital hair removal algorithm, with elimination of filtering for pre-processing (Chen05).

Blotch and Dot Elimination

Blotches can be distinguished from globules by their larger size. No standard definition of maximum globule size is known. We estimated that for our images of typically 1024× 768 resolution, blotches have a size exceeding 800 pixels, on the order of 0.2 mm diameter, so the globule requirement $A_{globule} < 800$ was included to eliminate blotches. For images of different magnification or resolution, the requirement is proportional. Again 800 can vary, as the maximum size of globules is the same as the minimum size for blotches.

Dots are eliminated by demanding that the candidate globule area have a size greater than approximately 30 pixels, i.e., $A_{globule} > 30$ is included to eliminate dots. This size of 30 may be modified, as the minimum size of globules is the maximum size of dots.

The final step for blotch elimination, using hard thresholds as above, was modified to demand that R and G drops from background to globule exceed the median drop for each globule that met size constraints. Excess globules were found, and this was further modified by demanding a floor to the globule—background difference of $R_{neighborhood} - R_{globule} > 6$ AND $G_{neighborhood} - G_{globule} > 2$.

Method 2

Globules can also be detected by constructing a histogram for the image of the drops between the candidate globule areas and the globule neighborhood as noted previously, $R_{neighborhood} - R_{globule}$ and $G_{neighborhood} - G_{globule}$, where $R_{globule}$ is defined as the average red value within the globule and $R_{neighborhood}$ is the average value of the closest A/2 area. A routine demands that each drop be greater than an optimized histogram threshold. In practice, these thresholds are in the neighborhood of 0.9 and 0.85. This is equivalent to the demand that when the average red of the candidate globule is compared to the average red of the surrounding area, the candidate globule must have a red drop greater than 90% of all globule candidates. Similarly, the rule for green demands that the candidate globules must have a green drop greater than 85% of all globule candidates.

Fuzzy Globule Detection

Another implementation is the two-dimensional fuzzy implementation, using two trapezoidal membership function limits for red color drop: $R_{fuzzy\ threshold1} < R_{skin} - R < R_{fuzzy\ threshold2}$, and similarly, for green color drop, $G_{fuzzy\ threshold1} < G_{skin} - G < G_{fuzzy\ threshold2}$, with optimization of alpha cuts. Typically $R_{fuzzy\ threshold1} = G_{fuzzy\ threshold1} = 100$ and $R_{fuzzy\ threshold2} = G_{fuzzy\ threshold2} = 180$, with these thresholds varying up to 20%. The membership function example shown in FIG. 23 can be used for fuzzy globule determination.

Globule Features

A subset of the ten indices used for blotches above is used for globules. The eccentricity index is redefined using the centroid of all the globules:

$$E = \frac{D}{\sqrt{A}},$$

where D is the Euclidean distance between the centroid of all the globules and the centroid of the lesion and A is the lesion area. All ten indices (E,R,S,n,$B_{max}$,I,$\overline{D}$,MI, $\sigma_{within\text{-}globules}^2$, $\sigma_{among\text{-}globules}^2$) are candidates for use as inputs to a classifier such as an artificial neural network (ANN). In one implementation, six of the indices are used. Statistics are shown in Table 4. Note that the globule dispersement index provides the best discrimination.

TABLE 4

Globule Indices

| | Absolute Indices: Mean Standard Deviation | | | Relative Indices: Mean Standard Deviation | | |
|---|---|---|---|---|---|---|
| Indices | Melanoma | Nevi | p value | Melanoma | Nevi | p value |
| E = Globule eccentricity index | 0.193 0.181 | 0.122 0.159 | 0.048 | 0.188 0.171 | 0.112 0.151 | 0.148 |
| R = Relative area, all globules | 0.002 0.003 | 0.002 0.004 | 0.735 | 0.002 0.003 | 0.002 0.004 | 0.323 |
| S = Relative area largest globule | 0.001 0.002 | 0.001 0.002 | 0.469 | 0.001 0.001 | 0.001 0.002 | 0.389 |
| $G_{max}$ = No. of pixels largest globule | 245.63 253.17 | 164.38 241.88 | 0.547 | 235.33 254.13 | 150.33 231.81 | 0.775 |
| n/A = No. of globules per unit lesion area | 0.017 0.019 | 0.013 0.023 | 0.643 | 0.014 0.017 | 0.014 0.031 | 0.014 |
| I = Average irregularity of globules | 4.650 3.206 | 3.203 3.371 | 0.150 | 4.768 3.495 | 3.1094 3.5507 | 0.513 |
| D = Globule dispersement | 0.303 0.207 | 0.174 0.193 | <0.0001 | 0.280 0.196 | 0.159 0.187 | <0.0001 |

Dot Detection

Brown and black dots are sometimes defined as less than 0.1 mm in size (Carli00) but otherwise nowhere precisely defined in the literature. We find them and find critical features regarding them using the following methods, which are quite similar to our globule detection methods except for the size, whose ceiling is the same as the lower boundary for size of the globules.

Relative Color Dots

The background skin color $R_{skin}$, $G_{skin}$, $B_{skin}$ was found by implementing the background skin routine.

Dot detection was accomplished by first demanding that the following empirically optimized thresholds be met: $R_{skin}-R>93$ AND $G_{skin}-G>98$. These sizes can vary somewhat; as they increase, fewer true globules are found and some melanomas may be missed; as they decrease, more false globules are found and some benign lesions may be scored malignant.

Blotch and Globule Elimination

Globules can be distinguished from dots by their larger size. The estimate of 0.1 mm maximum dot size is implemented by demanding that candidate dots have a size smaller than approximately 40 pixels, i.e., $A_{dot}<40$ pixels is included to eliminate globules. This size may be modified. Note that some overlap with globule size is permitted.

In practice, a blotch-globule mask is constructed with relative color drops as noted above. The candidate dots should not be within the blotch-globule mask except as follows.

Inclusion of Dots Close to the Edge of Large Blotches

Larger blotches, those with $A_{blotch}>30,000$ pixels, are selected. These masks, and only these masks, are eroded with a structuring element of a radius of 25. This allows the detection of dots that are close to the border of larger blotch masks.

Candidates for dots are screened, similar to globules, by constructing a histogram for the image of the drops between the candidate dot areas and the dot neighborhood as noted previously, $R_{neighborhood}-R_{dot}$ and $G_{neighborhood}-G_{dot}$, where $R_{dot}$ is defined as the average red value within the dot and $R_{neighborhood}$ is the average value of the closest area, typically equal to that of the dot candidate. A routine demands that each drop be greater than an optimized histogram threshold. In practice, these thresholds are in the neighborhood of 0.9 and 0.85. This is equivalent to the demand that when the average red of the candidate dot is compared to the average red of the surrounding area, the candidate dot must have a red drop greater than 90% of all dot candidates. Similarly, the rule for green demands that the candidate dot must have a red drop greater than 85% of all dot candidates.

Dot Features

Dot features are similar to globule features as above, with the definition of eccentricity E used as in globules and the elimination of within-dot variance. All nine indices (E,R,S,n, $B_{max}$,I,$\overline{D}$,MI,$\sigma_{among\text{-}dots}^2$) are candidates for use as inputs to an artificial neural network (ANN).

Computing Boundary Gradient Distribution, Method One

The boundary gradient is determined by first identifying the lesion border and the lesion centroid.

For every border point, excluding those at the edge of the image, using any single color plane, such as luminance or a plane found using the Principal Components Transform (PCT) or IHP (Gomez06):

- Determine the slope of the line from the border point to the Centroid
- Obtain the two arrays of 5 collinear points. The first 5-point array is centered at the boundary. The second 5-point array is centered 50 points outside the boundary. The range for 5 can vary from 3 to 19 and the range for 50 can vary from 15 to 150.
- Compute the gradient from the two arrays of points based on the intensity values.
- Compute histogram of gradients, where the x-axis is the gradient level and the y-axis is the number of border pixels with that gradient; smooth histogram using histogram smoothing techniques.
- If two peaks, split at interpeak mean.
- If three peaks, split at interpeak means.
- If four or more peaks, split at mean between highest and lowest peak.
- For each of these gradients within a given split, replace the gradient by the mean gradient for that cluster. This new gradient histogram after computing the gradient splits may be considered a gradient map, as it maps all gradients within a given split (all x-axis values within the split) to the mean gradient for that split. All border pixels are thus mapped first to their given calculated gradient and then via the new gradient histogram to a mean gradient.

On lesion border, denote membership at a border pixel in one of the two or three values of gradients on the new gradient histogram Each set of contiguous border pixels that is mapped to the same mean gradient is called a cluster.

Compute eight values:
1. Sum of sizes of all clusters mapped to lowest and highest gradient. Normalize by number of border points that are not at the image edge. This yields two indices: the fraction of pixels that belong to highest-gradient cluster and lowest-gradient cluster.
2. Average size of highest-gradient and lowest-gradient clusters.
3. Mean gradient for highest and lowest gradient splits
4. Eccentricity (defined elsewhere) of high-gradient clusters.
5. Number of highest-gradient clusters.

These eight values are saved and used as inputs to the classifier

Computing Boundary Gradient Distribution, Method Two

For every $33^{rd}$ border point (range 20-60) find the median gradient for the point and the 16 neighbors in either direction, proceeding along the border.

Do a median gradient split (2 groups) and a tertile gradient split (3 groups).

Compare qualities of clustering (standard deviation within a group) to determine whether two or three mean gradients are optimal.

Map all gradients to two or three mean gradients and proceed as in method one.

Figure 26:
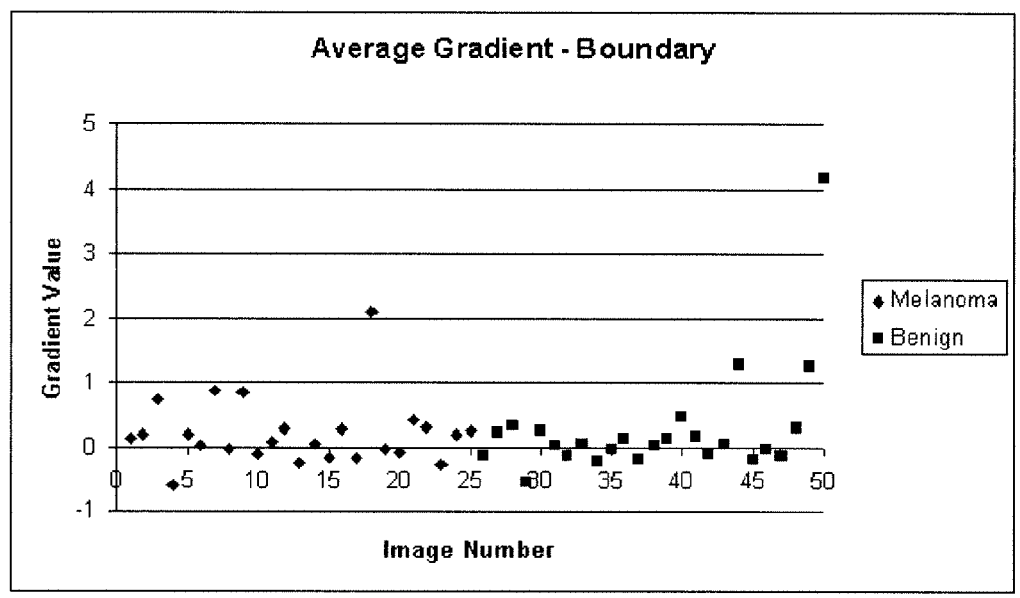
FIGS. 26A-D show gradient statistics for benign lesions and melanomas.
Figure 26:
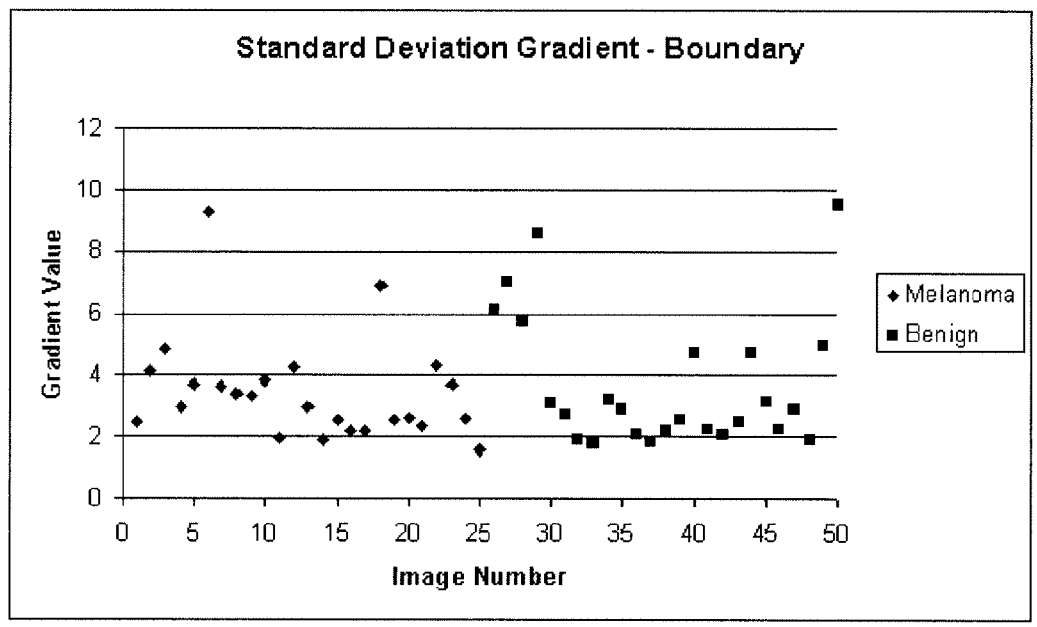
Figure 26:
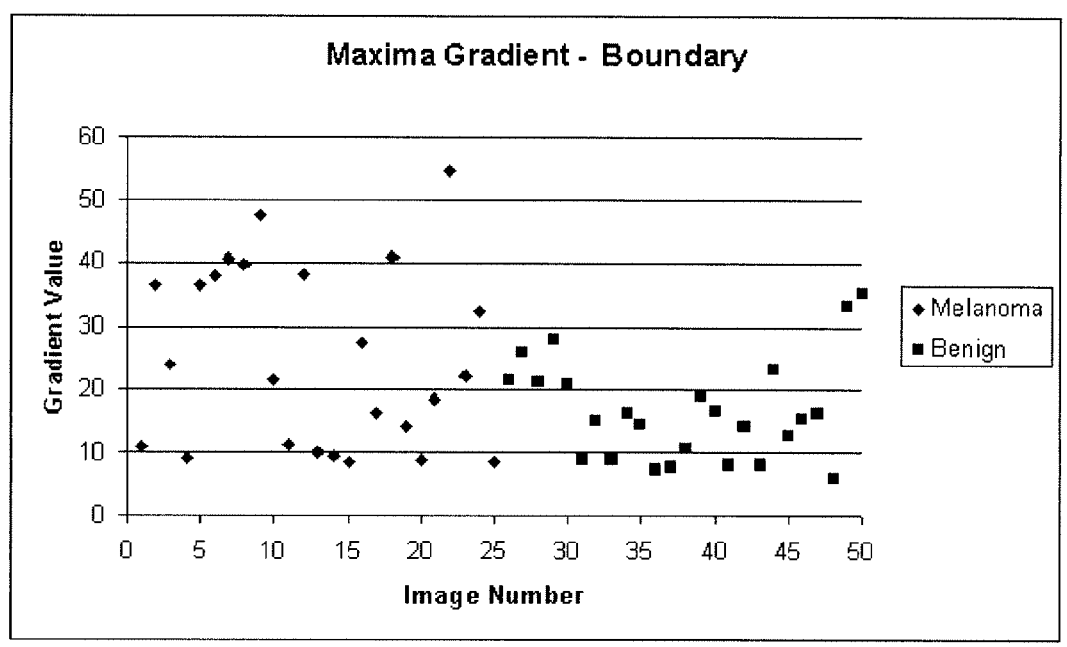
Figure 26:
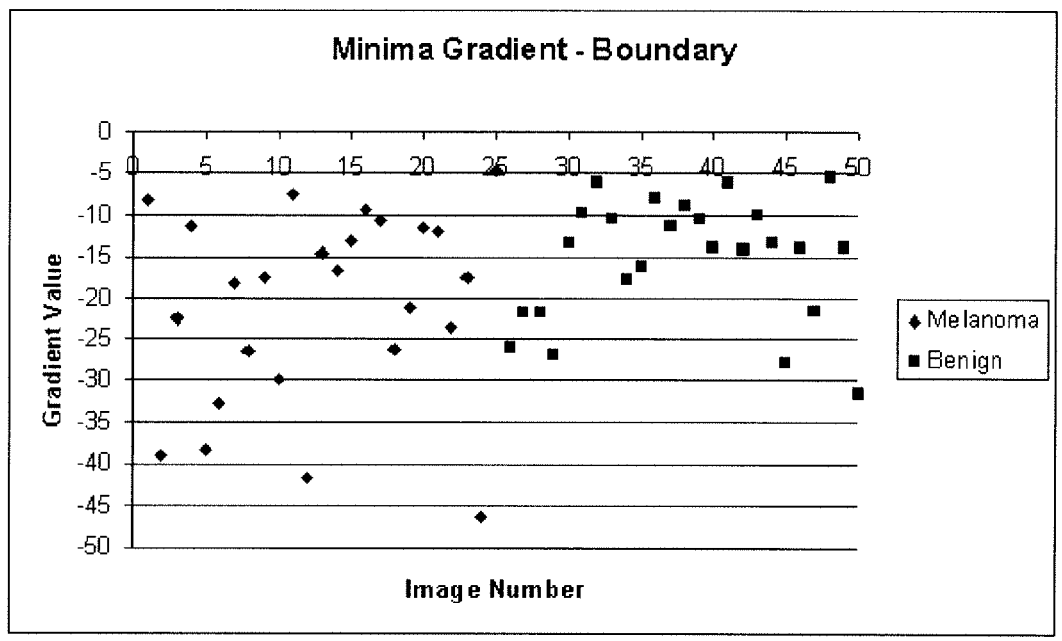

Note that the high-gradient cluster fraction provides a measure of the size of the melanoma clone which may have arisen within the benign lesion, and the mean gradient for the high-gradient split is related to the likelihood of melanoma for that clone. Here a clone refers to a group of cells with similar characteristics, in this case the malignant part of a lesion that is part benign and part malignant. We have determined that with such clones, the fraction of border points within the high-gradient cluster is typically 0.4, with a typical range of 0.2-0.6, and that the gradient is fairly high in such melanoma clones. Boundary gradient distribution for melanomas and benign lesions, computed by method one, are shown in FIG. 26. These saved values are used as inputs to an automatic classifier such as an ANN.

Note that neither average nor standard deviation provides much melanoma discrimination. Our methods provide better discrimination-based on the fraction of border points lying within a high-gradient cluster (HGC) and the size and number of the high gradient clusters. Note that one melanoma scoring system (Nachbar94) finds a higher melanoma index for high gradients in more octants. Our method separates out melanomas which have a high gradient in a clustered portion of the lesion, with high gradient (termed sharp cutoff in some systems) in the range of 40% more indicative of melanoma. This greater indication of melanoma for partially sharp borders provides improved discrimination of these lesions with a clone of melanoma within a benign lesion. The usefulness of this feature is supported by the higher odds ratio for melanoma of this partial sharp gradient features, noted in Argenziano03.

Color Characterization

Prior Art: Constructing Color Histogram And Prior Color Measures Pmc and Ccr

Color Clustering Ratio, Percent Melanoma Color and Fuzzy Logic Color.

The first two features, color clustering ratio and percent melanoma color, are based on mapping all pixels within the lesion boundary of the relative color image to a three-dimensional quantized relative color histogram H, with the histogram having dimensions $511^3$, as detailed in the following. The third feature applies fuzzy logic to determinations based on H.

Assigning Benign and Malignant Bins in H

Instead of mapping pixels from the images to the bins, which would over-represent large lesions or images at higher resolutions, the bins instead contain a count of all malignant images $M_{ijk}$ and benign images $B_{ijk}$, for which more than a threshold t of their pixels map to the bin $b_{ijk}$ in the quantized H, where t is chosen to reduce noise without interfering with the mapping. For a training set with $M_{total}$ malignant lesions and $B_{total}$ benign lesions, if $M_{ijk}/M_{total} > B_{ijk}/B_{total}$, the color group in bin $b_{ijk}$ is more representative of a malignant lesion and the bin $b_{ijk}$ is labeled malignant. Similarly, if $B_{ijk}/B_{total} > M_{ijk}/M_{total}$, the bin $b_{ijk}$ is labeled a benign bin. If $M_{ijk}/M_{total} = B_{ijk}/B_{total}$, then the bin is uncertain, and if $M_{ijk}/M_{total} = B_{ijk}/B_{total} = 0$, the bin is unpopulated.

Extrapolating to Increase Number of Assigned Bins in H

Figure 27:
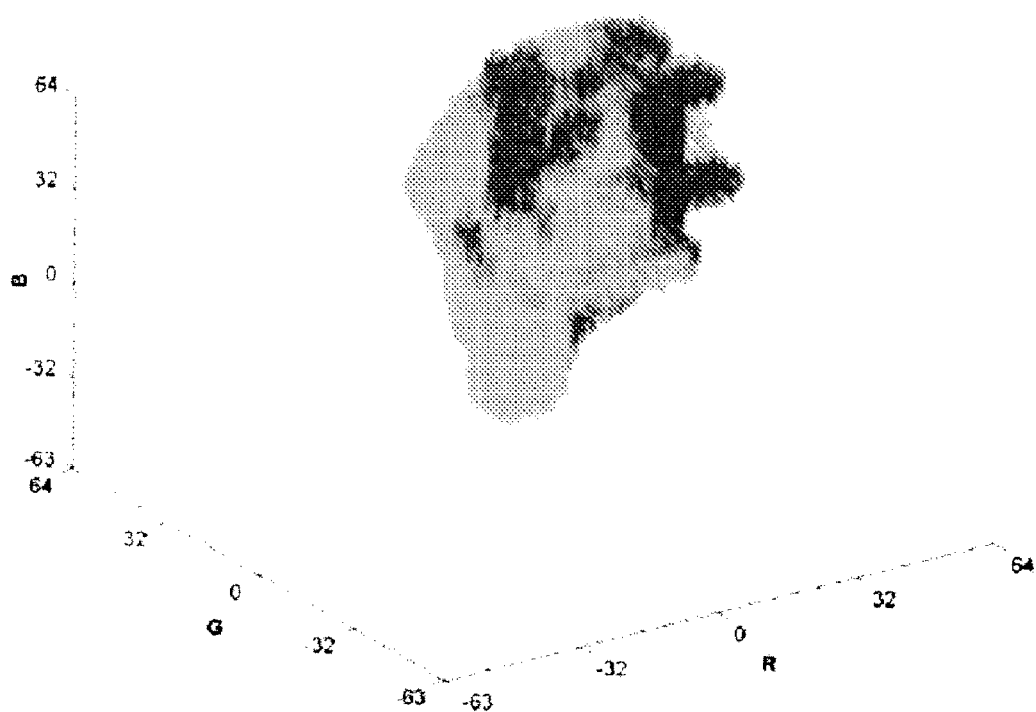
FIG. 27 shows three-dimensional relative color histogram bin labeling for a training set of images. The gray regions are melanoma-labeled bins. The black regions are benign-labeled bins.

A large number of bins $b_{ijk}$ remain unpopulated or uncertain, even after training runs with large sets have populated H. To assess colors from test images that may fall in these bins, extrapolation was used. Parameters for extrapolation were optimized to yield the following algorithm. For each uncertain or unpopulated bin $b_{ijk}$ in the quantized H, a count is made of the adjacent neighboring benign bins to yield $count_B$ and corresponding malignant bins $count_M$. Note that neighbors are considered in three dimensions. For most bilk, those bins not on the periphery of H, there are 26 adjacent neighbors, but for $b_{ijk}$ on a face of H, there are 17 neighbors for $b_{ijk}$, and similarly 11 neighbors on an edge of H and 6 on a corner of H. Change $b_{ijk}$ to a malignant bin if $count_M \geq 1$ and $count_B = 0$ or $count_M - count_B \geq 3$. Change to a benign bin if $count_B \geq 1$ and $count_M = 0$ or $count_B - count_M \geq 5$. Iteration is stopped after additional conversions are negligible, which always occurs after extending extrapolation 10 bins from the mapped bins. An example of the quantized histogram H showing benign and malignant bins after this process is completed is shown in FIG. 27, which shows three-dimensional relative color histogram bin. The black regions are benign-labeled bins.

Percent Melanoma Color Feature

The melanoma color percentage feature P is the percent of the lesion with pixels that fall within the malignant region of H. If $P \geq D$, the lesion is scored malignant. D is chosen so that the true positive (tp) and true negative (tn) training set rates are equal. D is increased in increments of 0.01 from 0 to 1. For each $D_i$, for i=1 to 100, the true positive rate $tp_i$ (fraction of melanomas correctly diagnosed) and the true negative rate $tn_i$ (fraction of benign lesions correctly diagnosed) are determined from the training images. The threshold D is selected to minimize the difference between tp and tn, choosing tn as close to tp as possible with $tn \leq tp$: $D = \{D_i | 0 \leq (tp_i - tn_i) \leq (tp_j - tn_j), i,j \in (1, \ldots, 100)\}$.

Melanoma Color Index Feature MI

The melanoma color index MI may be applied to any structure or region. This index is the average of the bin score over a structure. The melanoma bin score is the normalized count$_M$ and the benign bin score is the normalized count$_B$, where count$_M$ and count$_B$ are counts of images with pixels with the relative color denoted by that bin color. Normalization of count$_M$ and count$_B$ is accomplished by dividing the unnormalized counts by the number of malignant and benign images in the entire training set, respectively. In addition, a ratio (normalized count$_M$)/(normalized count$_B$) may be used to represent a third melanoma color index. The melanoma color indices may be made fuzzy, with a membership function based on the bin score.

Crisp Melanoma Color Clustering Feature

The color clustering ratio feature (Stanley03) provides a quantitative measure of the grouping of malignant pixels within the lesion. Let M denote the set of relative color values that map into quantized histogram bins labeled as melanoma colors from the training set of images. Let L denote the set of pixel locations within the lesion with relative color O that map into melanoma colors: L={(x,y)|O$_{rel/(x,y)}$∈M}. Let N$_{(n,y)}$ denote the number of eight-connected neighbors and N$_{M(x,y)}$ denote the number of melanoma-colored eight-connected neighbors that are contained in the lesion for pixel (xy)∈L. Then, $$S = \sum_{(x,y) \in L} N_{M(x,y)}$$

represents the total number of melanoma color neighbors for all pixels within the skin lesion with relative color values that map as melanoma colors. The cumulative total number of eight-connected neighbors, for all (x,y)∈L, regardless of whether the neighbors have malignant mapping, is denoted as $$T = \sum_{(x,y) \in L} N_{(x,y)}.$$

The color clustering ratio C for a lesion is given as $$C = \frac{S}{T}.$$

If C≧K, the lesion is scored malignant. K is chosen so that the true positive (tp) and true negative (tn) training set rates are as equal as possible with tn≦tp while iterating from 0 to 1 in increments of 0.001.

Preliminary Calculations for Fuzzy Clustering Ratio

A. Surrounding Skin Determination

To eliminate pixels (red, green, blue) that are non-skin-colored, and those that are in deep shadow and those that represent direct reflection of the flash, several empirical relationships were determined. The skin pixel finder used in this research was derived from an existing dermatology image database under the guidance of a dermatologist and has been applied to skin lesion analysis in other research (Faziloglu03, McLean94). Surrounding skin color was approximated using a uniform region of 20% of the lesion's area immediately surrounding the skin lesion. The surrounding skin region size was determined as a function of the skin lesion size (Hance96, McLean94). The average surrounding skin color ($r_{skin}, g_{skin}, b_{skin}$) is computed within the circular region that is outside of the lesion, excluding the non-skin-colored pixels.

B. Color Histogram Bin Determination

The fuzzy logic-based techniques developed in this research are based on relative color-based histogram analysis. The relative color skin lesion image region O$_{rel}$ can take on the integer values in the range [−255,255] for R, G and B. Thus, the color histogram has 511$^3$ total bins. Requantizing the relative RGB histogram bins is appropriate to represent discrete ranges of colors that are characteristic of melanoma and benign skin lesions. In this research, we are interested in applying benign skin colors to color feature determination. The 511×511×511 relative color histogram is requantized to include 64 distinct colors in each histogram bin. This is done by dividing each relative color range by 4, yielding a 128×128×128 relative color histogram that is used for analysis.

Let C denote the set of relative color bins, and let C$_{(x,y)}$ denote the relative color bin into which the skin lesion pixel (xy) maps. Because there are 511 relative colors for R, G and B, dividing by 4 will result in histogram bins containing 4×4×4 relative colors, except for some bins on the edges of the cube that are 4×4×3 and one bin in the corner of the cube that is 3×3×3. Based on examining the training relative color histograms for the data set used in this research, the bin containing −255 for R, G and B was chosen to have only three color levels in each dimension (3×3×3) because of the unlikelihood of its occurrence in clinical images.

Color Histogram Analysis Technique

A. Fuzzy Set Description for Trapezoidal Membership Function

A fuzzy logic-based approach is used for representing relative skin lesion color. Specifically, let B denote the fuzzy set (Klir88) with a trapezoidal membership function for relative skin lesion color, for the specified skin lesion class. The following procedure was used to assign membership values to the colors within the color histogram bins defined above under the heading, "Preliminary Calculations for Fuzzy Clustering Ratio, A. Surrounding Skin Determination." Using batch mode, the training set of images for the specified class is used to populate the three-dimensional relative color histogram bins, where each bin contains the sum of all skin lesion pixels over all training images with relative color mapping to that bin. A secondary histogram is defined as a histogram of the three-dimensional relative color histogram. The secondary histogram is a function of x which indicates the number of bins of the three-dimensional relative color histogram that are populated with x lesion pixels summed over all benign images in the training set.

The fuzzy set B is determined based on the benign skin lesion training data. Membership values are assigned continuously for each count in the secondary histogram for the relative colors, for the specified class. For secondary histogram bin frequency count x, the membership function μ$_B$(x) denoting the fuzzy set (Klir88) is given as $$\mu_B = \begin{cases} x/F & \text{for } 0 \le x < F \\ 1 & \text{for } x \ge F. \end{cases}$$

F is empirically determined as the frequency count such that 5% of the total bins comprising the secondary histogram have frequency F or greater, and x represents the number of hits in a bin over the training set of benign images. The membership values are reflective of increasing membership in the specified class of skin lesions with increasing frequency count.

B. Fuzzy Clustering Ratio Determination

In a given skin lesion, the pixels with relative colors that had at least a certain degree of membership in the relative color fuzzy set B are used for feature calculation. Let $|\alpha_B|$ denote the cardinality of the $\alpha$-cut, i.e. the number of lesion pixels where $\mu_B(C_{(x,y)}) \geq \alpha$, for a specified $\alpha$ on B (Klir88). Let S(B) refer to the support of B, where $$S(B) = \{(x,y): \mu_B(C_{(x,y)}) > 0 \text{ for } (x,y) \text{ contained in the skin lesion}\},$$

and let |S(B)| denote the cardinality of S(B), that is, the number of pixels within the skin lesion with nonzero membership in B (Klir88).

The fuzzy clustering ratio feature gives an indicator of the grouping of pixels within a lesion region that have at least a specified level of confidence as being associated with benign skin lesions. The fuzzy clustering ratio feature is computed as follows. Let M denote the set of relative color values that map into relative color histogram bins labeled with $\mu_B(C_{(x,y)}) \geq \alpha$, for a specified $\alpha$ on B and (x,y) contained in the skin lesion. Let P denote the set of relative color values that map into relative color histogram bins labeled with $\mu_B(C_{(x,y)}) > 0$ and (x,y) contained in the skin lesion. Let L denote the set of pixel locations within the skin lesion region of interest with relative color O that map into M, formally $L = \{(x, y) | O_{rel(x,y)} \in M\}$. Let $N_{(x,y)}$ denote the number of eight-connected neighbors and $N_{M(x,y)}$ denote the number of eight-connected neighbors that are contained in the lesion region of interest for pixel $(x,y) \in L$. The eight-connected neighbors for $(x,y) \in L$ that lie outside of the lesion region of interest are excluded from calculating $N_{(x,y)}$ and $N_{M(x,y)}$. Then, $$S = \sum_{(x,y) \in L} N_{M(x,y)}$$

represents the total number of melanoma color neighbors for all pixels within the skin lesion with relative color values that map as melanoma colors. The cumulative total number of eight-connected neighbors for all $(x,y) \in L$ is denoted as $$T = \sum_{(x,y) \in P} N_{(x,y)} \cdot T$$

includes all neighbors of melanoma color pixels within the skin lesion regardless of whether the neighbor is mapped to a melanoma color. The color clustering ratio for a skin lesion is given as $$R(\alpha) = \frac{S(\alpha)}{T}.$$

Note that $R(\alpha)$ is computed based on the pixels within the skin lesion. The surrounding skin pixels are only used for computing the average surrounding skin color for determining the relative color of all pixels within the skin lesion. Thus, for $\alpha = 0$, $R = 1$, provided that at least one pixel within the skin lesion has a non-zero membership value in B. If B represents the fuzzy set for benign skin lesion relative color as determined from the training set of images, then $R(\alpha)$ represents the degree to which the benign colors within the skin lesion are the colors perceived to be associated with benign skin lesions. As $\alpha$ is increased, $^\alpha B$ contains pixels that are more strongly perceived as benign lesion pixels.

Benign image training data are used to determine relative color histogram bin membership in B. The next step is to compute $R(\alpha)$ for all benign and melanoma skin lesions from the training data for a specified value of $\alpha$. A threshold T is automatically determined from the ratios $R(\alpha)$ calculated from the training data. The procedure for finding T is presented in the following section.

Skin lesions are categorized as either benign or melanomas for the data set used in this research. A given skin lesion is classified as benign if $R(\alpha) > T$. Otherwise, the skin lesion is labeled as a melanoma.

B. Threshold Determination Procedure

The ratios $R(\alpha)$ computed from the training data were sorted to facilitate automated threshold (K) selection. The approach used for automatically selecting K for a particular $\alpha$ is based on computing the true positive and true negative rates for the training data. The procedure for choosing the optimal K involves iterating K through the sorted ratios $R(\alpha)$ from [0,1] in increments of 0.001. For each K, the true positive and true negative rates, denoted as tp and tn, are determined from the training images. K is chosen as the threshold where the tp=tn.

It is possible that the true positive and true negative rates do not become equal over the threshold iteration process due to the discrete training set and to differences in the training true positive and true negative rates. In this situation, K is determined as follows. If, while iterating, threshold $K_i$ results in tp<tn, and the next threshold $K_{i+1}$ (in the threshold iteration process) yields tp>tn, then $K_i$ is selected as the threshold. The other possibility is if, while iterating, threshold $K_i$ generates tp>tn, and the next threshold $K_{i+1}$ (in the threshold iteration process) yields tp<tn, then $K_{i+1}$ is chosen as the threshold. The final melanoma and benign lesion classification results are obtained for the training and the test data using the final threshold K. The procedure is repeated for specified $\alpha$ values.

Physiologic Melanoma or Benign Color Descriptor

The relative color histogram is mapped for melanoma and benign regions. The histogram region with highest relative red, for example, is benign (FIG. 27). Melanoma red is therefore really pink and not highly saturated and includes an admixture of brown. The melanoma red region is thus not as red as the benign red region. Mapping determines border bins for regions, with enclosed 26-connected regions for melanoma colors having a melanoma color index (normalized ratio of melanoma pixels to benign pixels) that is greater than a threshold K, where K is optimized. The physiologic melanoma colors are white, gray, dark brown, blue, pink, red-brown, light brown, and brown-black. The physiologic benign colors are tan, brown and red. These color region descriptors are used in the concentric color blotch vector.

Concentric Color Blotch Vector

To compute the concentric color vector feature, the color pixels are averaged over 4×4 blocks. A median split algorithm operating upon the relative color histogram is modified to split the lesion into 1-6 colors, with one or more regions for each color. For a 3-color split, for example, the red relative color histogram is divided into three equally populated regions, with low, medium and high relative red values in the 4×4 blocks of the original lesion. After the lesion is split into n colors, $1 \leq n \leq 5$, if intra-region variance is below an empirically optimized limit, the routine quits, otherwise the lesion is split into n+1 regions and variance is again computed. Concentric decile ring areas are then computed for the lesion, with the first decile the inner 10% of points, and the $10^{th}$ decile the outer 10% of points. The feature vector for each decile includes for each color region, up to 6 regions 1) relative RGB histogram color or physiological color for the region; 2) fraction of lesion decile occupied by the color region; 3) melanoma color confidence level for the color; 4) color eccentricity: scaled distance between color region centroid and lesion centroid; 5) Melanoma color index MI. Classifier training optimizes the number and range of concentric rings. The configuration inner 30%, next 20%, next 20%, next 20% and outer 10% is a highly physiological division, but other optimal divisions may be used. The advantage to this representation is that specific benign patterns for dysplastic nevi such as the peripheral ring pattern (dark network outside) and fried egg pattern (dark network or dark blotch in the center) can be represented as a vector. The peripheral ring pattern is often C-shaped, with that representation appearing in the vector components 1) and 4), showing a tan color and a scaled distance between centroids computed as a small fraction of a lesion radius in the outer two decile rings. Additional patterns, including malignant patterns such as central or peripheral scar-like depigmentation can be represented.

Regression: Scar-like Depigmentation

Figure 28:
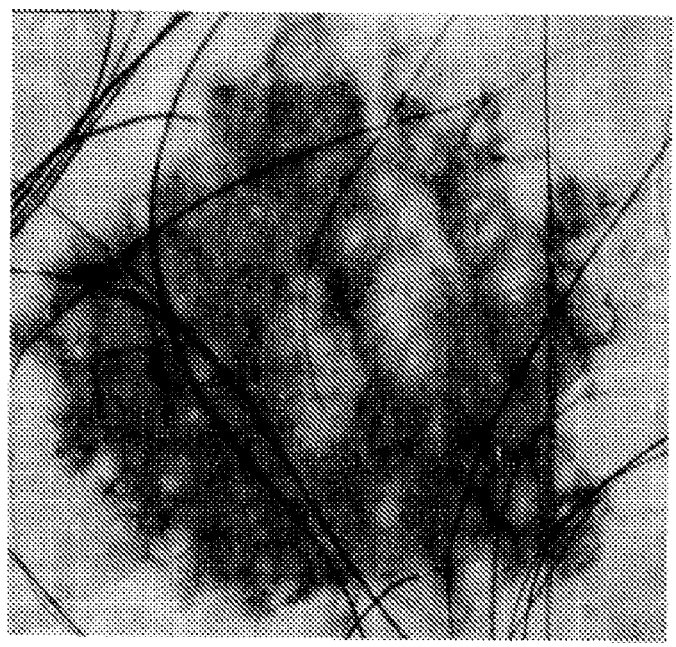
FIG. 28 shows an image with areas of scarlike depigmentation.
Figure 29:
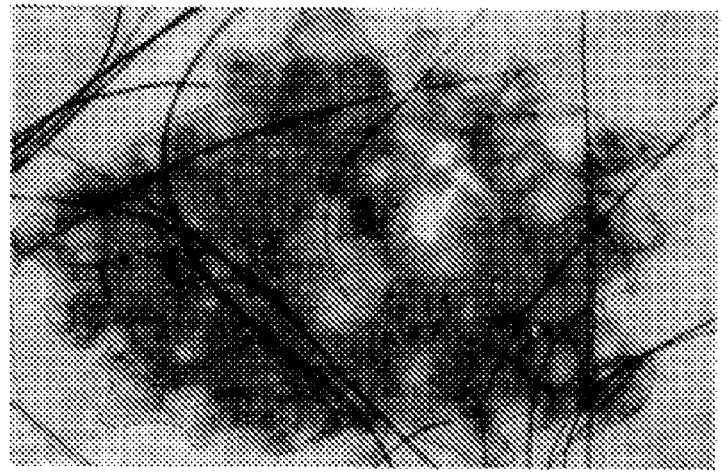
FIG. 29 shows an image produced by a method of scarlike depigmentation detection showing automatically-detected scar-like candidate areas using our method.

Regression structures are light structures, lighter than the surrounding skin, and contained within lesions such as melanomas in situ. These were found useful by Massi (Massi01) and yield an odds ratio overall for melanoma of 5.4, $3^{rd}$ of 24 pattern analysis features (Argenziano03). The pathologic significance of this feature is "loss of pigmentation and fibroplasia, with scattered dermal melanophages in early melanoma" (Argenziano98). Examining 200 lesions for areas found automatically (FIGS. 28 and 29) shows that our scar-like depigmentation detection, using four color algorithms, is accurate. The prior art of Tatikonda (Tatikonda02) in finding scar-like depigmentation provides almost no diagnostic separation, thus additional steps are needed. The following paragraph details the method used as post-processing for Tatikonda-detected scar-like depigmentation areas (FIGS. 28 and 29). Scar-like depigmentation is combined with granularity by seeking proximity of the two features.

Figure 30:
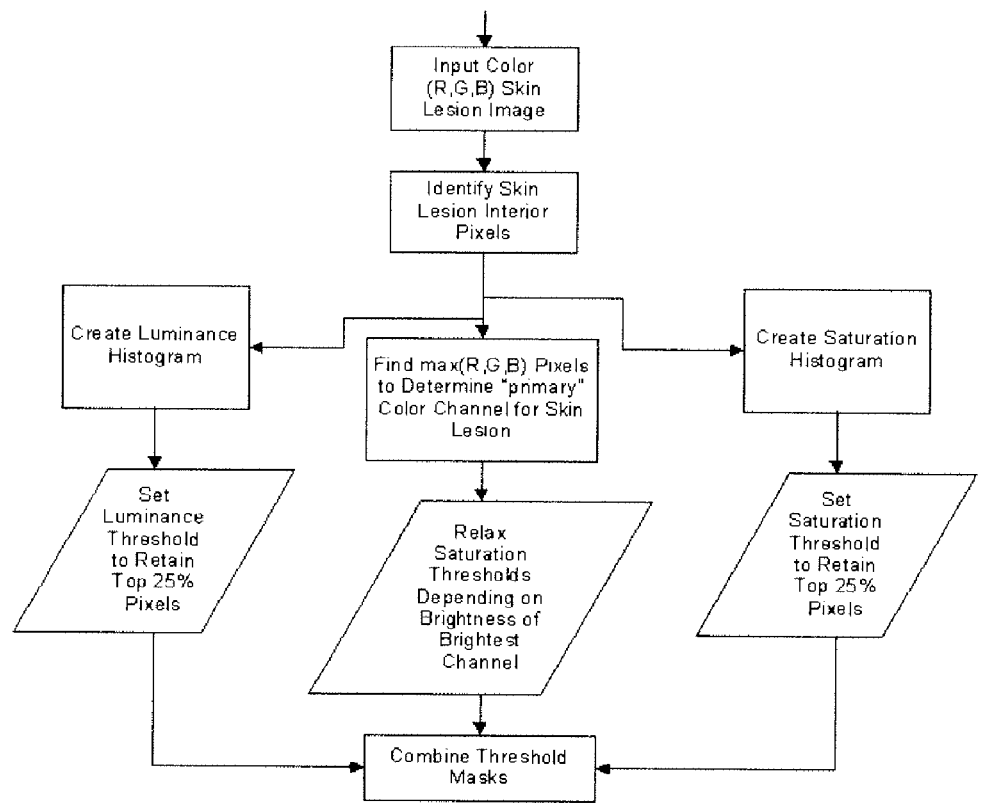
FIG. 30 is a flowchart showing a prior art for screening algorithm for scar-like depigmentation detection in dermoscopic images.

Four algorithms from Tatikonda with one of the four represented in FIG. 30 comprise our method and are used to screen for significant candidate scar-like depigmentation areas within interior lesion pixels (at least 50 pixels from the lesion boundary). The other demands placed on the detected areas include 1) proximity to granularity detected by the previous section; 2) size of both granularity and scar-like depigmentation areas; 3) presence of scar-like depigmentation within a paracentric lesion concentricity decile region optimized by classifier analysis and optimizing the ROC curve results using the concentricity decile of the Tatikonda structures; 4) absence of a halo detected automatically via relative color analysis; 5) satisfaction of luminance and histogram analysis thresholds.

Granularity

Granularity or "peppering" is a feature characterized by a noisy grayish pixel pattern often found in or near areas of regression. Granularity is useful in detecting melanoma in situ. The granular regions contain a critical texture that is detected by first screening using the method of prior art from Tatikonda (Tatikonda02). Granularity detection yields candidate areas that are used in combination with scar-like depigmentation as below.

Salient Point Detection

Steger's method of line detection (Steger96) models pigment network lines as ridges and applies line detection using the Hessian matrix, following Steger's method of 2D line extraction (Fleming98). Five candidate planes for the optimal grayscale image plane were examined: 1) the blue (third) plane of the RGB image 2) the x-CIE (first plane of the CIExyz image 3) the intensity image (R+G+B)/3, 4) the luminance image (0.29R+0.59G+0.11B) and 5) the first plane of the principal component (PCT) image. The blue plane over-identified network regions and the intensity image at sigma=1.02 was found to best represent the networks in terms of salient points, although the other three planes produced results similar to the intensity plane. Line centers are characterized as having a vanishing first derivative and a high second derivative perpendicular to the line. This direction is specified by the eigenvector corresponding to the largest eigenvalue of the Hessian matrix:

$$H(x, y) = \begin{pmatrix} r_{xx} & r_{xy} \\ r_{xy} & r_{yy} \end{pmatrix},$$

where $r_{xx}$, $r_{xy}$ and $r_{yy}$ are partial derivatives of the image obtained by convolution with derivatives of Gaussian smoothing kernels. Approximating the image with the second-order Taylor polynomial fit to the image at each point, setting the derivative along the line to zero, substituting and solving yields subpixel location of critical points on the center of the line that are called salient points. Thresholding by choosing sigma in the Gaussian smoothing function allows filtering for high-likelihood line points.

The identification of the intensity plane (R+G+B)/3, the x-CIE (first plane of the CIExyz image, the luminance plane (0.29R+0.59G+0.11B) and the first plane of the principal component (PCT) image as satisfactory planes for salient point detection is new. The intensity plane at Gaussian sigma 1.02 is optimal, but sigma may vary from 0.9 to 1.2.

The salient points fail to identify the critical network areas unless several types of preprocessing were applied. We apply the relative-color blotch mask ($R_{skin}$–R>140) OR (($R_{skin}$–R>110) AND ($G_{skin}$–G>140)) to eliminate those areas from salient point detection. We eliminate false dark border areas by demanding all R, G and B>20. We apply a telangiectasia mask to eliminate vessels by demanding that no candidate salient point pixel has a drop of G>57 from background and R<28 from background. We eliminate bubbles from the candidate salient points by demanding that R<230, G<230, B<230); these numbers can vary up or down. For any given set of images, if a bubble pixel typically exceeds X luminance, then X works as a threshold for that image set. Typically X=230 eliminates the bubble pixels without eliminating other non-flash and non-liquid surfaces, but 230 may be adjusted up or down by as many as about 20 gray-scale values for different equipment and lighting conditions.

The salient point statistics are computed over squares of size K×L, where K and L are odd integers. K=L is optimized at 27, but can range from 23 to 39. The following variables are given to an ANN: block mean, median, and standard deviation, and each of these divided by the average intensity for the block. A seventh variable is the product of the standard deviation and the square of the intensity.

The salient point statistics fail to identify melanomas significantly unless the salient point determination is made on the outer K % of the lesion, where K is 10%, with a range of 4% to 20%.

Figure 31:
FIG. 31A shows an image with bubbles.
FIG. 31B shows the image after application of the salient point mask to detect bubbles.
Figure 31:
Figure 32:
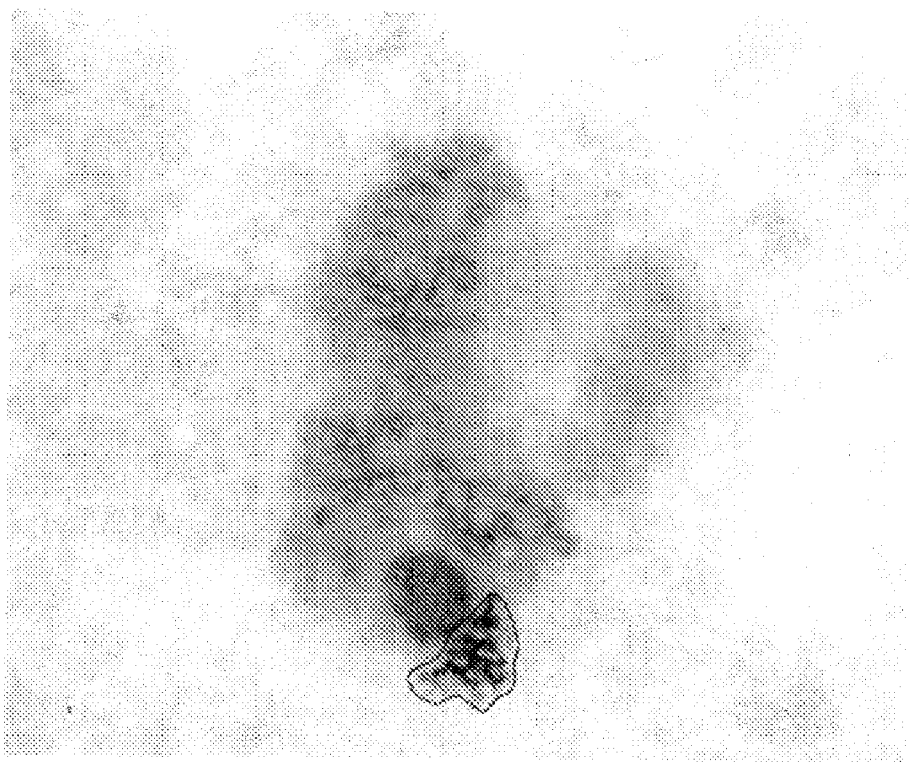
FIG. 32 shows an area of atypical pigment network in this image of a melanoma (Argenziano00). Note that the atypical pigment network in this image is in the darkest part of the image, and displays the widened pigment network lines as well as varying hole signs expected for an atypical pigment network.
Figure 33:
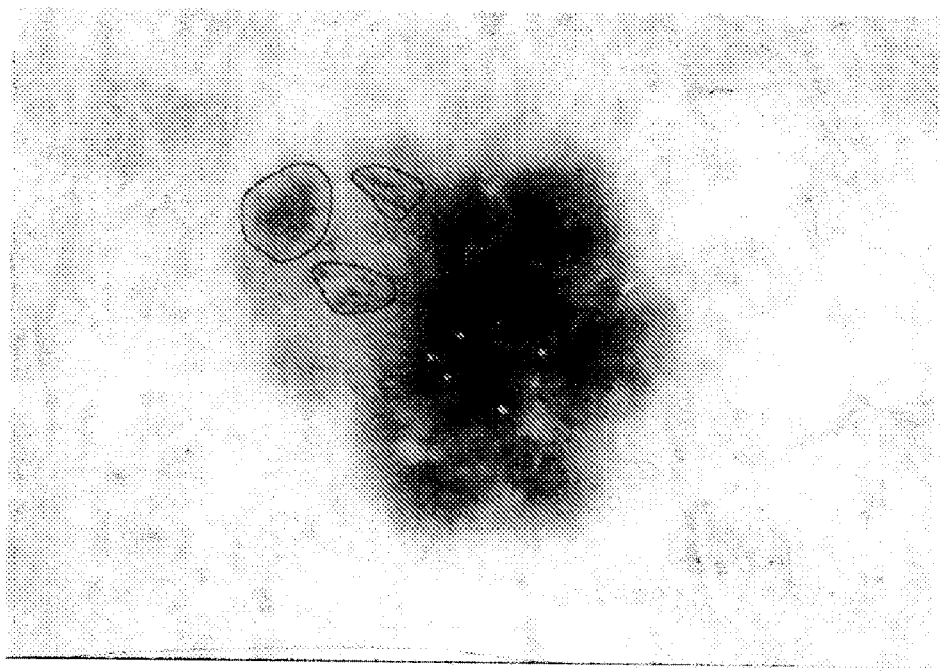
FIG. 33 shows several areas of atypical pigment network in this image of a melanoma (Argenziano00). For this lesion, the area of atypical pigment network is not in the darkest part of the lesion, and thus is not detectable by darkness but by comparing texture measured over different areas of the lesion.
Figure 34:
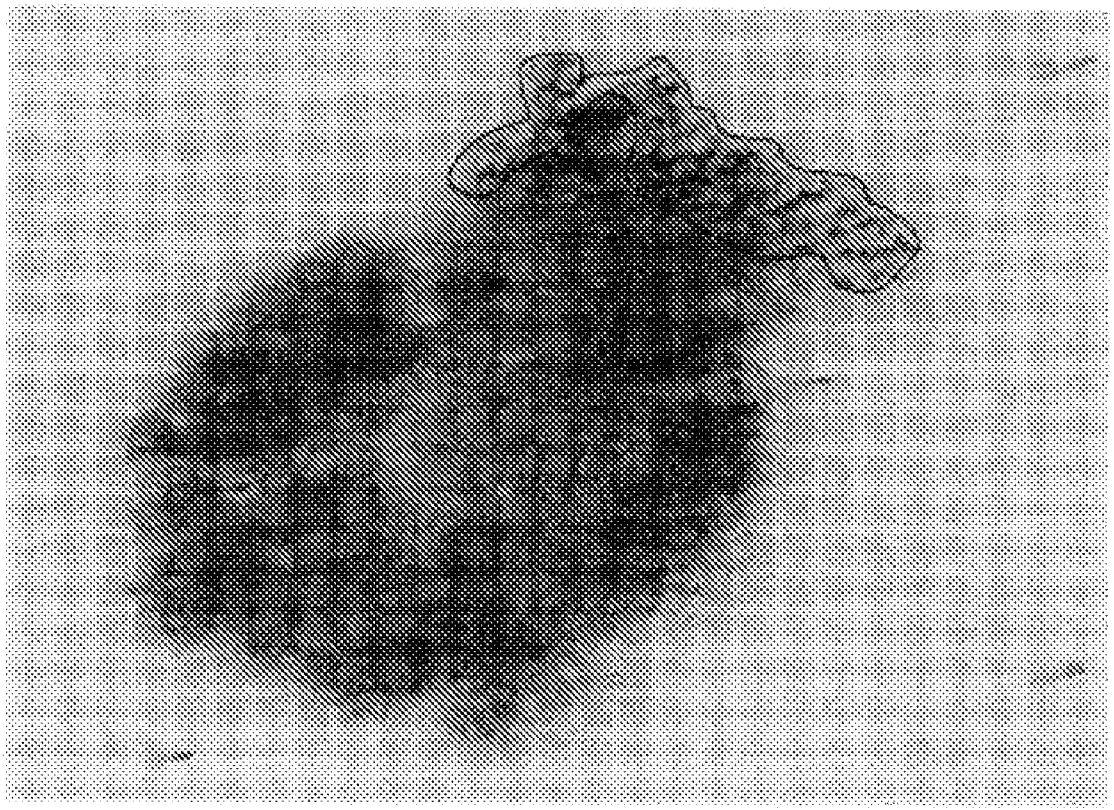
FIG. 34 shows dark atypical pigment network in this image of a melanoma (Argenziano00), not the darkest part of the lesion, and not detectable by darkness but by comparing texture measured over different areas of the lesion. (Argenziano00).

Salient Point Detection Applied to Bubble Detection and Other Structure Detection The salient points, with typical values as noted previously (typical sigma=1.02 applied to the intensity image) may be used to identify bubbles as noted above. With adequate brightness screening, bubbles may be identified. The salient point mask in FIG. 31B applied to the image in FIG. 31A shows identification of bubbles. Bubbles are automatically detected, (along with border and other sharp structures), sigma=1.02 applied to intensity plane. Bubbles may be isolated by brightness and digital hair removal algorithm mask demands. Concomitant screening using the modified digital hair removal algorithm mask can be applied. Salient point masks may be used with another color plane optimized for detection of fine irregular blood vessels. This allows detection of the telangiectasia and when combined with shape analysis, allows the detection of the irregular linear blood vessels seen with amelanotic melanoma.

Salient Point Detection and Other Methods for Irregular Pigment Network Detection Statistics of salient points, as detailed above, are used to detect irregular pigment network, comprising an alternative method to the co-occurrence matrix measures as in the correlation mean and range methods above. It is also possible to identify irregular or atypical pigment network by applying texture classifiers such as Laws (optimized to a combination of Laws 9×9 and 11×11 (Laws80, Anantha04) but these filters can vary in size from 3×3 to 21×21).

Clinical Features

Seven clinical features are obtained and input to the system: patient age, gender, lesion location (face, ears, scalp, neck, arm, leg, trunk, anogenital, hand, foot), childhood sunburns, recent lesion onset/change, family history of melanoma (including melanoma in situ, 1 st degree relative), and personal history of melanoma (including melanoma in situ).

Training Endpoints

The system is trained with a classifier such as an Artificial Neural Network (ANN) to optimize discrimination of diagnoses into two classes for each of two endpoints:

ENDPOINT NUMBER ONE—NEED FOR BIOPSY, TWO CLASSES: 1) Need for biopsy of pigmented lesion: diagnosis of at least dysplastic nevus with architectural disorder and moderate or severe cytologic atypia, cellular blue nevus, deep penetrating nevus or Spitz nevus; 2) No need for biopsy of pigmented lesion: junctional, compound, or intradermal nevus, dysplastic nevus with architectural disorder and mild cytologic atypia, lentigo, blue nevus.

ENDPOINT NUMBER TWO—MALIGNANT PIGMENTED LESION, TWO CLASSES: 1) Melanoma or melanoma in situ; 2) junctional, compound, or intradermal nevus, dysplastic nevus with architectural disorder and mild cytologic atypia, lentigo, blue nevus.

This invention has been described and exemplified with reference to specific algorithms, method steps and features; however, as will be understood by one of skill in the art, equivalents may be used, and the claims should be interpreted to include such equivalents.

REFERENCES

Anantha04 Anantha M, Moss R H, Stoecker W V: "Detection of pigment network in dermatoscopy images using texture analysis." Comput Med Imaging Graph. 28(5):225-34, 2004.

Argenziano98 Argenziano G, Fabbrocini G, Carli P, et al. Epiluminescence microscopy for the diagnosis of doubtful melanocytic skin lesions. Comparison of the ABCD rule of dermatoscopy and a new 7-point checklist based on pattern analysis. Arch Dermatol. 1998 134(12):1563-70.

Argenziano00 Argenziano G, Soyer H P, De Giorgi V et al: Dermoscopy, an Interactive Atlas. EDRA Medical Publishing, Milan Italy, Argenziano03 Argenziano G, Soyer H P, Chimenti S et al. Dermoscopy of pigmented skin lesions: Results of a consensus meeting via the Internet. J Am Acad Dermatol 48(5):679-93, 2003.

Binder95 Binder M, Schwarz M, Winkler A, et al. Epiluminescence microscopy. A useful tool for the diagnosis of pigmented skin lesions for formally trained dermatologists. Arch Dermatol 131: 286-291, 1995.

Binder00 Binder M, Kittler H, Dreiseitl S, et al: Computer-aided epiluminescence microscopy of pigmented skin lesions: the value of clinical data for the classification process. Melanoma Res. 10(6):556-61, 2000

Bleau00 A. L. Bleau and L. Joshua, "Watershed-based segmentation and region merging," Computer Vision and Image Understanding, vol. 77, no. 3, pp. 317-370, 2000.

Bono02 Bono A, Bartoli C, Baldi M, Tomatis S, Bifulco C, Santinami M. Clinical and dermatoscopic diagnosis of small pigmented skin lesions. European Journal of Dermatology 12(6):573-576, 2002.

Breiman01 Breiman L: "Random Forests," Machine Learning, vol. 45, no. 1, pp. 5-32, 2001.

Carli99 Carli P, De Giorgi V, Soyer H P. Epiluminescence microscopy in the management of pigmented skin lesions. www.dermoscopy.org/cme_article.htm 1999.

Carli00 Carli P, De Giorgi V, Soyer H P, Stante M, Mannone F, Giannotti B. Dermatoscopy in the diagnosis of pigmented skin lesions: a new semiology for the dermatologist. J Eur Acad Dermatol Venereol. 2000, 14(5):353-69.

Celebi06 M. Emre Celebi M E, Aslandogan Y A, Stoecker W V, Iyatomi H, Oka O, and Chen X: "Unsupervised border detection in dermoscopy images." Skin Res and Technology, 2006 (accepted for publication).

Chen05 Chen X, Moss R H, Stoecker W V, Stanley R J, Lee T, Hvatum E, McLean D. Software improvements in hair detection using DullRazor. Poster presented at 6th World Melanoma Congress, Vancouver, 2005.

Cotton96 Cotton S D, Claridge E: Developing a predictive model of human skin colouring. Vanmetter R L, Beutel J (Eds). Proceedings of the SPIE Medical Imaging 1996 2708: 814-825, 1996.

Cotton99 Cotton S D, Claridge E, Hall P: A skin imaging method based on a colour formation model and its application to the diagnosis of pigmented skin lesions. Proceedings Medical Image Analysis and Understanding 99, Oxford: BMVA, 49-52, 1999.

Dal Pozzo99 Dal Pozzo V, Benelli C, Roscetti E. The seven features for melanoma: a new dermoscopic algorithm for the diagnosis of malignant melanoma. Eur J Dermatol 9: 303-8, 1999.

De Boor01 de Boor C: A Practical Guide to Splines (Second Edition). New York, N.Y.: Springer-Verlag New York Inc., 2001

Eddins02 Eddins S, "The watershed transform, strategies for image segmentation," The Mathworks Journal, Matlab® News and Notes, February, 2002.

Elbaum01 Elbaum M, Kopf A, Rabinovitz H, et al. Automatic differentiation of melanoma from melanocytic nevi with multispectral digital dermoscopy: A feasibility study, J Amer Acad Dermatology 44(2): 207-218, 2001.

Erkol05 Erkol B, Moss R H, Stanley R J, Stoecker W V, and Hvatum E, Automatic Lesion Boundary Detection in Dermoscopy Images Using Gradient Vector Flow Snakes, Skin Research and Technology, 11 (1): 17-26, 2005.

Faziloglu03 Faziloglu Y, Stanley R J, Moss R H, Stoecker W V, McLean R. Colour histogram analysis for melanoma discrimination in clinical images. Skin Res Technol. 2003 May; 9(2):147-56.

Felkel01 Felkel, P: "Implementation and complexity of the watershed-from-markers algorithm computed as a minimal cost forest," Computer Graphic Forum, VrVis Center, Lothringerstrabe, Vienna, Austria 2001.

Fleming98 Fleming M G, Steger C, Zhang J, Gao J, Cognetta A B, Pollak L, Dyer C R. Techniques for a structural analysis of dermatoscopic imagery. Comput Med Imag Graph 22: 375-389, 1998.

Gomez06 Gomez D G, Butakoff C, Ersboll B K, Stoecker W V Independent histogram pursuit for segmentation of skin lesions. Submitted to IEEE Trans Medical Imag, 2006.

Hance96 Hance G A, Umbaugh S E, Moss R H, Stoecker W V: S.E. "Unsupervised color image segmentation with application to skin tumor borders," IEEE Eng. Med. Biol., vol. 15, no. 1, pp. 104-111, 1996.

Haralick73 Haralick R M, Shanmugam K and Dinstein I, Textural features for image classification. IEEE Transactions on Systems, Man and Cybernetics, 3, 1973, pp 610-621.

Hoffman03 Hoffmann K, Gambichler T, Rick A. Diagnostic and neural analysis of skin cancer (DANAOS). A multicentre study for collection and computer-aided analysis of data from pigmented skin lesions using digital dermoscopy. Br J. Dermatol. 2003 October; 149(4):801-9.

Jamora03 Jamora M J, Wainwright B D, Meehan S A et al. Improved identification of potentially dangerous pigmented skin lesions by computerized image analysis. Arch Dermatol. 139(2):195-8, 2003.

Jemal06 Jemal A, Siegel R, Ward E et al., Cancer Statistics 2006. Ca-A Cancer for Clinicians 56:06-130, 2006.

Kittler99 Kittler H, Seltenheim M, Dawid M, et al. Morphologic changes of pigmented skin lesions: a useful extension of the ABCD rule for dermatoscopy. J Am Acad Dermatol 40:558-62, 1999.

Klir88 Klir G J, Folger T A. Fuzzy Sets, Uncertainty and Information, Englewood Cliffs, N.J., Prentice-Hall, 1988.

Laws80 Laws, K. I. Textured image segmentation. Ph.D. dissertation. University of Southern California, Los Angles, Calif. January 1980. USCIPI Report #940.

Lee97 Lee T, Ng V, Gallagher R et al. DullRazor: a software approach to hair removal from images. Comput Biol Med. 27(6):533-43, 1997

Mangan98 Mangan A P and Whitaker R. "Surface segmentation using morphological watersheds," IEEE Visualization '98: Late Breaking Topics, pp. 2932, October 1998

Massi01 Massi D, De Giorgi V, Carli P, Santucci M, Diagnostic Significance of the Blue Hue in Dermoscopy of Melanocytic Lesions: A Dermoscopic-Pathologic Study, American Journal of Dermatopathology 23(5): 463-469, 2001.

McLean94 McLean, R classification based on relative color analysis of melanoma and non-melanoma tumor images. MS Thesis, 1994, Department of Electrical Engineering, University of Missouri, Rolla.

Menzies96b Menzies S W, Ingvar C, Crotty K A, et al. Frequency and morphologic characteristic of invasive melanomas lacking specific surface microscopic features. Arch Dermatol 132:1178-82, 1996.

Moncrieff01 Moncrieff M, Cotton S, Hall P, et al. SIAscopy assists in the diagnosis of melanoma by utilizing computer vision techniques to visualize the internal structure of the skin. In Med Image Understanding Analysis, 2001, Claridge E, Bamber J, Marlow K (Eds.), York, UK, p. 53-56.

Moncrieff02 Moncrieff M, Cotton S, Claridge E et al. Spectrophotometric intracutaneous analysis: a new technique for imaging pigmented lesions. Br J Dermatol. 2002; 146: 448-457.

Nachbar94 Nachbar F, Stolz W, Merkle T, et al. The ABCD rule of dermatoscopy. J Am Acad Dermatol 30: 551-9, 1994.

Pagadala98 Pagadala P. Tumor border detection in epiluminescence microscopy images. M.S. Thesis, Department of Electrical Engineering, University of Missouri-Rolla, 1998.

Rabinovitz01 Rabinovitz H, director. Information presented at the Dermoscopy Course. MD Annual meeting, March 2001.

Rosado03 Rosado B, Menzies S, Harbauer A et al. Accuracy of computer diagnosis of melanoma. A quantitative meta-analysis. Arch Dermatol. 139:361-367, 2003.

Rubengni02 Rubegni P, Burroni M, Cevenini G et al: Digital dermoscopy analysis and artificial neural network for the differentiation of clinically atypical pigmented skin lesions: a retrospective study. J Invest Dermatol 119:471-474, 2002.

Seidenari06 Seidenari S. Differentiating common nevi from atypical nevi and melanoma in situ. First Congress of the International Dermoscopy Society, Naples, Italy, Apr 27-29, 2006. Abstract: Dermatology 2006; 212:279.

Soille03 P. Soille P: Morphological Image Analysis: Principles and Applications, 2nd ed., Springer-Verlag, Heidelberg, Germany, 2003. p. 198

Stanley03 Stanley R J, Moss R H, Stoecker W V, Aggarwal C. A fuzzy-based histogram analysis technique for skin lesion discrimination in dermatology clinical images. Computerized Medical Imaging and Graphics 27:387-396, 2003.

Steger96 Steger C. Extracting lines using differential geometry and Gaussian smoothing. Int Arch Photogrammetry Remote Sensing 3(3):821-826, 1996.

Stoecker05a Stoecker W V, Gupta K, Stanley R J, Moss R H. Detection of asymmetric blotches in dermoscopy images of malignant melanoma using relative color. Skin Res Technol. 2005 August; 11(3):179-84. [In press], Skin Res Technol, 2005

Stolz96 Stolz W, Schiffner R, Pillet L, et al. Improvement of monitoring of melanocytic skin lesions with the use of a computerized acquisition and surveillance unit with a skin surface microscopic television camera. J Am Acad Dermatol 35:202-7, 1996.

Stolz01 Stolz W: DermoGenius Ultra. Presentation at the International Society of Digital Imaging of the Skin, Washington D.C., March 2001.

Tatikonda02 Tatikonda, S. Automatic detection of regression and granularity in dermatoscopy images of skin cancer. MS Thesis, 2002, Department of Electrical and Computer Engineering, University of Missouri, Rolla.

Thorn98 Thorn M, Penten F, Johansson B et al: Rapid increase in diagnosis of cutaneous melanoma in situ in Sweden, 1968-1992. Ca Detection and Prevention 22: 430, 1998

Umbaugh05 Umbaugh S E: Computer Imaging: Digital Image Analysis and Processing, The CRC Press, Boca Raton, Fla., 2005

Vincent 91 Vincent L and Soille P: "Watersheds in digital spaces: An efficient algorithm based on immersion simulations," IEEE Trans. Pattern Analysis & Machine Intelligence, vol. 13, no. 6, pp. 583-598, 1991.

The invention claimed is:

1. A method for automatically identifying a border between a skin lesion and surrounding skin on a digital image of a skin lesion comprising:
   a. preprocessing the image to identify pixels that represent features other than skin and lesion;
   b. identifying a bounding box in the shape of a rectangle having four sides by bounding box methods wherein the box borders are determined by a maxima of subtraction curves applied to horizontal and vertical projections of numbers representing a single-plane image of the lesion to determine a first lesion ratio estimate of the image; and wherein the absence of a bounding box side indicates that the lesion may extend to the periphery of the image, and the presence of a bounding box indicates that the lesion does not extend to the periphery of the image;
   c. if one or more bounding box sides are not found, determining a first estimate of the lesion ratio, which is the ratio of the area of the lesion to the area of the entire image, using a mean lesion ratio estimate wherein the mean lesion ratio estimate is applied to provide approximate location(s) of any missing bounding box sides;
   d. subsequently applying a lesion ratio offset, which is a correction factor, to the lesion ratio estimate to produce a corrected lesion ratio estimate, said lesion ratio offset being determined by running an automatic, self-training classifier algorithm that incorporates color and histogram data from the area defined by the bounding box sides identified in step b or c and/or by an area identified by inputting the lesion ratio estimate into a segmentation algorithm for identifying a border between a skin lesion and the surrounding skin; and
   e. inputting said corrected lesion ratio estimate into a segmentation algorithm for identifying a border between a skin lesion and surrounding skin;
   whereby said border is determined automatically.

2. The method of claim 1, wherein said single-plane image is represented by assigning weights, which sum to one, to R, G, and B or to the color planes being used in a different color space.

3. The method of claim 1, wherein the classifier algorithm applied to discriminate whether or not the lesion extends to the periphery of the image is a supervised feature-based classifier algorithm.

4. The method of claim 1 also comprising analyzing objects identified by means of a single-plane image represented by assigning different weights to R, G, and B or to the color planes being used in a different color space to create an independent histogram pursuit transform plane to identify objects to be merged into a lesion area of the segmentation algorithm.

5. The method of claim 1 also comprising identifying non-skin and nonlesion objects on an original digital image of a skin lesion by a method comprising:
   a. analyzing said image with a first digital hair removal algorithm;
   b. locating lesion borders on the original image; and
   c. applying a second, modified digital hair removal algorithm to the original image in which lower thresholds for noise are implemented outside the lesion border than inside the lesion border.

6. The method of claim 5, wherein said modified digital hair removal algorithm comprises determination of an adaptive morphology threshold.

7. The method of claim 5, wherein said modified digital hair removal algorithm comprises an area filter.

8. The method of claim 5 in which the thresholds for said modified digital hair removal algorithm are adjusted for sensitivity by selecting thresholds having the highest signal-to-noise ratio, and highest hit ratio.

9. The method of claim 5 in which said first digital hair removal algorithm comprises a hair mask and said modified digital hair removal algorithm has been modified to comprise an algorithm for identifying unusual hair width, wherein said hair mask is iteratively dilated by a single unit until there is no significant change in the number of pixels present with a luminance below the median of luminance of the pixels within the hair mask, thereby arriving at an adequate hair mask for unusual hair width.

10. The method of claim 5 comprising detection of bubbles in which a minimal luminance threshold is demanded of a candidate bubble pixel, and an additional criterion is demanded comprising:
    a. the candidate pixel is a salient point; or
    b. the candidate pixel is found by the modified digital hair removal algorithm.

11. The method of claim 1 also comprising identifying structures that discriminate malignant melanomas from benign skin lesions on a digital image of a skin lesion by a method comprising:
    a. detecting dark structures on said image, and assigning numerical values representative of measurements of said structures for input into a classifier algorithm; and
    b. running said classifier algorithm to discriminate malignant melanomas from benign skin lesions based at least partially on measurements of said structures.

12. The method of claim 11, wherein said dark structures are detected by a method comprising calculating crisp thresholds for inclusion of pixels of said image within said structures.

13. The method of claim 11, wherein said dark structures are detected by a method comprising calculating fuzzy indices to determine thresholds for inclusion of pixels of said image within said structures, said method comprising selecting optimal alpha cuts.

14. The method of claim 11, wherein said dark structures are detected by a method comprising analysis of a local area drop histogram.

15. The method of claim 11, wherein said dark structures are given ratings on one or more scalable indices selected from the group consisting of eccentricity, periphery of the structure, total area of the structure, area of the structure relative to the area of the lesion, total number of structures, shape irregularity, clustering, structure color, structure brightness variance, and melanoma color index.

16. The method of claim 11, wherein atypical pigment network indices are input into the classifier algorithm.

17. The method of claim 11, wherein salient point indices are input into the classifier algorithm.

18. The method of claim 11, wherein border gradient indices are input into the classifier algorithm.

19. The method of claim 11, wherein color clustering indices are input into the classifier algorithm.

20. The method of claim 1 wherein the segmentation algorithm is a watershed algorithm applied to a single-plane image.

21. The method of claim 20 wherein the watershed algorithm is a flooding algorithm.

22. The method of claim 1 wherein said automatic classifier is selected from the group consisting of linear classifiers, non-linear classifiers, tree-based algorithms, and neural networks.

* * * * *

UNITED STATES PATENT AND TRADEMARK OFFICE
CERTIFICATE OF CORRECTION

PATENT NO.        : 7,689,016 B2                                              Page 1 of 1
APPLICATION NO.   : 11/421031
DATED             : March 30, 2010
INVENTOR(S)       : William V. Stoecker et al.

It is certified that error appears in the above-identified patent and that said Letters Patent is hereby corrected as shown below:

Please delete the text of the Certificate of Correction filed September 2, 2011, specifying government support of the invention, and insert the following in column 1, line 11, after the paragraph entitled "CROSS-REFERENCE TO RELATED APPLICATIONS":

--STATEMENT REGARDING FEDERALLY SPONSORED RESEARCH OR DEVELOPMENT

This invention was made with government support under Grant Numbers 1R43CA101639-01 and 2R44CA101639-02A2 awarded by National Institutes of Health (NIH). The government has certain rights in the invention.--

Signed and Sealed this
Tenth Day of January, 2012

David J. Kappos
*Director of the United States Patent and Trademark Office*